(12) United States Patent
Bender et al.

(10) Patent No.: US 10,501,489 B2
(45) Date of Patent: Dec. 10, 2019

(54) C17-ALKANEDIYL AND ALKENEDIYL DERIVATIVES OF OLEANOLIC ACID AND METHODS OF USE THEREOF

(71) Applicant: REATA PHARMACEUTICALS, INC., Irving, TX (US)

(72) Inventors: Christopher F. Bender, Garland, TX (US); Xin Jiang, Coppell, TX (US); Eric Anderson, Southlake, TX (US); Melean Visnick, Irving, TX (US)

(73) Assignee: REATA PHARMACEUTICALS, INC., Irving, TX (US)

( * ) Notice: Subject to any disclaimer, the term of this patent is extended or adjusted under 35 U.S.C. 154(b) by 0 days.

(21) Appl. No.: 15/433,100

(22) Filed: Feb. 15, 2017

(65) Prior Publication Data

US 2017/0260227 A1    Sep. 14, 2017

Related U.S. Application Data

(62) Division of application No. 14/022,986, filed on Sep. 10, 2013, now Pat. No. 9,593,074.

(60) Provisional application No. 61/780,540, filed on Mar. 13, 2013, provisional application No. 61/699,122, filed on Sep. 10, 2012.

(51) Int. Cl.
| | |
|---|---|
| *C07J 63/00* | (2006.01) |
| *C07C 255/47* | (2006.01) |
| *C07D 207/08* | (2006.01) |
| *C07D 207/12* | (2006.01) |
| *C07D 211/46* | (2006.01) |
| *C07D 213/75* | (2006.01) |
| *C07D 233/90* | (2006.01) |
| *C07D 295/205* | (2006.01) |
| *C07D 305/08* | (2006.01) |

(52) U.S. Cl.
CPC ........... *C07J 63/008* (2013.01); *C07C 255/47* (2013.01); *C07D 207/08* (2013.01); *C07D 207/12* (2013.01); *C07D 211/46* (2013.01); *C07D 213/75* (2013.01); *C07D 233/90* (2013.01); *C07D 295/205* (2013.01); *C07D 305/08* (2013.01)

(58) Field of Classification Search
CPC .. C07C 285/47; C07D 307/08; C07D 307/12; C07D 211/46; C07D 213/75; C07D 233/90; C07D 295/203
USPC ...................................... 514/237.4
See application file for complete search history.

(56) References Cited

U.S. PATENT DOCUMENTS

| | | | |
|---|---|---|---|
| 4,395,423 A | 7/1983 | Neumann | |
| 5,064,823 A | 11/1991 | Lee et al. | |
| 6,326,507 B1 | 12/2001 | Gribble et al. | |
| 6,369,101 B1 | 4/2002 | Carlson | |
| 6,552,075 B2 | 4/2003 | Gribble et al. | |
| 6,642,217 B2 | 11/2003 | Krasutsky et al. | |
| 6,649,654 B1 | 11/2003 | Karin et al. | |
| 6,951,847 B2 | 10/2005 | Gibson et al. | |
| 6,974,801 B2 | 12/2005 | Honda et al. | |
| 7,053,119 B2 | 5/2006 | Karin et al. | |
| 7,144,875 B2 | 12/2006 | Gibson et al. | |
| 7,176,237 B2 | 2/2007 | Honda et al. | |
| 7,288,568 B2 | 10/2007 | Gribble et al. | |
| 7,399,606 B2 | 7/2008 | Karin et al. | |
| 7,410,958 B2 | 8/2008 | Krasutsky et al. | |
| 7,435,755 B2 | 10/2008 | Konopleva et al. | |
| 7,678,830 B2 | 3/2010 | Honda et al. | |
| 7,714,012 B2 | 5/2010 | Honda et al. | |
| 7,795,305 B2 | 9/2010 | Konopleva et al. | |
| 7,863,327 B2 | 1/2011 | Gribble et al. | |

(Continued)

FOREIGN PATENT DOCUMENTS

| | | |
|---|---|---|
| CN | 101 117 348 | 2/2008 |
| CN | 102 070 697 A | 5/2011 |

(Continued)

OTHER PUBLICATIONS

Abraham and Kappas, "Heme oxygenase and the cardiovascular-renal system", *Free Radic. Biol. Med.*, 2005, 39(1):1-25.

(Continued)

*Primary Examiner* — Sabiha N Qazi
(74) *Attorney, Agent, or Firm* — Parker Highlander PLLC

(57) ABSTRACT

Disclosed herein are novel C17-alkanediyl and alkenediyl derivatives of oleanolic acid, including those of the formula:

(I)

wherein the variables are defined herein. Also provided are pharmaceutical compositions, kits and articles of manufacture comprising such compounds. Methods and intermediates useful for making the compounds, and methods of using the compounds, for example, as antioxidant inflammation modulators, and compositions thereof are also provided.

15 Claims, No Drawings

Specification includes a Sequence Listing.

(56) References Cited

U.S. PATENT DOCUMENTS

| | | | |
|---|---|---|---|
| 7,915,402 B2 | 3/2011 | Anderson et al. | |
| 7,943,778 B2 | 5/2011 | Jiang et al. | |
| 8,034,955 B2 | 10/2011 | Gribble et al. | |
| 8,067,394 B2 | 11/2011 | Honda et al. | |
| 8,067,465 B2 | 11/2011 | Honda et al. | |
| 8,071,632 B2 | 12/2011 | Jiang et al. | |
| 8,088,824 B2 | 1/2012 | Walling et al. | |
| 8,124,656 B2 | 2/2012 | Anderson et al. | |
| 8,124,799 B2 | 2/2012 | Anderson et al. | |
| 8,129,429 B2 | 3/2012 | Sporn et al. | |
| 8,258,329 B2 | 9/2012 | Anderson et al. | |
| 8,299,046 B2 | 10/2012 | Sporn et al. | |
| 8,314,137 B2 | 11/2012 | Honda et al. | |
| 8,338,618 B2 | 12/2012 | Jiang et al. | |
| 8,394,967 B2 | 3/2013 | Jiang et al. | |
| 8,440,820 B2 | 5/2013 | Anderson et al. | |
| 8,440,854 B2 | 5/2013 | Anderson et al. | |
| 8,455,544 B2 | 6/2013 | Sporn et al. | |
| 8,513,436 B2 | 8/2013 | Anderson et al. | |
| 8,586,775 B2 | 11/2013 | Gribble et al. | |
| RE45,288 E | 12/2014 | Anderson et al. | |
| 8,921,419 B2 * | 12/2014 | Gribble | C07C 61/29 514/510 |
| RE45,325 E | 1/2015 | Anderson et al. | |
| 8,993,640 B2 | 3/2015 | Anderson et al. | |
| 9,090,574 B2 | 7/2015 | Anderson et al. | |
| 9,102,681 B2 | 8/2015 | Anderson et al. | |
| 9,249,089 B2 | 2/2016 | Jiang et al. | |
| 9,278,912 B2 | 3/2016 | Jiang et al. | |
| 9,278,913 B2 | 3/2016 | Gribble et al. | |
| 9,290,536 B2 | 3/2016 | Anderson et al. | |
| 9,556,222 B2 | 1/2017 | Anderson et al. | |
| 9,593,074 B2 * | 3/2017 | Bender | C07J 63/008 |
| 9,670,147 B2 | 6/2017 | Anderson et al. | |
| 9,701,709 B2 | 7/2017 | Anderson et al. | |
| 9,889,143 B2 * | 2/2018 | Jiang | C07D 271/10 |
| 2002/0042535 A1 | 4/2002 | Gribble et al. | |
| 2003/0119732 A1 | 6/2003 | Konopleva et al. | |
| 2003/0232786 A1 | 12/2003 | Honda et al. | |
| 2003/0236303 A1 | 12/2003 | Gribble et al. | |
| 2004/0002463 A1 | 1/2004 | Honda et al. | |
| 2004/0097436 A1 | 5/2004 | Krasutsky et al. | |
| 2005/0208151 A1 | 9/2005 | Hurez et al. | |
| 2005/0288363 A1 | 12/2005 | Gribble et al. | |
| 2006/0258752 A1 | 11/2006 | Vander Jagt et al. | |
| 2007/0232577 A1 | 10/2007 | Xu et al. | |
| 2007/0244081 A1 | 10/2007 | Krasutsky et al. | |
| 2007/0249561 A1 | 10/2007 | Taylor | |
| 2007/0259839 A1 | 11/2007 | Krasutsky et al. | |
| 2007/0259842 A1 | 11/2007 | Krasutsky et al. | |
| 2008/0220057 A1 | 9/2008 | Gribble et al. | |
| 2008/0233195 A1 | 9/2008 | Sporn et al. | |
| 2008/0254055 A1 | 10/2008 | Oblong et al. | |
| 2008/0261985 A1 | 10/2008 | Honda et al. | |
| 2009/0048204 A1 | 2/2009 | Walling et al. | |
| 2009/0048205 A1 | 2/2009 | Meyer et al. | |
| 2009/0060873 A1 | 3/2009 | Sporn et al. | |
| 2009/0093447 A1 | 4/2009 | Konopleva et al. | |
| 2009/0326063 A1 | 12/2009 | Sporn et al. | |
| 2010/0041904 A1 | 2/2010 | Jiang et al. | |
| 2010/0048887 A1 | 2/2010 | Anderson et al. | |
| 2010/0048892 A1 | 2/2010 | Anderson et al. | |
| 2010/0048911 A1 | 2/2010 | Anderson et al. | |
| 2010/0056777 A1 | 3/2010 | Anderson et al. | |
| 2010/0261930 A1 | 10/2010 | Honda et al. | |
| 2011/0009363 A1 | 1/2011 | Honda et al. | |
| 2011/0196007 A1 | 8/2011 | Honda et al. | |
| 2011/0245206 A1 | 10/2011 | Jiang et al. | |
| 2011/0245233 A1 | 10/2011 | Anderson et al. | |
| 2011/0281955 A1 * | 11/2011 | Meyer | A61K 31/56 514/661 |
| 2012/0022156 A1 | 1/2012 | Zhang et al. | |
| 2012/0071684 A1 | 3/2012 | Walling et al. | |
| 2012/0101149 A1 | 4/2012 | Honda et al. | |
| 2012/0196880 A1 | 8/2012 | Anderson et al. | |
| 2012/0214814 A1 | 8/2012 | Anderson et al. | |
| 2012/0220652 A1 | 8/2012 | Sporn et al. | |
| 2012/0238767 A1 | 9/2012 | Jiang et al. | |
| 2012/0245374 A1 | 9/2012 | Anderson et al. | |
| 2012/0252776 A1 | 10/2012 | Anderson et al. | |
| 2012/0283450 A1 | 11/2012 | Anderson et al. | |
| 2013/0237721 A1 | 9/2013 | Gribble et al. | |
| 2013/0274480 A1 | 10/2013 | Honda et al. | |
| 2013/0303607 A1 | 11/2013 | Gribble et al. | |
| 2013/0303797 A1 | 11/2013 | Gribble et al. | |
| 2013/0317007 A1 | 11/2013 | Anderson et al. | |
| 2013/0324559 A1 | 12/2013 | Johnson et al. | |
| 2013/0324599 A1 | 12/2013 | Anderson et al. | |
| 2013/0345276 A1 | 12/2013 | Sporn et al. | |
| 2014/0066408 A1 | 3/2014 | Jiang et al. | |
| 2014/0088163 A1 | 3/2014 | Jiang et al. | |
| 2014/0088188 A1 | 3/2014 | Jiang et al. | |
| 2014/0100227 A1 | 4/2014 | Bender et al. | |
| 2014/0179928 A1 | 6/2014 | Anderson et al. | |
| 2014/0275618 A1 | 9/2014 | Gribble et al. | |
| 2015/0011627 A1 | 1/2015 | Gribble et al. | |
| 2015/0148384 A1 | 5/2015 | Anderson et al. | |
| 2015/0152071 A1 | 6/2015 | Jiang et al. | |
| 2015/0259377 A1 | 9/2015 | Anderson et al. | |
| 2015/0376121 A1 | 12/2015 | Anderson et al. | |
| 2017/0165278 A1 | 6/2017 | Jiang et al. | |

FOREIGN PATENT DOCUMENTS

| | | |
|---|---|---|
| CN | 102 079 772 | 6/2011 |
| CN | 102 250 189 | 11/2011 |
| CN | 102887936 | 10/2012 |
| CN | 103788166 | 10/2012 |
| CN | 102 093 462 A | 11/2012 |
| JP | 55 055153 | 4/1980 |
| JP | 2001 240573 | 9/2001 |
| JP | 2005 314381 | 11/2005 |
| JP | 2008 110962 | 5/2008 |
| JP | 2008 247898 | 10/2008 |
| WO | WO 1999/065478 | 12/1999 |
| WO | WO 2000/73253 | 12/2000 |
| WO | WO 2002/003996 | 1/2002 |
| WO | WO 2002/026761 | 4/2002 |
| WO | WO 2002/026762 | 4/2002 |
| WO | WO 2002/032410 | 4/2002 |
| WO | WO 2002/047611 | 6/2002 |
| WO | WO 2002/092768 | 11/2002 |
| WO | WO 2003/059339 | 7/2003 |
| WO | WO 2003/062260 | 7/2003 |
| WO | WO 2004/064723 | 8/2004 |
| WO | WO 2004/089357 | 10/2004 |
| WO | WO 2005/042002 | 5/2005 |
| WO | WO 2005/046732 | 5/2005 |
| WO | WO 2006/029221 | 3/2006 |
| WO | WO 2007/005879 | 6/2007 |
| WO | WO 2007/112043 | 10/2007 |
| WO | WO 2007/127791 | 11/2007 |
| WO | WO 2008/000068 | 1/2008 |
| WO | WO 2008/000070 | 1/2008 |
| WO | WO 2008/016095 | 2/2008 |
| WO | WO 2008/064132 | 5/2008 |
| WO | WO 2008/064133 | 5/2008 |
| WO | WO 2008/097596 | 8/2008 |
| WO | WO 2008/111497 | 9/2008 |
| WO | WO 2008/136838 | 11/2008 |
| WO | WO 2009/023232 | 2/2009 |
| WO | WO 2009/023845 | 2/2009 |
| WO | WO 2009/058849 | 5/2009 |
| WO | WO 2009/089545 | 7/2009 |
| WO | WO 2009/129545 | 10/2009 |
| WO | WO 2009/129546 | 10/2009 |
| WO | WO 2009/129548 | 10/2009 |
| WO | WO 2009/146216 | 12/2009 |
| WO | WO 2009/146218 | 12/2009 |
| WO | WO 2010/011782 | 1/2010 |
| WO | WO 2010/053817 | 5/2010 |
| WO | WO 2010/093944 | 8/2010 |
| WO | WO 2011/130302 | 10/2011 |
| WO | WO 2011/140078 | 11/2011 |

(56) References Cited

FOREIGN PATENT DOCUMENTS

| | | |
|---|---|---|
| WO | WO 2012/106190 | 8/2012 |
| WO | WO 2012/125488 | 9/2012 |
| WO | WO 2012/154554 | 11/2012 |
| WO | WO 2013/163344 | 10/2013 |
| WO | WO 2013/169553 | 11/2013 |
| WO | WO 2013/169740 | 11/2013 |
| WO | WO 2013/188818 | 12/2013 |
| WO | WO 2014/037480 | 3/2014 |
| WO | WO 2014/040052 | 3/2014 |
| WO | WO 2014/040056 | 3/2014 |
| WO | WO 2014/040060 | 3/2014 |
| WO | WO 2014/040073 | 3/2014 |
| WO | WO 2014/048033 | 4/2014 |
| WO | WO 2014/176415 | 10/2014 |
| WO | WO 2015/027206 | 2/2015 |
| WO | WO 2017/053868 | 3/2017 |

OTHER PUBLICATIONS

Advisory Action issued in U.S. Appl. No. 14/022,986, dated Oct. 13, 2016.
Ahmad, et al., "Combining the FLT3 Inhibitor PKC412 and the Triterpenoid CDDO-Me Synergistically Induces Apoptosis in Acute Myeloid Leukemia with the Internal Tandem Duplication Mutation," *Mol. Cancer Res.*, 8(7):986-993, 2010.
Ahmad, et al., "Triterpenoid CDDO-Me blocks the NF-κB pathway by direct inhibition of IKKβ on Cys-179", *J. Biol. Chem.*, 2006, 281:35764-35769.
Ahmad, et al., "Triterpenoid CDDO-methyl ester inhibits the Janus-activated kinase-1 (JAK1) signal transducer and activator of transcription-3 (STAT3) pathway by direct inhibition of JAK1 and STAT3", *Cancer Res.*, 2008, 68(8): 2920-2926.
Akiyama, et al., "Cell mediators of inflammation in the Alzheimer disease brain", *Alzheimer Dis. Assoc. Disord.*, 2000, 14(1): S47-S53.
Alabran, et al., "Human neuroblastoma cells rapidly enter cell cycle arrest and apoptosis following exposure to C-28 derivatives of the synthetic triterpenoid CDDO," *Cancer Biology & Therapy*, 7(5):709-717, 2008.
Albini and Sporn, "Opinion: the tumour microenvironment as a target for chemoprevention", *Nature Reviews Cancer*, 2002, Abstract 501:149.
Alexeev, et al., "Radiation Protection of the Gastrointestinal Tract and Growth Inhibition of Prostate Cancer Xenografts," *Molecular Cancer Therapeutics*, 13(12):2968-2977, 2014.
Ames, et al., "The Triterpenoid CDDO-Me Promotes Hematopoietic Progenitor Expansion and Myelopoiesis in Mice," *Biol. Blood Marrow Tranplant.*, 18(3):396-405, 2012.
Andreef, et al., "PPARγ nuclear rescerptor as a novel molecular target in leukemias", 2002 Keystone Symposia, 2002, Abstract 501:149.
Andrew E. Place, "Pre-clincial evaluation of the novel synthetic triterpenoid CDDO-Imidazolide," Thesis, Dartmouth College, May 5, 2004.
Araujo, et al., "Systemic rather than local heme oxygenase-1 overexpression improves cardiac allograft outcomes in a new transgenic mouse", *J. Immunol.*, 2003, 171(3):1572-1580.
Auletta, et al., "The Synthetic Triterpenoid, CDDO-Me, Modulates the Proinflammatory Response to In Vivo Lipopolysaccharide Challenge," *J. Interferon Cytokine Res.*, 30(7):497-508, 2010.
Bach, et al., "Heme oxygenase-1 and transplantation tolerance", *Hum. Immun.*, 2006, 67(6):430-432.
Bai, et al., "Modified compounds from ursolic acid and their antitumor activities", *Huaxi Yaoxue Zazhi*, 2003, 18(2):87-90.
Ballesta-Acosta, et al., "A new 24-nor-oleanane triterpenoid from *Salvia carduacea*", *J. Nat. Prod*, 2002, 65(10):1513-1515.
Barton, et al., "The Synthesis of β-amyrin", *Journal of the Chemical Society*, 1968, 1031-1040.
Bensasson, et al., "Potency ranking of triterpenoids as inducers of a cytoprotective enzyme and as inhibitors of a cellular inflammatory response via their electron affinity and their electrophilicity index," *Chem. Biol. Interact.*, 186(2):118-126, 2010.
Bore, et al., "The anti-inflammatory triterpenoid methyl 2-cyano-3,12-dioxoolean 1,9(11)-dien-28-oate methanol solvate hydrate", *Acta Crystallorg C.*, 2002, 58(Pt 3):o199-o200.
Bowden, et al., "Constituents of the fruit of pseudopanax arboretum (Araliaceae)", *Australian Journal of Chemistry*, 1975, 28(1):91-107.
Brookes, et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore", *Cancer Res.*, 2007, 67:1793-18.
Buchanan, et al., "The conversion of turraeanthin and turraeanthin A into simple melaiacins by a route involving an oxidative rearrangement of probable biogenetic importance", *J. Chem. Soc. C*, 1970, 17:2280-2284.
Chadalapaka, et al., "Structure-dependent inhibition of bladder and pancreatic cancer cell growth by 2-substituted glycyrrhetinic and ursolic acid derivatives," *Bioorganic & Medicinal Chemistry Letters*, 18:2633-2639, 2008.
Chauhan and Chauhan, "Oxidative stress in autism", *Pathophysiology*, 2006, 13(3):171-181.
Chauhan, et al., "The bortezomib/proteasome inhibitor PS-341 and triterpenoid CDDO-Im induce synergistic anti-multiple myeloma (MM) activity and overcome bortezomib resistance", *Blood*, 2004, 103:3158-3166.
Chintharlapalli, et al., "Structure-dependent activity of glycyrrhetinic acid derivatives as peroxisome proliferator-activated receptor γ agonists in colon cancer cells", *Molecular Cancer Therapeutics*, 2007, 6(5):1588-1598.
Chintharlapalli, et al., "2-Cyano-3,12-dioxoolean-1,9-dien-28-oic acid and related compounds inhibit growth of colon cancer cells through peroxisome proliferator-activated receptor γ-dependent and -independent pathways", *Mol. Pharmacol.*, 2005, 68:119-128.
Chintharlapalli, et al., "2-Cyano-lup-1-en-3-oxo-20-oic acid, a cyano derivative of betulinic acid, activates peroxisome proliferator-activated receptor γ in colon and pancreatic cancer cells.", *Carcinogenesis*, 2007, 28(11):2337-2346.
clinicaltrials.gov Study Record, NCT 00352040, "CDDO in treating patients with metastatic or unresectable solid tumors or lymphoma conditions: lymphoma; small intestine cancer; unspecified adult solid tumor, protocol specifc", update of Jul. 6, 2009.
clinicaltrials.gov Study Record, NCT 00508807, "RTA 402 in advanced solid tumors or lymphoid malignancies", update as of Sep. 7, 2008.
clinicaltrials.gov Study Record, NCT 00508807, "RTA 402 in advanced solid tumors or lymphoid malignancies conditions: lymphoid malignancies; solid tumors", update of Aug. 27, 2008.
clinicaltrials.gov Study Record, NCT 00508807, "RTA 402 in advanced solid tumors or lymphoid malignancies conditions: lymphoid malignancies; solid tumors", update of Oct. 5, 2010.
clinicaltrials.gov Study Record, NCT 00529113, "Study with gemcitabine and RTA 402 for patients with unresectable pancreatic cancer", update of Dec. 1, 2010.
clinicaltrials.gov Study Record, NCT 00529113, "Study with gemcitabine and RTA 402 for patients with unresectable pancreatic cancer", update of Jun. 12, 2008.
clinicaltrials.gov Study Record, NCT 00529438, "RTA 402 in patients with advanced solid tumors or lymphoid malignancies conditions: advanced solid tumors; lymphoid malignancies", update of Dec. 21, 2008.
clinicaltrials.gov Study Record, NCT 00550849, "Study to assess the safety, tolerability, and pharmacodynamics of RTA 402 in patients with hepatic dysfunction", update as of Oct. 29, 2007.
clinicaltrials.gov Study Record, NCT 00550849, "Study to assess the safety, tolerability, and pharmacodynamics of RTA 402 in patients with hepatic dysfunction condition: liver disease", update of Nov. 6, 2007.

(56) References Cited

OTHER PUBLICATIONS clinicaltrials.gov Study Record, NCT 00664027, "Phase IIa trail to determine the effects of bardoxolone methyl on renal function in patients with diabetic nephropathy", update as of Dec. 21, 2008.
clinicaltrials.gov Study Record, NCT 00664027, "Phase IIa trial to determine the effects of bardoxolone methyl on renal function in patients with diabetic nephropathy condition: diabetic nephropathy", update of Feb. 18, 2009.
clinicaltrials.gov Study Record, NCT 00664027, "Phase IIa trial to determine the effects of bardoxolone methyl on renal function in patients with diabetic nephropathy condition: diabetic nephropathy", update of Jun. 25, 2011.
clinicaltrials.gov Study Record, NCT 00811889, "Trial to determine the effects of bardoxolone methyl on eGFR in patients with type 2 diabetes and chronic kidney disease conditions: chronic kidney disease; type 2 diabetes; diabetic nephropathy", update as Jun. 4, 2009.
clinicaltrials.gov Study Record, NCT0352040, "CDDO in treating patients with metastatic or unresectable solid tumors or lymphoma", update as of Dec. 11, 2008.
Cohen, et al., "A general method for removal of a 4-methyl group from triterpenoids. Synthesis of 4β-demethylgylycyrrhetinic acid", *J. Chem. Soc. Perkin Trans. 1*, 1973, 19:2076-2082.
Connolly, et al., "Grandiofolione: a novel tetranortriterpenoid", Chemical Communications, 1966, 23:567-568.
Couch, et al., "2-cyano-3,12-dioxooleana-1,9(11)-diene-28-oic Acid Disrupts Microtubule Polymerization: A Possible Mechanism Contributing to Apoptosis", *Molecular Pharmacology*, 2006, 69:1158-1165.
Couch, et al., "Studies on the reactivity of CDDO, a promising new chemopreventive and chemotherapeutic agent: implications for a molecular mechanism of action", *Bioorganic and Medicinal Chemistry Letters*, 2005, 15(9):2215-2219.
Damsté, et al., "A sedimentary tetrahydrophenanthrene derivative of tetrahymanol", *Tetrahedron Letters*, 1999, 40(20):3949-3952.
De Mico, et al., "A Versatile and Highly Selective Hypervalent Iodine (III)/2,2,6,6-Tetramethyl-1-piperidinyloxyl-Mediated Oxidation of Alcohols to Carbonyl Compounds", *J. Org. Chem.*, 1997, 62:6974.
De Zeeuw, et al., "Bardoxolone methyl in type 2 diabetes and stage 4 chronic kidney disease," *New Engl. J. Med.*, 369(26):2492-2503, 2013.
Dean, et al., "Halogenolysis of methyl glycyrrhetate with lithium iodidedimethylformamide", *J. Chem. Soc.*, 1965, 6655-6659.
Deeb, et al., "CDDO-Me Induces Apoptosis and Inhibits Akt, mTOR and Nf-kB Signaling Proteins in Prostate Cancer Cells", *Anticancer Research*, 2007, 27:3035-3044.
Deeb, et al., "CDDO-Me inhibits proliferation, induces apoptosis, down-regulates Akt, mTOR, Nf-κB and Nf-κB-regulated antiapoptotic and proangiogenic proteins in TRAMP prostate cancer cells," *J. of Experimental Therapeutics and Oncology*, 7:31-39, 2008.
Deeb, et al., "CDDO-Me: a novel synthetic triterpenoid for the treatment of pancreatic cancer," *Cancers*, 2:1779-1793, 2010.
Deeb, et al., "Oleanane triterpenoid CDDO-Me inhibits growth and induces apoptosis in prostate cancer cells through a ROS-dependent mechanism," *Biochem. Pharmacol.*, 79(3):350-360, 2010.
Deeb, et al., "Oleanane triterpenoid CDDO-Me inhibits growth and induces apoptosis in prostate cancer cells by independently targeting pro-survival Akt and mTOR," *Prostate*, 69(8):851-860, 2009.
Deng and Synder, "Preparation of a 24-Nor-1,4-dien-3-one triterpene derivative from betulin: a new route to 24-nortriterpene analogues", *J. of Organic Chemistry*, 2002, 67(9):2864-2873.
Dezube, et al., "Interim results of a phase I trial with a novel orally administered synthetic triterpenoid RTA 402 (CDDO-Me) in patients with solid tumors and lymphoid malignancies", *J. Clin. Oncol.*, 2007 ASCO Annual Meeting Proceedings, 2007, 25(18S):14101.
Dickerson, et al., "Elevated serum levels of C-reactive protein are associated with mania symptoms in outpatients with bipolar disorder", *Prog. Neuropyschopharmacol. Biol. Psychiatry*, 2007, 31(4):952-955.

Ding, et al., "DDQ-promoted dehydrogenation from natural rigid polycyclic acids or flexible alkyl acids to generate lactones by a radical mechanism," *Chem. Comm.*, 47(33)9495-9497, 2011.
Dinkova-Kostova, et al., "Direct evidence that sulfhydryl groups of Keap1 are the sensors regulating induction of phase 2 enzymes that protect against carcinogens and oxidants", *Proc. Natl. Acad. Sci.*, 2002, 99(18):11908-11913.
Dinkova-Kostova, et al., "Extremely potent triterpenoid inducers of the phase 2 response: correlations of protection against oxidant and inflammatory stress", *Proc. Natl. Acad. Sci.*, 2005, 102(12):4584-4589.
Dirsch, et al., "The triterpenoid quinomethide pristimerin inhibits induction of inducible nitric oxide synthase in murine macrophages", *Eur. J Pharmacol.*, 1997, 336(2-3):211-217.
Dracinsky, et al., "Preparation and Conformational Study of 19β,28-Epoxy-18α-olean-5-ene derivatives", *Collection of Czechoslovak Chemical Communications*, 2006, 71(3):387-410.
Dragnev, et al., "Specific chemopreventive agents trigger proteasomal degradation of G1 cyclins: implications for combination therapy", *Clin. Cancer Research*, 2004, 10(7): 2570-2577.
Duan, et al., "CDDO-Me, a synthetic triterpenoid, inhibits expression of IL-6 and Stat3 phosphorylation in multi-drug resistant ovarian cancer cells," *Cancer Chemother. Pharmacol.*, 63(4):681-689, 2009.
Duan, et al., "Di- and triterpenoids from *Triptergium hypoglaucum*", *Phytochemistry*, 1997, 46(3):535-543.
Duan, et al., "Immunosuppressive terpenoids from extracts of *Tripterygium wilfordii*", *Tetrahedron*, 2001, 57(40):8413-8424.
Elgamal, et al., "Glycyrrhetic acid derivatives with modified ring A", *J. of Pharmaceutical Sciences*, 1973, 62(9):1557-1558.
Elgamal, et al., "The C-2, C-3-glycol derivatives of glycyrrhetic acid", *Tetrahedron*, 1974, 30(23/24):4083-4087.
Elliot, et al., "The triterpenoid CDDO inhibits expression of matrix metalloproteinase-1, matrix metalloproteinase-13 and Bcl-3 in primary human chondrocytes", *Arthritis Res. Ther.*, 2003, 5:R285-R291.
Elsawa, et al., "CDDO-imidazolide mediated inhibition of malignant cell growth in Waldenstroem macroglobulinemia," *Leukemia Res.*, 32(12):1895-1902, 2008.
Elsawa, et al., "Preferential Inhibition of Malignant Cell Growth by CDDO in *Waldenstrom Macroglobulinemia*", *Blood*, 2006, 108(11):2528.
Eskiocak, et al., "CDDO-Me protects against space radiation-induced transformation of human colon epithelial cells," *Radiat. Res.*, 174(1):27-36, 2010.
Evers, et al., "Betulinic acid derivatives: a new class of human immunodeficiency virus type 1 specific inhibitors with a new mode of action", *J. of Medicinal Chemistry*, 1996, 39(5):1056-1068.
Favaloro, Jr., Frank G. et al., "Design and Synthesis of Tricyclic Compounds with Enone Functionalities in Rings A and C: A Novel Class of Highly Active Inhibitors of Nitric Oxide Production in Mouse Macrophages", *J. Med Chem.*, 2002, 45(22):4801-4805.
Finlay, et al., "Novel A-ring cleaved analogs of oleanolic and ursolic acids which affect growth regulation in NRP.152 prostate cells", *Bioorg. Med. Chem. Lett.*, 1997, 7(13): 1769-1772.
Finlay, et al., "The Effect of A and C Ring Modification of Oleanolic and Ursolic Acid on the Inhibition of Nitric Oxide Formation in Mouse Macrophages", 213th American Chemical Society National Meeting, Abstract:084, 1997.
Forstermann, "Janus-faced role of endothelial NO synthase in vascular disease: uncoupling of oxygen reduction from NO synthesis and its pharmacological reversal", *Biol Chem.*, 2006, 387:1521-1533.
Ganguly, et al., "Chemical constituents of *Glochidion hohenackeri*", *Tetrahedron*, 1966, 22:1513-1519.
Gao, et al., "Immunomodulatory Activity of Synthetic Triterpenoids: Inhibition of Lymphocyte Proliferation, Cell-Mediated Cytotoxicity, and Cytokine Gene Expression Through Suppression of NF-κB," *Immunopharmacol. Immunotoxicol.*, 30(3):581-600, 2008.
Gao, et al., "Synthetic triterpenoids inhibit growth and induce apoptosis in human glioblastoma and neuroblastoma cells through inhibition of prosurvival Akt, NF-κB and Notch1 signaling", *J. of Neurooncology*, 2007, 84(2): 147-157.

(56) References Cited

OTHER PUBLICATIONS

Gao, et al., "Synthetic triterpenoids inhibit growth, induce apoptosis and suppress pro-survival Akt, mTOR and NF-KB signaling protein in colorectal cancer cells," *Anticancer Res.*, 30(3):785-792, 2010.
Gheeya, et al., "Screening a panel of drugs with diverse mechanisms of action yields potential therapeutic agents against neuroblastoma," *Cancer Biol. Ther.*, 8(24):2386-2395, 2009.
Govindachari, et al., "Gymnosporol, a new pentacyclic triterpene from *Gymnosporia rothiana*", *Indian Journal of Chemistry*, 1970, 8(5):395-397.
Grant, et al., "Boron trifluoride catalyzed rearrangements of novel expoxide derivatives of manool and manoyl oxide", *Australian Journal of Chemistry*, 1993, 46(8):1125-1145.
Grieco and Speake, et al., "Synthetic Studies on Quassinoids: Total Synthesis and Biological Evaluation of (+)-Des-D-chaparrinone", *J. Org. Chem.*, 1998, 63:5929-5936.
Hail, et al., "Evidence supporting a role for calcium in apoptosis induction by the synthetic triterpenoid 2-cyano-3,12-dioxooleana-1,9-dien-28-oic acid (CDDO)", *J. Biol. Chem.*, 2004, 279:11179-11187.
Han, et al., "CDDO-Imidazolide inhibits growth and survival of c-Myc-induced mouse B cell and plasma cell neoplasms", *Molecular Cancer*, 2006, 5:22.
Hanson, et al., "Theories of schizophrenia: a genetic-inflammatory-vascular synthesis", *BMC Medical Genetics*, 2005, 6:7.
Heather E. Ferguson, "PPARγ ligands have potent anti-fibrotic activity: mechanism of action and implications for therapy of pulmonary fibrosis," Dissertation, University of Rochester, 2008.
Heiss, et al., "Active NF-E2-related factor (Nrf2) contributes to keep endothelial NO synthase (eNOS) in the coupled state: role of reactive oxygen species (ROS), eNOS, and heme oxygenase (HO-1) levels", *J. Biol. Chem.*, 2009, 284:31579-31586.
Hill, et al., "Synthetical approaches to the pristimerin chromophore", *J. of the Chemical Society*, 1965, 361-375.
Hirota, et al., "Suppression of tumor promoter-induced inflammation of mouse ear by ursolic acid and 4,4-dimethycholestane derivatives", *Agric. Biol. Chem.*, 1990, 54:1073-1075.
Hirota, et al., "Total synthesis of (±)-amarolide, a quassinoid bitter principle", *J. Org. Chem.*, 1991, 56:1119-1127.
Honda, et al., "2-Cyano-3,10-dioxooleana-1,9(11)-dien-28-oic acid anhydride. A novel and highly potent anti-inflammatory and cytoprotective agent," *Bioorg. Med. Chem. Lett.*, 20(7):2275-2278, 2010.
Honda, et al., "A novel dicyanotriterpenoid, 2-cyano-3,12-dioxooleana-1,9(11)-dien-28-onitrile, active at picomolar concentrations for inhibition of nitric oxide production", *Bioorg. Med. Chem. Lett.*, 2002, 12:1027-1030.
Honda, et al., "An efficient synthesis of tricyclic compounds (±)—(4aβ, 8aβ, 10βaa)—1,2,3,4,4a,6,7,8,8a,9,1-,10a-Dodecahydro-1,1,4a-Trimethyl-2-Oxophenanthrene-8a-Carboxolic acid, its methyl ester, and (±)-(4aβ,8aβ,10aα)-3,4,4a,6,7,8,8a,9,10,10a-Decahydro-8a-Hydroxymethyl-1,1,4a-Trimethylphenanthren-2(1H)-one", *Org. Prep. Proced Int.*, 2005, 37(6):546-550.
Honda, et al., "Design and synthesis of 23,24-dinoroleanolic acid derivatives, novel triterpenoid—steroid hybrid molecules", *J. Org. Chem.*, 1998, 63:4846-4849.
Honda, et al., "Design and synthesis of 2-cyano-3,12-dioxoolean-1,9-dien-28-oic acid, a novel and highly active inhibitor of nitric oxide production in mouse macrophages", *Bioorg Med Chem Lett.*, 1998, 8(19):2711-2714.
Honda, et al., "Design, Synthesis, and anti-inflammatory activity both in vitro and in vivo of new betulinic acid analogues having an enone functionality in ring A", *Bioorg. Med. Chem. Lett.*, 2006, 16(24):6306-6309.
Honda, et al., "Design, synthesis, and biological evaluation of biotin conjugates of 2-cyano-3,12-dioxooleana-1,9(11)-dien-28-oic acid for the isolation of the protein targets", *J. Med. Chem.*, 2004, 47(20):4923-4932.
Honda, et al., "Efficient synthesis of (–)- and (+)-tricyclic compounds with enone functionalities in rings A and C. A novel class of orally active anti-inflammatory and cancer chemopreventive agents", *Org Biomol Chem.*, 2003, 1:4384-4391.
Honda, et al., "New enone derivatives of oleanolic acid and ursolic acid as inhibitors of nitric oxide production in mouse macrophages", *Bioorg. Med. Chem. Lett.*, 1997, 7:1623-1628.
Honda, et al., "New synthetic oleanane and ursane triterpenoids as inhibitors of nitric oxide production in mouse macrophages", The Fifth Chemical Congress of North America, Cancun, Mexico, Abstract 552 and slides for oral presentation, Nov. 1997.
Honda, et al., "Novel synthetic oleanane and ursane triterpenoids with various enone functionalities in ring A as inhibitors of nitric oxide production in mouse macrophages", *J. Med. Chem.*, 2000, 43:1866-1877.
Honda, et al., "Novel synthetic oleanane triterpenoids: a series of highly active inhibitors of nitric oxide production in mouse macrophages", *Bioorg. Med. Chem. Lett.*, 1999, 9(24):3429-3434.
Honda, et al., "Novel tricyclic compounds having acetylene groups at C-8a and cyano enones in rings A and C: highly potent anti-inflammatory and cytoprotective agents", *J. Med. Chem.*, 2007, 50:1731-1734.
Honda, et al., "Revision and confirmation of the regiochemistry of isoxazoles derived from methyl oleanonate and lanost-8-en-3-one. Synthesis of a new lanostane triterpenoid with a cyano-enone functionality in ring A", *J. Org. Chem.*, 2003, 68:4991-4993.
Honda, et al., "Synthesis of (±)-3,3-ethylenedioxy-14a-hydroxy-5-picrasene-11,16-dione, a 14aH-picrasane derivative", *Chem. Lett.*, 1981, 299-302.
Honda, et al., "Synthesis of a novel dicyano abietane analogue: a potential antiinflammatory agent", *J. Org. Chem.*, 2006, 71:3314-3316.
Honda, et al., "Synthetic oleanane and ursane triterpenoids with modified rings A and C: A series of highly active inhibitors of nitric oxide production in mouse macrophages", *J. Med. Chem.*, 2000, 43:4233-4246.
Hong, et al., "A Phase I First-in-Human Trial of Bardoxolone Methyl in Patients with Advanced Solid Tumors and Lymphomas", *Clinical Cancer Research*, 2012, 18:3396-3406.
Hughes, et al., "The synthetic triterpenoid CDDO-Im inhibits fatty acid synthase expression and has antiproliferative and proapoptotic effects in human liposarcoma cells," *Cancer Investigation*, 26:118-127, 2008.
Huneck, "Triterpene, XIV: die bromierung von 19βB28-epoxy-3-oxo-2-diazo- und 1-oxo-2-diazo- sowie von 19β28-epoxy-1-oxo-18αH-oleanan", *Chemische Berichte*, 1965, 98(9):2837-2843, (German only, English CAPLUS database summary).
Hybertson, et al., "Oxidative stress in health and disease: The therapeutic potential of Nrf2 activation", *Molecular Aspects of Medicine*, 2011, 32:234-246.
Hyer, et al., "Apoptotic activity and mechanism of 2-cyano-3,12-dioxoolean-1,9-dien-28-oic acid and related synthetic triterpenoids in prostate cancer," *Cancer Res.*, 68:2927-2933, 2008.
Hyer, et al., "Synthetic triterpenoids cooperate with tumor necrosis factor-related apoptosis-inducing ligand to induce apoptosis of breast cancer cells", *Cancer Res.*, 2005, 65:4799-4808.
Ikeda, et al., "Induction of redox imbalance and apoptosis in multiple myeloma cells by the novel triterpenoid 2-cyano-3,12-dioxoolean-1,9-dien-28-oic acid", *Mol. Cancer Ther.*, 2004, 3:39-45.
Ikeda, et al., "The novel triterpenoid CDDO and its derivatives induce apoptosis by disruption of intracellular redox balance", *Cancer Res.*, 2003, 63:5551-5558.
Ikeda, et al., "Triterpenoid CDDO-Im downregulates PML/RAR α expression in acute promyelocytic leukemia cell", *Cell Death and Differentiation*, 2005, 12(5):523-531.
Inoue, et al., "CDDO induces apoptosis via the intrinsic pathway in lymphoid cells", *Leukemia*, 2004, 18(5):948-952.
Ishikawa, et al., "theme oxygenase-1 inhibits atherogenesis in Watanabe heritable hyperlipidemic rabbits", *Circulation*, 2001, 104(15):1831-1836.
Ito, et al., "Involvement of caspase-8 in the induction of osteosarcoma cell apoptosis by the novel triterpenoid CDDO", 47th Annual Meeting, Orthopaedic Research Society, Feb. 25-28, 2001, San Francisco, California, 2001, p. 0863, Poster Session.

(56) References Cited

OTHER PUBLICATIONS

Ito, et al., "The novel triterpenoid 2-cyano-3,12-dioxoolean-1,9-dien-28-oic acid induces apoptosis of human myeloid leukemia cells by a caspase-8-dependent mechanism", *Cell Growth & Differentiation*, 2000, 11(5):261-267.

Ito, et al., "The novel triterpenoid CDDO induces apoptosis and differentiation of human osteosarcoma cells by a caspase-8 dependent mechanism", *Mol. Pharmacol.*, 2001, 59:1094-1099.

Jang, et al., "24-nor-ursane type triterpenoids from the stems of *Rumex japonicas*", *Chem. Pharm. Bull (Tokyo)*, 2005, 53(12):1594-1596.

Ji, et al., "The synthetic triterpenoid CDDO-imidazolide induces monocytic differentiation by activating the Smad and ERK signaling pathways in HL60 leukemia cells", *Molecular Cancer Therapeutics*, 2006, 5(6):1452-1458.

Johansen, et al., "Pharmacology and preclinical pharmacokinetics of the triterpenoid CDDO methyl ester", *Proc. Amer. Assoc. Cancer. Res.*, 2003, 44:1728.

Jutooru, et al., "Methyl 2-cyano-3,12-dioxooleana-1,9-dien-28-oate decreases specificity protein transcription factors and inhibits pancreatic tumor growth: role of microRNA-27a," *Mol. Pharmacol.*, 78(2):226-236, 2010.

Kahne and Collum, "Kinetic Cyanation of Ketone Enolates", *Tetrahedron Lett.*, 1981, 22:5011-5014.

Kamal, et al., "23-oxoisopristimerin III: an new natural phenolic (9→4)-24-nor-D:A-friedo-oleanane triterpene", *Tetrahedron Letters*, 1983, 24(27):2799-2800.

Kamal, et al., "Structures of two new phenolic 24-nor-D:A-friedoleananes related to zeylasterone: a partial synthesis of trimethylzeylasterone", *Tetrahedron Letters*, 1983, 24(19):2025-2028.

Kamal, et al., "The structure of zeylasterone, the first of a new series of phenolic 24-nor-D: A friedo-oleanane triterpenes", *Tetrahedron Letters*, 1980, 21(49):4749-4752.

Kansanen, et al., "Regulation of Nrf2-dependent gene expression by 15-deoxy-delta12,14-prostaglandin J2", *Free Radic. Biol. Med.*, 2009, 47(9):1310-1317.

Kawakami, et al., "A comparative study of nitric oxide, glutathione, and glutathione peroxidase activities in cerebrospinal fluid from children with convulsive disease/children with aseptic meningitis", *Brain Dev.*, 2006, 28(4):243-246.

Kendall-Tackett, "Inflammation, cardiovascular disease, and metabolic syndrome as sequelae of violence against women: the role of depression, hostility, and sleep disturbance", *Trauma Violence Abuse*, 2007, 8(2):117-126.

Khalid, et al., "Isolation and characterization of pristimerin as the antiplasmodial and antileishmanial agent of *Maytenus senegalensis* (Lam.) Exell", *ARKIVOC*, 2007, 129-134.

Kim, et al., "An inducible Pathway for Degradation of FLIP protein Sensitizes Tumor Cells to TRAIL-induced Apoptosis", *J. Biological Chemistry*, 2002, 277(25):22320-22329.

Kim, et al., "Caspase-3 activation is Involved in Apoptosis Induced by a Synthetic Triterpenoid in Non-small Cell Lung Cancer (NSCLC) cells", *Proc. Amer. Assoc. Cancer. Res.*, 2000, 41:770, Abstract #4894.

Kim, et al., "Identification of a Novel Synthetic Triterpenoid, methyl-2-cyano-3,12-dioxooleana-1,9-dien-28-oate, that Potently Induces Caspase-mediated apoptosis in Human Lung Cancer Cells", *Molecular Cancer Therapeutics*, 2002, 1:177-184.

Kim, et al., "Mitigation of radiation-induced damage by targeting EGFR in noncancerous human epithelial cells," *Radiat. Res.*, 180(3):259-267, 2013.

Kircher, "Triterpenees, in organ pipe cactus", *Phytochemistry*, 1980, 19:2707-2712.

Klinot and Vystrcil, "Triterpenes. VII. Stereochemistry of 2-bromo derivatives of allobetuline and allohterobetaline", *Collection of Czechoslovak Chemical Communication*, 1966, 31(3):1079-1092.

Klinot, et al., "Triterpenes. Part LXXXVI. Triterpenoid 2,3-ketolis, diols and their acetates: preparation and conformation of the ring A", *Collection of Czechoslovak Chemical Communications*, 1989, 54(2):400-412.

Klyne, et al., "The molecular rotations of polycyclic compounds. III. Polycyclic alochols and their derivatives", *J. Chem. Soc.*, 1954, 1979-1988.

Kobayashi, et al., "The antioxidant defense system Keap1-Nrf2 comprises a multiple sensing mechanism for responding to a wide range of chemical compounds", *Mol. Cell Biol.*, 2009, 29(2):493-502.

Kolak, et al., "Antioxidant and anticholinesterase constituents of *Salvia poculata*", *Turkish Journal of Chemistry*, 2009, 33(6):813-823.

Kong, et al., "Synthetic triterpenoids have cytotoxicity in pediatric acute lymphoblastic leukemia cell lines but cytotoxicity is independent of induced ceramide increase in MOL T-4 cells," *Leukemia*, 22(6):1258-1262 2008.

Konopleva, et al., "PPARγ Ligand CDDO Induces Apoptosis in Leukemias Via Multiple Apoptosis Pathways", Abstracts of the 44th Annual Meeting of the American Society of Hematology, 2002, Abstract No. 2209.

Konopleva, et al., "PPARγ Ligands Are Potent Induces of Apoptosis in Leukemias and Lymphomas", American Society of Hematology 43rd Annual Meeting and Exposition, 2001, Abstract No. 501.

Konopleva, et al.,"PPARγ Nuclear Receptor as a Novel Molecular Target in Leukemia Therapy", *Proc. Amer. Assoc. Cancer Res.*, 2002, 43:4730.

Konopleva, et al., "PPARγ nuclear receptor as a novel therapeutic target in AML", *Proc. of the AACR*, 2001, 42, Abstract #4458.

Konopleva, et al., "PPARγ nuclear receptor as a novel therapeutic target in AML", *Blood*, 2000, 96(11):460a, Abstract #1982.

Konopleva, et al., "Suppression of ERK Activation is Required for Triterpenoid Methyl-CDDO-Induced Apoptosis in AML", *Blood*, 2003, 102(110:1404).

Konopleva, et al., "Synthetic triterpenoid 2-cyano-3,12-dioxooleana-1,9-dien-28-oic acid induces growth arrest in HER2-overexpressing breast cancer cells", *Mol. Cancer. Ther.*, 2006, 5:317-328.

Konopleva, et al., "Synthetic triterpenoid CDDO as a novel therapy for resistant breast cancer", *Proc. Amer. Assoc. Cancer Res.*, 2003, 44:2726.

Konopleva, et al., "The novel triterpenoid CDDO-Me suppresses MAPK pathways and promotes p38 activation in acute myeloid leukemia cells",*Leukemia*, 2005, 19:1350-1354.

Konopleva, et al., "The synthetic triterpenoid 2-cyano-3,12-dioxoolean-1,9-dien-28-oic acid induces caspase-dependent and -independent apoptosis in acute myelogenous leukemia", *Cancer Res.*, 2004, 64:7927-79358:2027-2057.

Konopleva, et al., "Activation of nuclear transcription factor PPARγ by the novel triterpenoid CDDO as targeted therapy in breast cancer", 2002 Keystone Symposium, 2002, Abstract No. 539.

Konopleva, et al., "Mechanisms and Activity of PPARγ-Active Triterpenoids CDDO and CDDO-Me in Leukemias", *Blood*, 2005, 106:2460.

Konopleva, et al., "Novel synthetic triterpenoid CDDO-Me: potent antiproliferative, proapoptotic and differentiating agent in AML", *Blood*, 2000, 96(11), Part 1:121A, abstract #522.

Konopleva, et al., "Novel synthetic triterpenoid, CDDO, and its methyl ester: Potent antiproliferative, proapoptotic and differentiating agent in AML", *Blood*, 1999, 94(Suppl 1):479a, Abstract #2140.

Konopleva, et al., "Novel triterpenoid CDDO-Me is a potent inhibitor of apoptosis and differentiation in acute myelogenous leukemia", *Blood*, 2002, 99(1):326-335.

Konopleva, et al., "Peroxisome proliferator-activated receptor γ and retinoid X receptor ligands are potent inducers of differentiation and apoptosis in leukemias", *Mol. Cancer Ther.*, 2004, 3:1249-1262.

Konopleva, et al., "Triterpenoid methyl-CDDO is a potent inducer of apoptosis in CD34+ AML progenitor cells via activation of SAPK pathways and inhibition of MAPK cascades", *Blood*, 2004, 104:2533.

(56) References Cited

OTHER PUBLICATIONS

Korovin and Tkachev, "Synthesis of quinoxalines fused with triterpenes, ursolic acid and betulin derivatives", *Russian Chemical Bulletin*, (Translation of Izvestiya Akademii Nauk, Seriya Khimicheskaya), 2001, 20(2):304-310.

Koschmieder, et al., "CDDO induces granulocytic differentiation of myeloid leukemic blasts through translational up-regulation of p42 CCAAT enhanced-binding protein α", Blood, 2007, 110(10):3695-3705.

Kress, et al., "Triterpenoids display single agent activity in a mouse model of CLL/SBL", *Blood*, 2006, 108(11):2530.

Kress, et al., "Triterpenoids display single agent anti-tumor activity in a transgenic mouse model of chronic lymphocytic leukemia and small B cell lymphoma", *PLOS ONE*, 2007, 6(e559):1-11.

Kruger, et al., "Up-regulation of heme oxygenase provides vascular protection in an animal model of diabetes through its antioxidant and antiapoptotic effects", *J. Pharmacol. Exp. Ther.*, 2006, 319(3):1144-1152.

Kurinna, et al., "The novel triterpenoid CDDO-Me promotes apoptosis in Gleevec-resistant chronic meyloid leukemia cells by caspase-independent mechanisms", *Proc. Amer. Assoc. Cancer Res.*, 2005, 46:2240.

Kutschabsky, et al., "Natural products from Vietnamese plants. Part XV. Molecular and crystal structure of a new 24-nor triterpenoid carboxylic acid from *Acanthopanax tri oliatus*", *Croatica Chemica Acta*, 1986, 58(4):427-434.

Lapillonne, et al., "Activation of peroxisome proliferator-activated receptor γ by a novel synthetic triterpenoid 2-cyano-3,12-dioxooleana-1,9-dien-28-oic acid induces growth arrest and apoptosis in breast cancer cells", *Cancer Res.*, 2003, 63:5926-5939.

Lavie, et al., "Tetranortriterpenoids from *Melia azadirachta*", *Chemical Communications*, 1967, 6:278-280.

Lavie, et al., "Studies on epoxides. IV. Rearrangements in triterpenoids", *Tetrahedron Letters*, 1968, 17:2097-2100.

Lee, et al., "Double-stranded RNA induces iNOS gene expression in Schwann cells, sensory neuronal death, and peripheral nerve demyelination", *Glia*, 2007, 55(7):712-722.

Lencz, et al., "Converging evidence for a pseudoautosomal cytokine receptor gene locus in schizophrenia", *Molecular Psychiatry*, 2007, 12(6):572-580.

Li, et al., "Terpenoids from *Tripterygium wilfordii*", *Phytochemistry*, 1997, 45(4):791-796.

Li, et al., "The triterpenoid CDDO-Me delays murine acute graft-versus-host disease with the preservation of graft-versus-tumor effects after allogeneic bone marrow transplantation," *Biol. Blood Marrow Transplant.*, 16(6):739-750, 2010.

Liby, et al., "A novel acetylenic tricyclic bis-(cyano enone) potently induces phase 2 cytoprotective pathways and blocks liver carcinogenesis induced by aflatoxin", *Cancer Res.*, 2008, 68:6727-6733.

Liby, et al., "Novel semisynthetic analogues of betulinic acid with diverse cytoprotective, antiproliferative, and proapoptotic activities", *Mol. Cancer Ther.*, 2007, 6(7):2113-2119.

Liby, et al., "Prevention and Treatment of Experimental Estrogen Receptor-Negative Mammary Carcinogenesis by the Synthetic Triterpenoid CDDO-Methyl Ester and the Rexinoid LG100268," *Clin. Cancer Res.*, 14(14):4556-4563, 2008.

Liby, et al., "Synthetic triterpenoids prolong survival in a transgenic mouse model of pancreatic cancer," *Cancer Prevent. Res.*, 3(11):1427-1434, 2010.

Liby, et al., "The rexinoid LG100268 and the synthetic triterpenoid CDDO-methyl amide are more potent than erlotinib for prevention of mouse lung carcinogenesis", *Mol. Cancer Ther.*, 2008, 7:1251-1257.

Liby, et al., "The synthetic triterpenoid CDDO-Me suppresses STAT phosphorylation and induces apoptosis in myeloma and lung cancer cells", *Clinical Cancer Research*, 2006, 12(14 Part 1):4288-4293.

Liby, et al., "The synthetic triterpenoids CDDO and CDDO-imidazole, are potent induces of heme oxygenase-1 and Nrf2/ARE signaling", *Cancer Research*, 2005, 65(11):4789-4798.

Liby, et al., "The synthetic triterpenoids CDDO-Methyl ester and CDDO-ethyl amide prevent lung cancer induced by vinyl carbamate in A/J mice", *Cancer Research*, 2007, 67(6):1-7.

Liby, et al., "Triterpenoids and rexinoids as multifunctional agents for the prevention and treatment of cancer", *Nature Review Cancer*, 2007, 7(5):357-369.

Liby, et al., "Triterpenoids CDDO-methyl ester or CDDO-ethyl amide and rexinoids LG100268 or NRX194204 for prevention and treatment of lung cancer in mice," *Cancer Prev. Res.*, 2(12):1050-1058, 2009.

Ling, et al., "The novel triterpenoid C-28 methyl ester of 2-cyano-3,12-dioxoolen-1,9-dien-28-oic acid inhibits metastatic murine breast tumor tissue growth through inactivation of STAT3 signaling", *Cancer Research*, 2007, 67:4210-4218.

Ling, et al., "The novel triterpenoid C-28 methyl ester of 2-cyano-3,12-dioxoolen-1,9-dien-28-oic acid inhibits metastatic murine breast tumor growth through inactivation of STAT3 signaling," [Erratum to document cited in CA 147:157653], *Cancer Res.*, 68(12):4958, 2008.

Ling, et al., "The novel triterpenoid CDDO-Me inhibits metastatic murine breast tumor through inhibition of STAT3 signaling", 2007 AACR Annual Meeting, Abstract No. 301, 2007.

Liu, et al., "Chemical constituents from root of *Rubus irenaeus*", *Zhongcaoyao*, 2003, 34(5):394-396.

Liu, et al., "Coordinate regulation of enzyme markers for inflammation and for protection against oxidants and electrophiles," *Proc. Natl. Acad. Sci.*, 105(41):15926-15931, 2008.

Liu, et al., "Heme oxygenase-1 (HO-1) inhibits postmyocardial infarct remodeling and restores ventricular function", *FASEB J*, 2006, 20(2):207-216.

Liu, et al., "New lupane-type triterpenoid saponins from leaves of *Oplopanax horridus* (Devil's Club)", *Nat. Prod. Comm.*, 2010, 5(7):1019-1022.

Lu, et al., "Tumor-infiltrating myeloid cells induce tumor cell resistance to cytotoxic T cells in mice", *J. Clin. Invest.*, 2011, 121(10):4015-4029.

Lugemwa, et al., "A heliothis zea antifeedant from the abundant birch bark triterpene botulin", *Journal of Agricultural and Food Chemistry*, 1990, 38(2):493-496.

Marples and Spilling, "Ene reactions of unsaturated acyloins", *Tetrahedron Letters*, 1985, 26(52):6515-6518.

Marples and Spilling, "Facile intramolecular ene reactions of steroidal unsaturated acyloins", *Tetrahedron*, 1992, 48(19):4017-4026.

Marty, et al., "RTA 402 (CDDO-Me) increases survival of mice administered high doses of cytotoxic chemotherapy", *European Organization for Research and Treatment of Cancer, American Association for Cancer Research and National Cancer Institute International Conference*, Nov. 2005, Poster presentation.

Mciver, et al., "NO-mediated alterations in skeletal muscle nutritive blood flow and lactate metabolism in fibromyalgia", *Pain*, 2005, 120(1-2):161-169.

Melichar, et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-γ expression", *Gynecologic Oncology*, 2004, 93:149-154.

Mencherini, et al., "Triterpenoid constituents from the roots of the *Paeonia rockii* ssp. *rockii*", *J. Nat. Prod.*, 2011, 74(10):2116-2121.

Minns, et al., "A novel triterpenoid induces transforming growth factor β production by intraepithelial lymphocytes to prevent ileitis", *Gastroenterology*, 2004, 127:119-126.

Mix, et al., "A synthetic triterpenoid selectively inhibits the induction of matrix metalloproteinases 1 and 13 by inflammatory cytokines", *Arthritis Rheum.*, 2001, 44:1096-1104.

Mix, et al., "Peroxisome proliferator-activated receptor-γ-independent repression of collagenase gene expression by 2-cyano-3,12-dioxooleana-1,9-dien-28-oic acid and prostaglandin 15-deoxy-Δ(12,14) J2: a role in Smad signaling", *Mol. Pharmacol.*, 2004, 65(2):309-318.

Morris, et al., "Association of a functional inducible nitric oxide synthase promoter variant with complications in type 2 diabetes", *J. Mol. Med.*, 80(2):96-104, 2002.

(56) References Cited

OTHER PUBLICATIONS

Morse and Choi, "Heine oxygenase-1: from bench to bedside", *Am. J. Respir. Crit. Care. Med.*, 2005, 172(6):660-670.

Morse and Choi, "Heme oxygenase-1: the 'emerging molecule' has arrived", *Am. J Respir. Crit. Care Med.*, 2002, 27(1):8-16.

Murphy, et al., "Immunomodulatory Effects of the Triterpenoid CDDO after Allogeneic Bone Marrow Transplantation in Mice: Reduction of Acute Graft-Versus-Host Disease Lethality", *Blood*, 2005, 106:1316.

Murray and Zweifel, "Preparation of Phenyl Cyanate and Its Utilization for the Synthesis of α, β-Unsaturated Nitriles", *Synthesis*, 1980, 150-151.

Muzart, "Synthesis of unsaturated carbonyl compounds via chromium-mediated allylic oxidation by 70% tert-butylhydroperoxide", *Tetrahedron Lett.*, 1987, 28:4665-4668.

Nagaraj, et al., "Anti-inflammatory Triterpenoid Blocks Immune Suppressive Function of MDSCs and Improves Immune Response in Cancer," *Clin. Cancer Res.*, 16(6):1812-1823, 2010.

Naik, et al., "Role of oxidative stress in pathophysiology of peripheral neuropathy and modulation by N-acetyl-L-cysteine in rats", *Eur. J. Pain*, 2006, 10(7):573-579.

Nair, et al., "Triterpenes. XLVII. Oxidation rates of triterpenoid secondary alcohols with chromic acid", *Collection of Czechoslovak Chemical Communications*, 1976, 41(3):770-779.

Nanduri, et al., "Biological investigation and structure-activity relationship studies on azadirone from *Azadirachta indica A. juss"*, *Bioorganic and Medicinal Chemistry*, 2003, 13(22):4111-4115.

Nelson, et al., "Oxidative demethylation at C-4 of a steroid via nitroxide photolysis", *J. of the American Chemical Society*, 1975, 97(3):648-649.

Niikura, et al., "The effecs of synthetic triterpenoids on superficial zone protein synthesis in articular chondrocytes", Abstract, Orthopedic Research Society, San Diego, 2007.

Niikura, et al., "The effects of synthetic triterpenoids on szp synthesis in articular chondrocytes", Abstract P197, *Osteoarthritis and Cartilage*, 2006, 14(Suppl B):S112-S113.

Nishimura, et al., "Activity-guided isolation of triterpenoid acyl CoA cholesteryl acyl transferase (ACAT) inhibitors from *Ilex kudincha"*, *J. Nat. Prod.*, 1999, 62(7):1061-1064.

Nishino, et al., "Inhibition of the tumor-promoting action of 12-O tetradecanoylphorbol-13-acetate by some oleanane-type triterpenoid compounds", *Cancer Res.*, 1988, 48:5210-5215.

Notice of Allowance issued in U.S. Appl. No. 14/022,986, dated Nov. 15, 2016.

Office Action in Co-pending U.S. Appl. No. 14/023,180, filed Sep. 10, 2013.

Office Action issued in U.S. Appl. No. 14/022,986, dated May 11, 2016.

Office Action issued in U.S. Appl. No. 14/022,986, dated Mar. 5, 2015.

Office Action issued in U.S. Appl. No. 14/022,986, dated Sep. 15, 2015.

Olsen, et al., "Fatty acid synthesis is a therapeutic target in human liposarcoma," *Int. J. Oncol.*, 36(5):1309-1314, 2010.

Osburn, et al., "Genetic of pharmacologic amplification of Nrf2 signaling inhibits acute inflammatory liver injury in mice", *Toxicology Sciences*, 2008, 104:218-227.

Overnell and Whitehurts, "Reactions of steroid A-ring lactones with Grignard reagents", *J. of the Chemical Society [Section C: Organic]*, 1971, 2:378-384.

Pall, "Nitric oxide synthase partial uncoupling as a key switching mechanism for the NO/ONOO-cycle", *Med. Hypoth.*, 2007, 69(4):821-825.

Pappas, et al., "Photoisomerization of phenalen-1-one oxide. New course of light-induced α,β-epoxy ketone rearrangement", *J. of the American Chemical Society*, 1970, 92(19):5797-5798.

PCT International Search Report and Written Opinion, dated Dec. 4, 2013, for PCT Application PCT/US2013/059027.

Peakman, et al., "Characterization of 24-nor-triterpenoids occurring in sediments and crude oils by comparison with synthesized standards", *Tetrahedron*, 1991, 47(23):3779-3786.

Pedersen, et al., "The triterpenoid CDDO induces apoptosis in refractory CLL B cells", *Blood*, 2002, 100:2965-2972.

Pergola, et al., "Bardoxolone Methyl and Kidney Function in CKD with Type 2 diabetes", *New England Journal of Medicine*, 2011, 365:327-336.

Pitzele, et al., "Synthesis of 2-oxygenated glycyrrhetic acid derivatives", *J. of Medicinal Chemistry*, 1974, 117(2):191-194.

Place, et al., "The novel synthetic triterpenoid, CDDO-imidazolide, inhibits inflammatory response and tumor growth in vivo", *Clin. Cancer Res.*, 2003, 9:2798-2806.

Pradham and Ghosh, "Studies on reactions of 2-bromo-3-ketotriterpenoids: Part IV: Debromination and dehydrobromination of 2α-bromo and 2,2-dibromo derivatives of lupanone and methyl dihydrobetulonate", *Indian J. of Chemistry, Section B: Organic Chemistry Including Medicinal Chemistry*, 1994, 33B(1):73-75.

Rasmusson, et al., "Azasteroids: structure-activity relationships for inhibition of 5 α-reductase and of androgen receptor binding", *J. Med. Chem.*, 1986, 29(11):2298.

Ray, Denise M. et al., "The novel triterpenoid 2-cyano-3,12-dioxooleana-1,9-dien-28-oic acid (CDDO) Induces Apoptosis of Human Diffuse Large B-cell Lymphoma Cells through a Peroxisome Proliferator-activated Receptor γ-independent Pathway", *Experimental Hematology*, 2006, 34:1201-1210.

Reisman, et al., "Topical application of the synthetic triterpenoid RTA 408 protects mice from radiation-induced dermatitis," *Radiation Research Society*, 181(5):512-520, 2014.

Reisman, et al., "Topical application of the synthetic triterpenoid RTA 408 activates Nrf2 and induces cytoprotective genes in rat skin," *Archives of Dermatological Research*, 306(5):447-454, 2014.

Ribo, et al., "Synthesis of methyl 1,11-dioxooleanan-2,12-dien-30-oate and its 24-nor derivative", *Afinidad*, 1981, 38(373):197-200.

Riccioni, et al., "Resistance of acute myeloid leukemic cells to the triterpenoid CDDO-Imidazolide is associated with low caspase-8 and FADD levels," *Leukemia Research*, 32:1244-1258, 2008.

Ross, et al., "Breast cancer biomarkers and molecular medicine", *Expert Rev. Mol. Diagn.*, 2003, 3(5):573-585.

Ross, et al., "HER-2/neu testing in breast cancer", *Am. J. Clin. Pathol.*, 2003, 120( Suppl):S53-71.

Rossi, et al., "Anti-inflammatory cyclopentenone prostaglandins are direct inhibitors of IκB kinase", *Nature*, 2000, 403:103-108.

Rouquette, et al., "A ring-D functionalized nor-triterpenoid of the lupane series as a key intermediate in the formation of widespread hydrocarbon derivatives of higher plant origin in petroleum", *Organic Geochemistry*, 2005, 36(9):1227-1233.

Ruiz, et al., "Targeting the transcription factor Nrf2 to ameliorate oxidative stress and inflammationi in chronic kidney disease," *Kidney Int.*, 83(6):1029-1041, 2013.

Ruster, et al., "Detection of elevated N ε-carboxymethyllysine levels in muscular tissue and in serum of patients with fibromyalgia", *Scand. J Rheumatol.*, 2005, 34(6):460-463.

Ruvolo, et al., "The novel triterpenoid methyl-CDDO inhibits Bc12 phosphorylation and potently kills U937 cells", *Blood*, 1999, 94(10), Suppl. 1, Part 1: 280A, abstract #1251.

Ryu, et al., "Activation of signal transducer and activator of transcription 3 (Stat3) pathway in osteosarcoma cells and overexpression of phosphorylated-Stat3 correlates with poor prognosis," *J. Orthop. Res.*, 28(7):971-978, 2010.

Ryu, et al., "Oleanane triterpenoid CDDO-Me induces apoptosis in multidrug resistant osteosarcoma cells through inhibition of Stat3 pathway," *BMC Cancer*, 10:187, 2010.

Sacerdoti, et al., "Heme oxygenase overexpression attenuates glucose-mediated oxidative stress in quiescent cell phase: linking heme to hyperglycemia complications", *Curr. Neurovasc. Res.*, 2005, 2(2):103-111.

Saha, et al., "The triterpenoid 2-cyano-3,12-dioxooleana-1,9-dien-28-oic acid methyl ester has potent anti-diabetic effects in diet-induced diabetic mice and Lepr$^{db/db}$ mice", *J. Biol. Chem.*, 2010, 285:40581-92.

(56) References Cited

OTHER PUBLICATIONS

Salvemini, et al., "Endogenous ntiric oxide enhances prostaglandin production in a model of renal inflammation", *J. Clin. Invest.*, 1994, 93(5):1940-1947.
Samudio, et al., "2-cyano-3,12-dioxoolean-1,9-diene-28-imidazolide induces apoptosis in pancreatic cancer via redox-dependent cytoplasmic stress", *Proc. Amer. Assoc. Cancer Res.*, 2005, 46:Abstract No. 5899.
Samudio, et al., "2-cyano-3,12-dioxooleana-1,9-dien-28-imidazolide (CDDO-Im) directly targets mitochondrial glutathione to induce apoptosis in pancreatic cancer", *J. Biol. Chem.*, 2005, 280:36273-36282.
Samudio, et al., "A novel mechanism of action of methyl-2-cyano-3,12-dioxoolean-1,9-diene-28-oate (CDDO-Me): Direct permeabilization of the inner mitochondrial membrane to inhibit electron transport and induce apoptosis", *Proc. Am. Assoc. Cancer Res.*, 2006, 47:Abstract #4693.
Samudio, et al., "A novel mechanism of action of methyl-2-cyano-3,12-dioxoolean-1,9-diene-28-oate: direct permeabilization of the inner mitochondrial membrane to inhibit electron transport and induce apoptosis", *Mol. Pharmacol.*, 2006, 69:1182-1193.
Samudio, et al., "Inhibition of mitochondrial metabolism by methyl-2-cyano-3,12-dioxoolean-1,9-diene-28-oate induces apoptotic or autophagic cell death in chronic myelogenous leukemia cells," *Mol. Cancer Ther.*, 7(5):1130-1139, 2008.
Samudio, et al., "The novel triterpenoid CDDOme potently synergizes with inhibition of bcl-2 function to induce apoptosis in AML via disruption of intracellular redox homeostasis", *Proc. Amer. Assoc. Cancer Res.*, 2005, 46:Abstract No. 4955.
Sarchielli, et al., "NF-κB activity and iNOS expression in monocytes from internal jugular blood of migraine without aura patients during attacks", *Cephalalgia*, 2006, 26(9):1071-1079.
Satoh, et al., "Activation of the Keap1/Nrf2 pathway for neuroprotection by electrophillic phase II inducers", *PNAS*, 2006, 103(3):768-773.
Scholtz, et al., "Sensitive and specific methods for the determination of CDDO methyl ester in mouse, rat, dog, monkey, and human plasma by LC-tandem mass spectrometry", *Proc. Amer. Assoc. Cancer Res.*, 2003, 4:Abstract No. 6321.
Schultz, et al., "Nitric oxide, tetrahydrobiopterin, oxidative stress, and endothelial dysfunciton in hypertension", *Antioxid. Redox. Sig.*, 2008, 10(6):1115-1126.
Sejbal, et al., "Triterpenes. Part LXXIII. Reactions of triterpenoid ketones with sulfur and morpholine under Willgerodt-Kindler reaction conditions", *Collection of Czechoslovak Chemical Communications*, 1986, 51(1):118-127.
Sharpless, et al., "Electrophilic and nucleophilic organoselenium reagents. New routes to α,β-unsaturated carbonyl compounds", *J. Am. Chem. Soc.*, 1973, 95:6137.
Shelton, et al., "Role of Nrf2 in protection against acute kidney injury," *Kidney Int.*, 84(6):1090-1095, 2013.
Shin, "Inhibitory roles of Nrf2 and an oleanolic triterpenoid on adipocyte differentiation and obesity", dissertation submitted to John Hopkins University in conformity with the requirements for the degree of Doctor of Philosophy, Mar. 2009.
Shin, et al., "Nrf2 modulates aryl hydrocarbon receptor signaling: influence on adipoogenesis", *Molecular and Cellular Biology*, 2007, 27(20):7188-7197.
Shin, et al., "Role of Nrf2 in prevention of high-fat diet-induced obesity by synthetic triterpenoid CDDO-imidazolide", *Eur. J. Pharmacol.*, 2009, 620(1-3):138-144.
Shishodia, et al., "A synthetic triterpenoid, CDDO-Me, inhibits IκBα kinase and enhances apoptosis induced by THF and chemotherapuetic agents through down-regulation of expression of nuclear factor κB-regulated gene products in human leukemic cells", *Clinical Cancer Research*, 2006, 12(6):1828-1838.
Siddiqui, et al., "Kanerin and 12,13-dihydroursolic acid, two new pentacyclic triterpenes from the leaves of Nerium oleander", *J. Nat. Prod.*, 1989, 52(1):57-62.

Simonsen, et al., "Tetracyclic hydroxy acids", In the Terpenes, Cambridge University, Cambridge, 1957, 5:221-285.
Singh, et al., "Anti-inflammatory activity of oleanolic acid in rats and mice", *J. Pharm. Pharmacol.*, 1992, 44:456-458.
Slides by Reata Pharmaceuticals, "RTA 402, Therapeutic Properties III", podium presentation at BIO 2006 conference, Apr. 9-12, 2006, Chicago, Illinois.
Slides/Handout by Reata Pharma., "RTA 402, Therapeutic Properties I", Private partnering meetings at BioSquare 2006 conference, Mar. 8-10, 2006, Geneva, Switzerland.
Slides/Handout by Reata Pharma., "RTA 402, Therapeutic Properties II", Private partnering meetings at BIO 2006 conference, Apr. 9-12, 2006, Chicago, Illinois.
Slides/Handout by Reata Pharma., "RTA 402, Therapeutic Properties IV", Private partnering meetings at BioPartnering Europe 2006 conference, Oct. 8-10, 2006, London, England.
Slides/Handout by Reata Pharma., "RTA 402, Therapeutic Properties IX", Private partnering meeting at BIO Europe 2007 conference, Nov. 12-14, 2007, Hamburg, Germany.
Slides/Handout by Reata Pharma., "RTA 402, Therapeutic Properties V", Private partnering meetings at BIO 2007 conference, May 6-9, 2007, Boston, Massachusetts.
Slides/Handout by Reata Pharma., "RTA 402, Therapeutic Properties VI", Private partnering meetings at BIO 2007 conference, May 6-9, 2007, Boston, Massachusetts.
Slides/Handout by Reata Pharma., "RTA 402, Therapeutic Properties VII", Podium presentation at BIO 2007 conference, May 6-9, 2007, Boston, Massachusetts.
Slides/Handout by Reata Pharma., "RTA 402, Therapeutic Properties VIII", Private partnering meetings at BIO Europe 2007 conference, Nov. 12-14, 2007, Hamburg, Germany.
Sporn and Roberts, "Peptide growth factors and inflammation, tissue repair, and cancer", *J. Clin. Invest.*, 1986, 78:329-332.
Sporn, et al., "New synthetic triterpenoids: potent agents for prevention and treatment of tissue injury caused by inflammation and oxidative stress," *J. Nat. Prod.*, 74:537-545, 2011.
Sporn, et al., "Prospects for prevention and treatment of cancer with selective PPARγ modulators (SPARMs)", *Trends in Molecular Medicine*, 2001, 7(9):395-400.
Stadheim, et al., "The novel triterpenoid 2-cyano-3,12-dioxooleana-1,9-dien-28-oic acid (CDDO) potently enhances apoptosis induced by tumor necrosis factor in human leukemia cells", *J. Biol. Chem*, 2002, 277:16448-16455.
Subba Rao, et al., "Chemical modifications of natural triterpenes—glycyrrhetinic and boswellic acids: evaluation of their biological activity," *Tetrahedron*, 64(51):11541-11548, 2008.
Suh, et al., "A novel synthetic oleanane triterpenoid, 2-cyano-3,12-dioxoolean-1,9-dien-28-oic acid (CDDO), induces cell differentiation in human myeloid leukemias", Proceedings of the American Association for Cancer Research Annual Meeting, 40:300 abstract.
Suh, et al., "A novel synthetic oleanane triterpenoid, 2-cyano-3,12-dioxoolean-1,9-dien-28-oic acid, with potent differentiating, antiproliferative, and anti-inflammatory activity", *Cancer Res.*, 1999, 59(2):336-341.
Suh, et al., "New triterpenoids as cancer preventive and anti-inflammatory agents", *Proceedings of the American Association for Cancer Research*, 1997, Abstract No. 1457, 38:216.
Suh, et al., "Novel triterpenoids suppress inducible nitric oxide synthase (iNOS) and inducible cyclooxygenase (COX-2)", Proceedings of the American Association for Cancer Research Annual Meeting, 1998, 39:Abstract No. 1821.
Suh, et al., "Novel triterpenoids suppress inducible nitric oxide synthase (iNOS) and inducible cyclooxygenase (COX-2) in mouse macrophages", *Cancer Res.*, 1998, 58:717-723.
Suh, et al., "Synthetic triterpenoids activate a pathway for apoptosis in AML cells involving downregulation of FLIP and sensitization to TRAIL", *Leukemia*, 2003, 17:2122-2129.
Suh, et al., "Synthetic triterpenoids enhance transforming growth factor β/SMAD signaling", *Cancer Res.*, 2003, 63:1371-1376.
Suh, et al., "Triterpenoids CDDO and CDDO-Me Down-Regulate FLIP Expression and Sensitize AML cells to Trail-Induced Apoptosis", American Society of Hematology 43rd Annual Meeting and Exposition, 2001, Abstract No. 498.

(56) References Cited

OTHER PUBLICATIONS

Sultana, et al., "Phytochemical studies on *Alstonia scholaris*", *Zeitschrift für Naturforschung B, A Journal of Chemical Sciences*, 2010, 65(2):203-210.

Sun, et al., "Structure-activity relationships of olean- and ursane-type triterpenoids", *Botanical Studies*, 2006, 47:339-368.

Sun, et al., "The synthetic triterpenoid, CDDO, suppresses alloreactive T cell responses and reduces murine early acute graft-versus-host disease mortality", *Biology of Blood and Marrow Transplantation*, 2007, 13(5):521-529.

Sun, et al., "Therapeutic potential of synthetic triterpenoids in neuroblastoma," *Cancer Biology & Therapy*, 7(5):720-722, 2008.

Sussan, et al., "Targeting Nrf2 with the triterpenoid CDDO-imidazolide attenuate cigarette smoke-induced emphysema and cardiac dysfunction in mice", *Proc. Nat. Sci. Acad. USA*, 2009, 106:250-255.

Szabo, et al., "Peroxynitrite: Biochemistry, Pathophysiology, and Development of Therapeutics", *Nature Rev. Drug Disc.*, 2007, 6:662-680.

Tabe, et al., "Chromatin-Mediated Transcriptional Activation with Novel Peroxisome Proliferator-Activated Receptor gamma(PPARγ) Ligand 2-cyano-1,9-dien-28-oic acid (CDDO) in Acute Promyelocytic leukemia cells", Abstracts of the 44th Annual Meeting of the American Society of Hematology.

Takahashi, et al., "Increased expression of inducible and endothelial constitutive nitric oxide synthases in rat colon tumors induced by azoxymethane", *Cancer Res.*, 1997, 57:1233-1237.

Takaishi, et al., "Triterpenoid inhibitors of interleukin-1 secretion and tumor-promotion from *Tripterygium wilfordii* var. *regelii*", *Phytochemistry*, 1997, 45(5):969-974.

Tamir and Tannebaum, "The role of nitric oxide (NO) in the carcinogenic process", *Biochim. Biophys. Acta*, 1996, 1288:F31-F36.

Tanaka, et al., "A new triterpenoid from the leaves of *Eucommia ulmoides Oliv.*", *Chem. Pharm. Bull (Tokyo)*, 1997, 45(8):1379-1380.

Ten Haven, et al., "Early diagenetic transformation of higher-plant triterpenoids in deep-sea sediments from Baffin Bay", *Geochimicha et Cosmochimica Acta*, 1992, 56(5):2001-2024.

Thimmulappa, et al., "Nrf2 is a critical regulator of the innate immune response and survival during experimental sepsis", *J. Clinical Investigations*, 2006, 116(4):984-995.

Thimmulappa, et al., "Nrf2-dependent protection from LPS induced inflammatory response and mortality by CDDO-imidazole", *Biochem. Biophys. Res. Commun.*, 2006, 351:883-889.

Thimmulappa, et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils", *Antioxidants & Redox Signaling*, 2007, 9(11):1-8.

To, et al., "Synthetic Triterpenoids Target the Arp2/3 Complex and Inhibit Branched Actin Polymerization," *J. Biol. Chem.*, 285(36):27944-27957, 2010.

To, et al., "The synthetic triterpenoid 2-cyano-3,12-dioxooleana-1,9-dien-28-oic acid-imidazolide alters transforming growth factor β-dependent signaling and cell migration by affecting the cytoskeleton and the polarity complex," *J. Biol. Chem.*, 283:11700-11713, 2008.

Tran, et al., "The synthetic triterpenoid CDDO-methyl ester modulates microglial activities, inhibits TNF production, and provides dopaminergic neuroprotection", *Journal of Neuroinflammation*, 2008, 5:1-14.

Tsao, et al., "DRIP205 co-activator overexpression enhances PPARγ-mediated differentiation of leukemia cells by CDDO", *Proc. Amer. Assoc. Cancer Res.*, 2005, 46:Abstract No. 1855.

Tsao, et al., "Targeted Induction of Apoptosis in Leukemias by PPARgamma Ligation", American Society of Hematology 43rd Annual Meeting and Exposition, 2001, Abstract No. 2381.

Urban, et al., "Influence of esterification and modification of A-ring in a group of lupane acids on their cytotoxicity", *Bioorganic and Medicinal Chemistry*, 2005, 13(19):5527-5535.

Urban, et al., "Synthesis of A-seco derivatives of betulinic acid with cytotoxic activity", *J. of Natural Products*, 2004, 67(7):1100-1105.

Uskoković, et al., "D-Homosteroids. I. 3β-hydroxy-17a,17a-dimethyl-D-homoandrostane-17-one and related compounds", *J. of the American Chemical Society*, 1959, 81:4561-4566.

Van Kiem, et al., "A new 24-nor-lupane-gylcoside of *Acanthopanax trifoliatus*", *Arch. Pharm. Res.*, 2003, 26(9):706-708.

Vannini, et al., "The synthetic oleanane triterpenoid, CDDO-methyl ester, is a potent antiangiogenic agent", *Molecular Cancer Therapeutics*, 2007, 6(12 Part 1):3139-3146.

Venè, et al., "Glycogen synthase kinase 3β regulates cell death induced by synthetic triterpenoids," *Cancer Res.*, 68:6987-6996, 2008.

Vilayur and Harris, "Emerging therapies for chronic kidney disease: what is their role?", *Nature Reviews*, 2009, 5:375-383.

Vincenti, et al., "The synthetic triterpenoid TP-222 inhibits RANKL induction of differentiation and MMP-9 gene expression in osteoclasts", Abstract 1385, American College of Rheumatology Annual Scientific Meeting, 2006.

Wada and Tanaka, "Synthetic lanostane-type triterpenoids as inhibitors of DNA topoisomerase II", *Bioorganic and Medicinal Chemistry Letters*, 2005, 15(12):2966-2969.

Wang, "Differentiating and anti-inflammatory activities of the triterpenoid, CDDO," Thesis, Dartmouth College, May 4, 2001.

Wang, et al., "A novel synthetic triterpenoid, 2-cyano-3,12-dioxoolean-1,9-dien-28-oic acid (CDDO) induces adipocyte differentiation in 3T3-L1 cells", Proceedings of the American Association for Cancer Research Annual Meeting, 1999, 40:300 abstract No. 1989.

Wang, et al., "A synthetic triterpenoid, 2-cyano-3,12-dioxooleana-1,9-dien-28-oic acid (CDDO), is a ligand for the peroxisome proliferator-activated receptor γ", *Mol. Endocrin.*, 2000, 14(10):1550-1556.

Wang, et al., "Synthetic triterpenoid CDDO and its derivatives increase ceramides and are cytotoxic to pediatric acute lymphoblastic leukemia cell lines", *Proc. Am. Assoc. Cancer Res.*, 2006, 47:4643.

Waratchareeyakul, et al., "2,19-dihydroxy-3-oxo-(2,4,19)-24-nor-olean-12-en-28-oic acid monohydrate", *Acta. Cryst.*, 2007, E63, o4062-o4063.

Wen, et al., "Naturally occurring pentacyclic triterpenes as inhibitors of glycogen phosphorylase: synthesis, structure-activity relationships, and X-ray crystallographic studies," *J. Med. Chem.*, 51:3540-3554, 2008.

Wen, et al., "Pentacyclic triterpenes. Part 2: Synthesis and Biological evaluation of maslinic acid derivatives as glycogen phosphorylase inhibitors", *Bioorganic and Medicinal Chemistry Letters*, 2006, 16(3):722-726.

White, et al., "A novel demethylated oxygenated triterpenoid in crude oils from the Canadian Beaufort sea and northeast Alaska", *Tetrahedron Letters*, 1998, 39(19):3031-3034.

Wu, et al., "Beneficial role of Nrf2 in regulating NADPH generation and consumption", *Toxicological Sciences*, 2011, 123(2):590-600.

Xing, et al., "Triterpenoid dihydro-CDDO-trifluoroethyl amide protects against maladaptive cardiac remodeling and dysfunction in mice: a crucial role of Nrf2", *PLoS One*, 2012, 7:344899.

Xu, et al., "Inhibition of the signal transducer and activator of transcription-3 (STAT3) signaling pathway by 4-oxo-1-phenyl-1,4-dihydroquinoline-3-carboxylic acid esters," *J. Med. Chem.*, 51:4115-4121, 2008.

Yates, et al., "Pharmacodynamic characterization of chemopreventive triterpenoids as exceptionally potent inducers of Nrf2-regulated genes", *Mol. Cancer Ther.*, 2007, 6:154-162.

Yates, et al., "Potent protection against aflatoxin-induced tumorigenesis through induction of Nrf2-regulated pathways by the triterpenoid 1-[2-cyano-3,12-dioxooleana-1,9(11)-dien-28-oyl]imidazole", *Cancer Res.*, 2007, 66(4):2488-2494.

Yore, et al., "The synthetic triterpenoid 1-[2-cyano-3,12-dioxooleana-1,9(11)-dien-28-oyl]imidazole blocks nuclear factor-κB activation through direct inhibition of IκB kinase β", *Mol. Cancer Ther.*, 2006, 5(12):3232-3239.

(56) References Cited

OTHER PUBLICATIONS

You, et al., "Synthesis and cytotoxic activity of a-ring modified betulinic acid derivatives", *Bioorganic and Medicinal Chemistry Letters*, 2003, 13(19):3137-3140.

Yue, et al., "Depletion of intracellular glutathione contributes to JNK-mediated death receptor 5 upregulation and apoptosis induction by the novel synthetic triterpenoid methyl-2-cyano-3,12-dioxooleana-1,9-dien-28-oate (CDDO-Me)", *Cancer & Biology Therapy*, 2006, 5(5):492-497.

Zapata, et al., "CDDO and CDDO-Im reduce tumor burden in a transgenic mouse model of CLL", *Blood*, 2004, 104:3477.

Zapata, et al., "Trterpenoids show activity against leukemic cells in a transgenic mouse model of CLL", *Proc. Amer. Assoc. Cancer Res.*, 2005, 46:Abstract No. 5179.

Zhang, et al., "Synthetic triterpenoid CDDO as effective therapy for HER2-expressing resistant breast cancer", *Proc. Amer. Assoc. Cancer Res.*, 2004, Abstract No. 3799.

Zhang, et al., "The activation of p38 and JNK by ROS, contribute to OLO-2-mediated intrinsic apoptosis in human hepatocellular carcinoma cells," *Food and Chemical Toxicology*, 63:38-47, 2014.

Zhang, et al., "The novel synthetic oleanane triterpenoid CDDO (2-cyano-3,12-dioxoolean-1,9-dien-28-oic acid) induces apoptosis in *Mycosis fungoides*/Sézary syndrome cells", *J. Invest. Dermatol.*, 2004, 123:380-387.

Zhou, et al., "A new triterpenoid from the roots of *Tripterygium wildfordii*", *Chinese Chemical Letters*, 2010, 21(5):600-602.

Zhou, et al., "Carbon Monoxide Suppresses Bleomycin-induced Lung Fibrosis", *Am. J. Pathol.*, 2005, 166(1):27-37.

Ziegler, et al., "Isolation and structure of eucosterol and 16β-hydroxyeucosterol, two novel spirocyclic nortriterpenes, and of a new 24-nor-5α-chola-8,16-diene-23-oic acid from bulbs of several *Eucomis* species", *Helv. Chim. Acta*, 1976, 59(6):1997-2011.

Zou, et al., "c-FLIP downregulation contributes to apoptosis induction by the novel synthetic triterpenoid methyl-2-cyano-3,12-dioxooleana-1,9-dien-28-oate (CDDO-Me) in human lung cancer cells," *Cancer Biology & Therapy*, 6(10):1614-1620, 2007.

Zou, et al., "c-Jun NH2-terminal kinase-mediated up-regulation of death receptor 5 contributes to induction of apoptosis by the novel synthetic triterpenoid methyl-2-cyano-3,12-dioxooleana-1,9-dien-28-oate in human lung cancer cells", *Cancer Res.*, 2004, 64:7570.

Zou, et al., "Coupling of endoplasmic reticulum stress to CDDO-Me-induced up-regulation of death receptor 5 via a CHOP-dependent mechanism involving JNK activation," *Cancer Res.*, 68:7484-7492, 2008.

* cited by examiner

SEQUENCE LISTING

```
<160> NUMBER OF SEQ ID NOS: 1

<210> SEQ ID NO 1
<211> LENGTH: 26
<212> TYPE: DNA
<213> ORGANISM: Artificial Sequence
<220> FEATURE:
<223> OTHER INFORMATION: Synthetic primer

<400> SEQUENCE: 1
cagtcacagt gactcagcag aatctg                                        26
```

C17-ALKANEDIYL AND ALKENEDIYL DERIVATIVES OF OLEANOLIC ACID AND METHODS OF USE THEREOF

This application is a divisional of U.S. patent application Ser. No. 14/022,986, filed on Sep. 10, 2013, which claims the benefit of both U.S. Provisional Patent Application No. 61/699,122, filed on Sep. 10, 2012, and U.S. Provisional Patent Application No. 61/780,540, filed on Mar. 13, 2013, the entirety of each are incorporated herein by reference.

Pursuant to 37 C.F.R. 1.821(c), a sequence listing is submitted herewith as an ASCII compliant text file named "REATP0074USD1_ST25.txt", created on Feb. 2, 2017 and having a size of ~1 KB. The content of the aforementioned file is hereby incorporated by reference in its entirety.

BACKGROUND OF THE INVENTION

I. Field of the Invention

The present invention relates generally to the fields of biology and medicine. More particularly, it concerns compounds, compositions and methods for the treatment and prevention of diseases such as those associated with oxidative stress and inflammation.

II. Description of Related Art

The anti-inflammatory and anti-proliferative activity of the naturally occurring triterpenoid, oleanolic acid, has been improved by chemical modifications. For example, 2-cyano-3,12-dioxooleana-1,9(11)-dien-28-oic acid (CDDO) and related compounds have been developed (Honda et al., 1997; Honda et al., 1998; Honda et al., 1999; Honda et al., 2000a; Honda et al., 2000b; Honda, et al., 2002; Suh et al. 1998; Suh et al., 1999; Place et al., 2003; Liby et al., 2005; and U.S. Pat. Nos. 8,129,429; 7,915,402; 8,124,799; 8,071,632; 8,338,618; and 7,943,778). The methyl ester, bardoxolone methyl (CDDO-Me), has been evaluated clinically for the treatment of cancer and chronic kidney disease (Pergola et al., 2011; Hong et al., 2012).

Synthetic triterpenoid analogs of oleanolic acid have also been shown to be inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002). Synthetic derivatives of another triterpenoid, betulinic acid, have also been shown to inhibit cellular inflammatory processes, although these compounds have been less extensively characterized (Honda et al., 2006). The pharmacology of these synthetic triterpenoid molecules is complex. Compounds derived from oleanolic acid have been shown to affect the function of multiple protein targets and thereby modulate the activity of several important cellular signaling pathways related to oxidative stress, cell cycle control, and inflammation (e.g., Dinkova-Kostova et al., 2005; Ahmad et al., 2006; Ahmad et al., 2008; Liby et al., 2007a). Derivatives of betulinic acid, though they have shown comparable anti-inflammatory properties, also appear to have significant differences in their pharmacology compared to OA-derived compounds (Liby et al., 2007b). Given that the biological activity profiles of known triterpenoid derivatives vary, and in view of the wide variety of diseases that may be treated or prevented with compounds having potent antioxidant and anti-inflammatory effects, and the high degree of unmet medical need represented within this variety of diseases, it is desirable to synthesize new compounds with diverse structures that may have improved biological activity profiles for the treatment of one or more indications.

SUMMARY OF THE INVENTION

The present disclosure provides novel synthetic triterpenoid derivatives, with anti-inflammatory and/or antioxidant properties, pharmaceutical compositions, and methods for their manufacture, and methods for their use.

In one aspect, there are provided compounds of the formula:

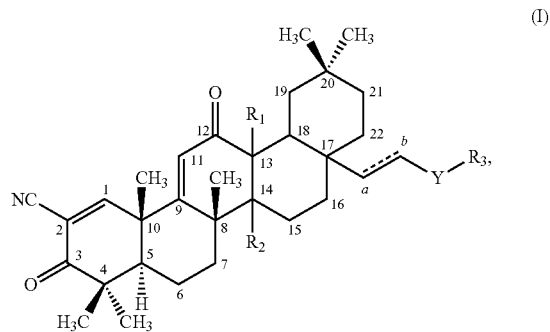

wherein:
Y is a covalent bond, —CH$_2$—, —C(O)—, —O—, or —NH—;
R$_1$ and R$_2$ are each independently —H, —OH, methyl, or as defined below; and
R$_3$ is:
hydrogen, hydroxy, halo, amino, —NHOH, or mercapto; alkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, acyl$_{(C\leq 8)}$, alkoxy$_{(C\leq 8)}$, alkenyloxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, heterocycloalkoxy$_{(C\leq 8)}$, alkylamino$_{(C\leq 8)}$, dialkylamino$_{(C\leq 8)}$, alkenylamino$_{(C\leq 8)}$, alkoxyamino$_{(C\leq 8)}$, arylamino$_{(C\leq 8)}$, aralkylamino$_{(C\leq 8)}$, heteroarylamino$_{(C\leq 8)}$, heterocycloalkylamino$_{(C\leq 8)}$, alkylsulfonylamino$_{(C\leq 8)}$, amido$_{(C\leq 8)}$, —NH-amido$_{(C\leq 8)}$, or a substituted version of any of these groups;
R$_3$ and R$_1$, taken together, are —O—, —NR$_a$— or a covalent bond between Y and carbon atom 13, wherein R$_a$ is hydrogen or alkyl$_{(C\leq 4)}$; or
R$_3$ and R$_2$, taken together, are —O—, —NR$_a$— or a covalent bond between Y and carbon atom 14, wherein R$_a$ is hydrogen or alkyl$_{(C\leq 4)}$;
or a pharmaceutically acceptable salt thereof.

In some embodiments, the compounds are further defined as:

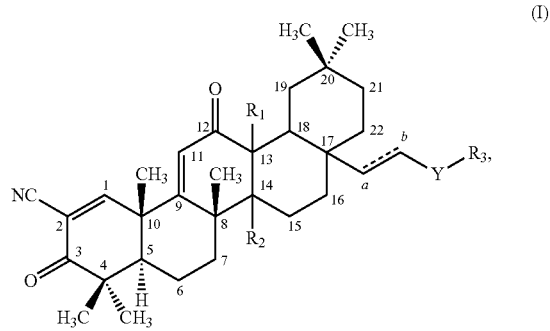

wherein:

Y is —CH$_2$—, —C(O)—, —O—, or —NH—;

R$_1$ and R$_2$ are each independently —H, —OH, methyl, or as defined below; and R$_3$ is:

hydrogen, hydroxy, halo, amino, —NHOH, or mercapto;

alkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, acyl$_{(C\leq 8)}$, alkoxy$_{(C\leq 8)}$, alkenyloxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, heterocycloalkoxy$_{(C\leq 8)}$, alkylamino$_{(C\leq 8)}$, dialkylamino$_{(C\leq 8)}$, alkenylamino$_{(C\leq 8)}$, alkoxyamino$_{(C\leq 8)}$, arylamino$_{(C\leq 8)}$, aralkylamino$_{(C\leq 8)}$, heteroarylamino$_{(C\leq 8)}$, heterocycloalkylamino$_{(C\leq 8)}$, alkylsulfonylamino$_{(C\leq 8)}$, amido$_{(C\leq 8)}$, —NH-amido$_{(C\leq 8)}$, or a substituted version of any of these groups;

R$_3$ and R$_1$, taken together, are —O—, —NR$_a$— or a covalent bond between Y and carbon atom 13, wherein R$_a$ is hydrogen or alkyl$_{(C\leq 4)}$; or R$_3$ and R$_2$, taken together, are —O—, —NR$_a$— or a covalent bond between Y and carbon atom 14, wherein R$_a$ is hydrogen or alkyl$_{(C\leq 4)}$;

or a pharmaceutically acceptable salt thereof.

In some embodiments, the compounds are further defined as:

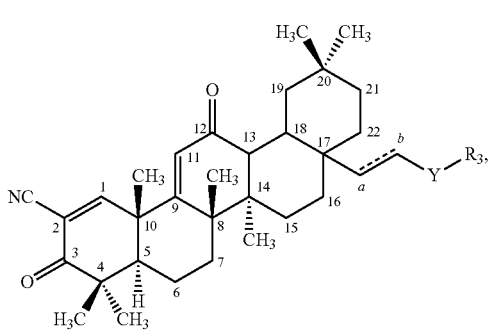

(II)

wherein:

Y is a covalent bond, —CH$_2$—, —C(O)—, —O—, or —NH—; and

R$_3$ is:

hydrogen, hydroxy, halo, amino, —NHOH, or mercapto; or alkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, acyl$_{(C\leq 8)}$, alkoxy$_{(C\leq 8)}$, alkenyloxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, heterocycloalkoxy$_{(C\leq 8)}$, alkylamino$_{(C\leq 8)}$, dialkylamino$_{(C\leq 8)}$, alkenylamino$_{(C\leq 8)}$, alkoxyamino$_{(C\leq 8)}$, arylamino$_{(C\leq 8)}$, aralkylamino$_{(C\leq 8)}$, heteroarylamino$_{(C\leq 8)}$, heterocycloalkylamino$_{(C\leq 8)}$, alkylsulfonylamino$_{(C\leq 8)}$, amido$_{(C\leq 8)}$, —NH-amido$_{(C\leq 8)}$, or a substituted version of any of these groups;

or a pharmaceutically acceptable salt thereof.

In some embodiments, the compounds are further defined as:

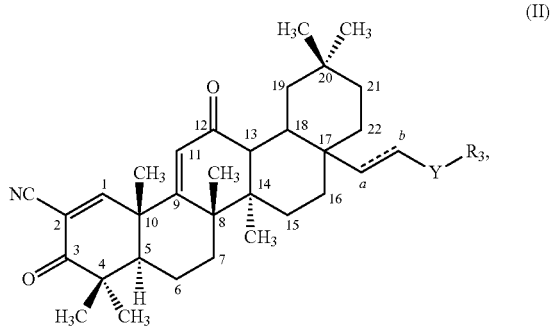

(II)

wherein:

Y is —CH$_2$—, —C(O)—, —O—, or —NH—; and

R$_3$ is:

hydrogen, hydroxy, halo, amino, —NHOH, or mercapto; or alkyl$_{(C\leq 8)}$, alkenyl$_{(C\leq 8)}$, alkynyl$_{(C\leq 8)}$, aryl$_{(C\leq 8)}$, aralkyl$_{(C\leq 8)}$, heteroaryl$_{(C\leq 8)}$, heterocycloalkyl$_{(C\leq 8)}$, acyl$_{(C\leq 8)}$, alkoxy$_{(C\leq 8)}$, alkenyloxy$_{(C\leq 8)}$, aryloxy$_{(C\leq 8)}$, aralkoxy$_{(C\leq 8)}$, heteroaryloxy$_{(C\leq 8)}$, acyloxy$_{(C\leq 8)}$, heterocycloalkoxy$_{(C\leq 8)}$, alkylamino$_{(C\leq 8)}$, dialkylamino$_{(C\leq 8)}$, alkenylamino$_{(C\leq 8)}$, alkoxyamino$_{(C\leq 8)}$, arylamino$_{(C\leq 8)}$, aralkylamino$_{(C\leq 8)}$, heteroarylamino$_{(C\leq 8)}$, heterocycloalkylamino$_{(C\leq 8)}$, alkylsulfonylamino$_{(C\leq 8)}$, amido$_{(C\leq 8)}$, —NH-amido$_{(C\leq 8)}$, or a substituted version of any of these groups;

or a pharmaceutically acceptable salt thereof.

In some embodiments, the bond between carbon atoms a and b is a single bond. In some embodiments, the bond between carbon atoms a and b is a double bond. In some embodiments, Y is a covalent bond. In some embodiments, Y is —CH$_2$—. In some embodiments, Y is —C(O)—. In some embodiments, Y is —O—. In some embodiments, R$_1$ is —H. In some embodiments, R$_2$ is methyl.

In some embodiments, R$_3$ is —H. In some embodiments, R$_3$ is —OH. In some embodiments, R$_3$ is amino. In some embodiments, R$_3$ is alkyl$_{(C\leq 8)}$, for example methyl. In some embodiments, R$_3$ is heterocycloalkyl$_{(C\leq 8)}$, for example, morpholinyl, pyrrolidinyl, azetidinyl or piperazinyl. In some embodiments, R$_3$ is substituted heterocycloalkyl$_{(C\leq 8)}$, for example, hydroxypyrrolidinyl, difluoropyrrolidinyl, hydroxypiperidinyl, or N-Boc-piperazinyl. In some embodiments, R$_3$ is acyl$_{(C\leq 8)}$, for example, acetyl. In some embodiments, R$_3$ is substituted acyl$_{(C\leq 8)}$, for example, ethylaminocarbonyl. In some embodiments, R$_3$ is alkoxy$_{(C\leq 8)}$, for example, methoxy, ethoxy, isopropoxy, tert-butoxy, or —O-cyclohexyl. In some embodiments, R$_3$ is aryloxy$_{(C\leq 8)}$, for example, —O-phenyl. In some embodiments, R$_3$ is aralkoxy$_{(C\leq 8)}$, for example, benzyloxy. In some embodiments, R$_3$ is substituted acyloxy$_{(C\leq 8)}$, for example, —OC(O)NHCH$_2$CH$_3$. In some embodiments, R$_3$ is heterocycloalkoxy$_{(C\leq 8)}$, for example, —O-piperidinyl or N-Boc-piperidinyloxy. In some embodiments, R$_3$ is alkylamino$_{(C\leq 8)}$, for example, methylamino, ethylamino, isopropylamino, tert-butylamino or cyclohexylamino. In some embodiments, R$_3$ is substituted alkylamino$_{(C\leq 8)}$, for example, 2,2,2-trifluoroethylamino, —NHCH$_2$C(O)OCH$_3$ or —NHCH$_2$C(O)OH. In some embodiments, R$_3$ is dialkylamino$_{(C\leq 8)}$, for example, dimethylamino. In some embodiments, R$_3$ is alkoxyamino$_{(C\leq 8)}$, for example, methoxyamino. In some embodiments, R$_3$ is arylamino$_{(C\leq 8)}$, for example, phenylamino. In some embodiments, R$_3$ is aralkylamino$_{(C\leq 8)}$, for example, benzylamino. In some embodiments, $R_3$ is heteroarylamino$_{(C \leq 8)}$, for example, pyridinylamino. In some embodiments, $R_3$ is heterocycloalkylamino$_{(C \leq 8)}$, for example, oxetanylamino. In some embodiments, $R_3$ is —NH-amido$_{(C \leq 8)}$, for example, —NHNHC(O)CH$_3$.
In some embodiments, the compounds are selected from the groups comprising:
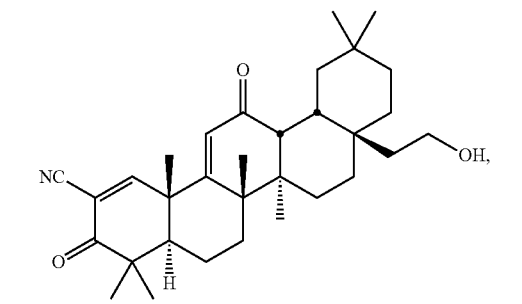
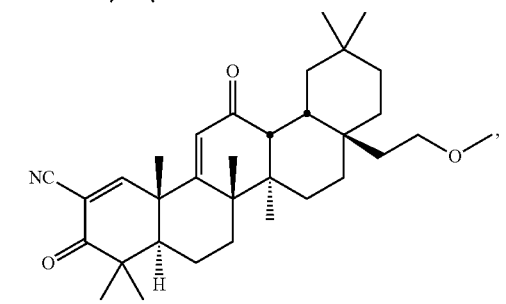
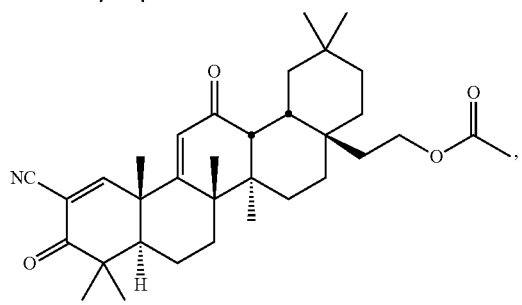
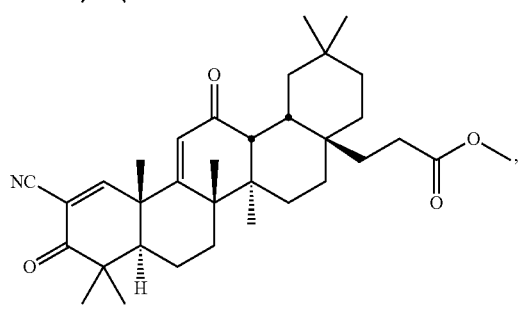
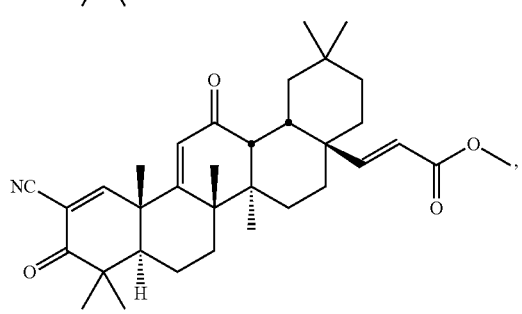
-continued
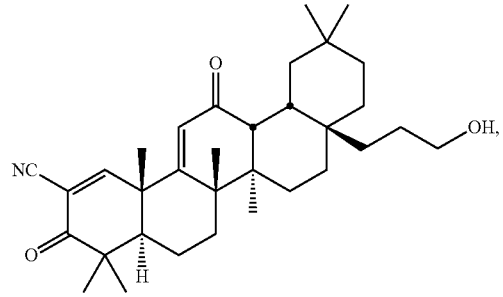
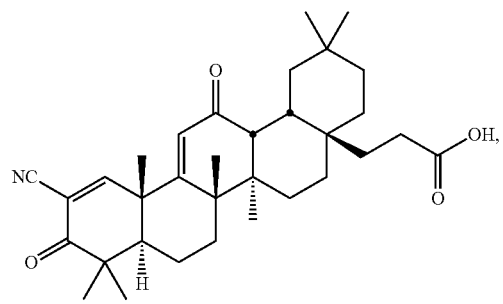
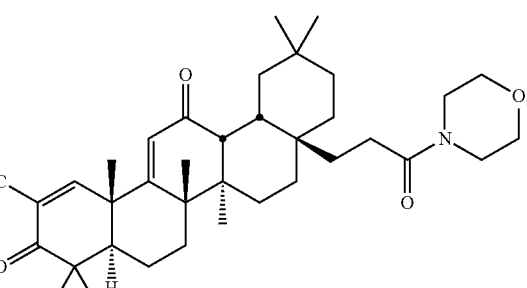
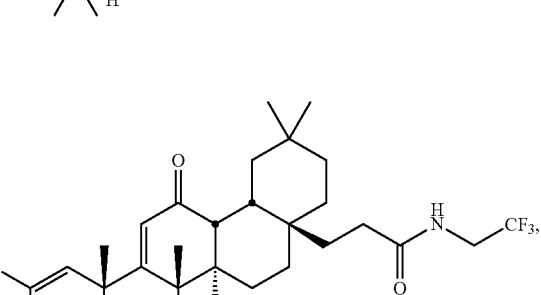
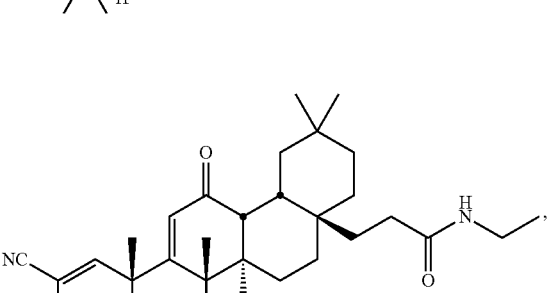

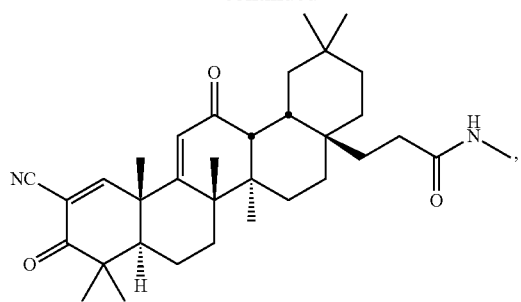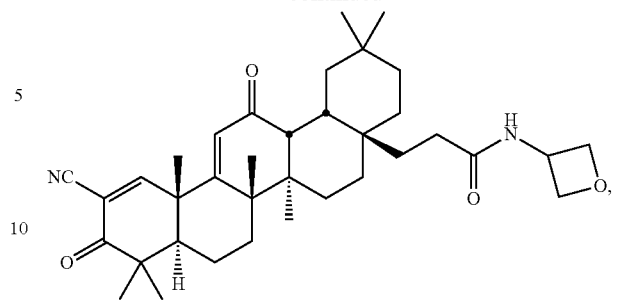

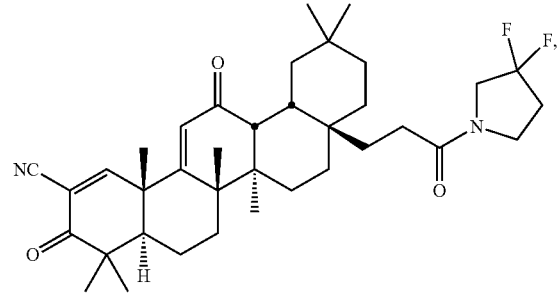
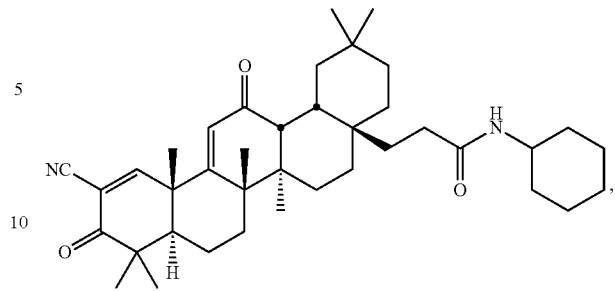
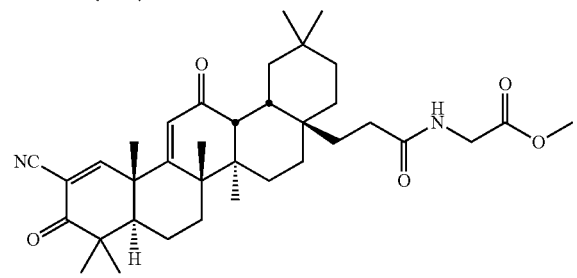
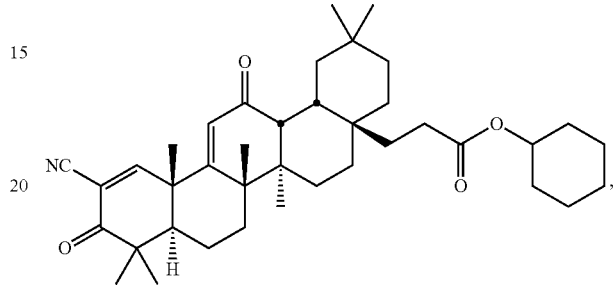
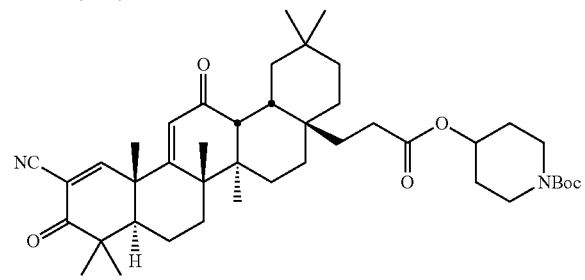
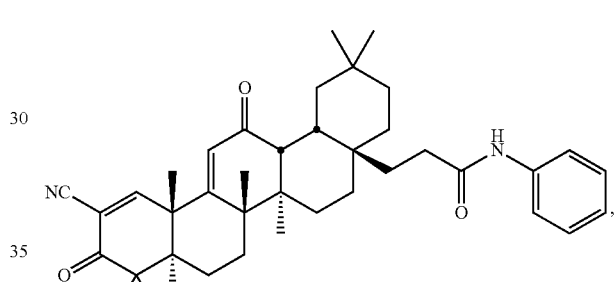
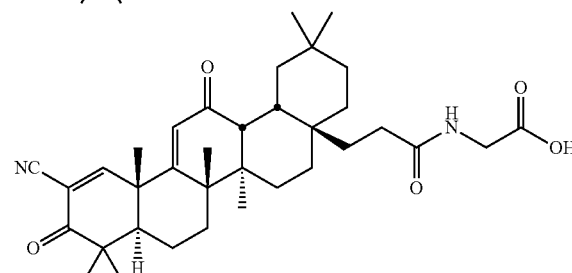
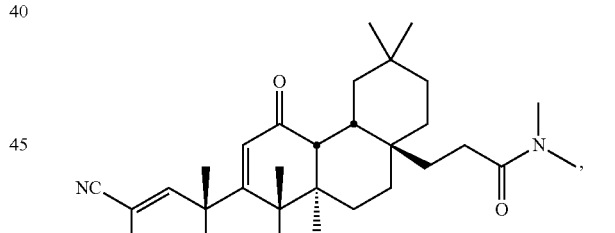
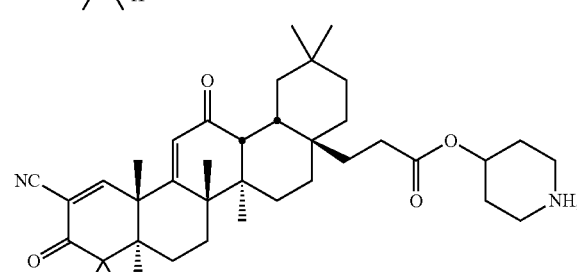
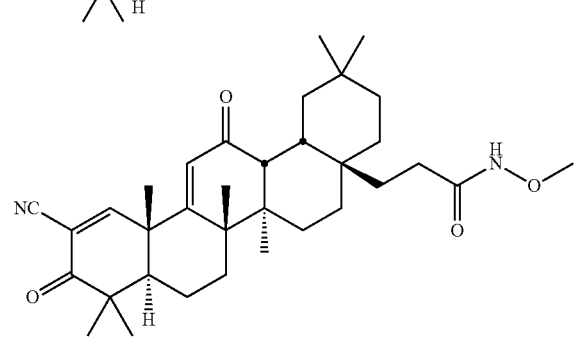
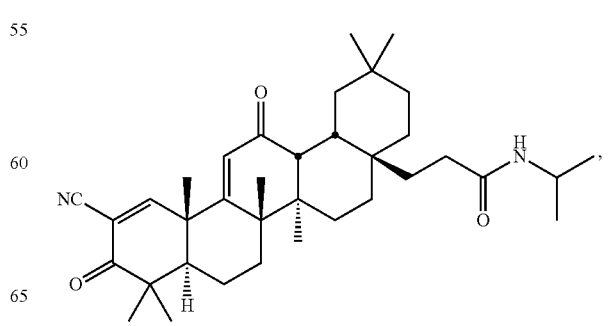

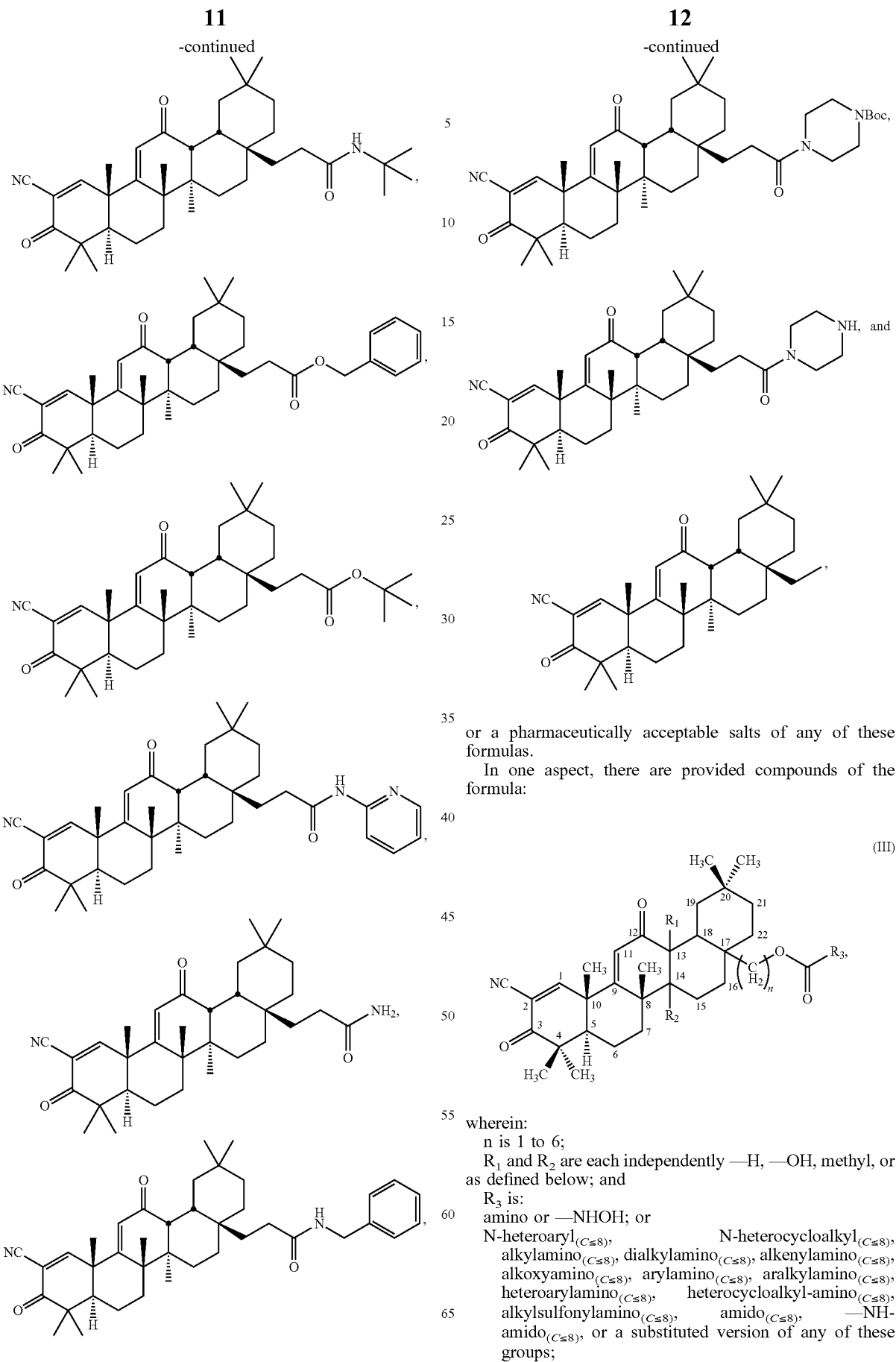

or a pharmaceutically acceptable salts of any of these formulas.

In one aspect, there are provided compounds of the formula:

wherein:
n is 1 to 6;
$R_1$ and $R_2$ are each independently —H, —OH, methyl, or as defined below; and
$R_3$ is:
amino or —NHOH; or
N-heteroaryl$_{(C≤8)}$, N-heterocycloalkyl$_{(C≤8)}$, alkylamino$_{(C≤8)}$, dialkylamino$_{(C≤8)}$, alkenylamino$_{(C≤8)}$, alkoxyamino$_{(C≤8)}$, arylamino$_{(C≤8)}$, aralkylamino$_{(C≤8)}$, heteroarylamino$_{(C≤8)}$, heterocycloalkyl-amino$_{(C≤8)}$, alkylsulfonylamino$_{(C≤8)}$, amido$_{(C≤8)}$, —NH-amido$_{(C≤8)}$, or a substituted version of any of these groups;

R$_3$ and R$_1$, taken together, are —NR$_a$—, wherein R$_a$ is hydrogen or alkyl$_{(C \leq 4)}$; or R$_3$ and R$_2$, taken together, are —NR$_a$—, wherein R$_a$ is hydrogen or alkyl$_{(C \leq 4)}$; or or a pharmaceutically acceptable salt thereof.

In some embodiments, the compounds are further defined as:

(IV)

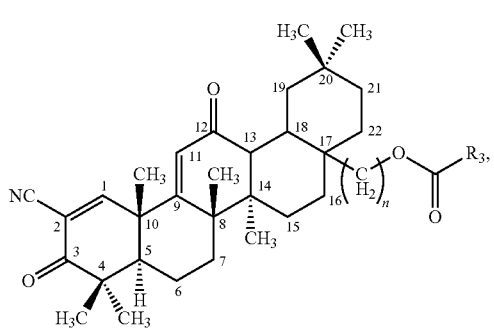

wherein:

n is 1 to 6; and

R$_3$ is:

amino or —NHOH; or

N-heteroaryl$_{(C \leq 8)}$, N-heterocycloalkyl$_{(C \leq 8)}$, alkylamino$_{(C \leq 8)}$, dialkylamino$_{(C \leq 8)}$, alkenylamino$_{(C \leq 8)}$, alkoxyamino$_{(C \leq 8)}$, arylamino$_{(C \leq 8)}$, aralkylamino$_{(C \leq 8)}$, heteroarylamino$_{(C \leq 8)}$, heterocycloalkyl-amino$_{(C \leq 8)}$, alkylsulfonylamino$_{(C \leq 8)}$, amido$_{(C \leq 8)}$, —NH-amido$_{(C \leq 8)}$, or a substituted version of any of these groups;

or a pharmaceutically acceptable salt thereof.

In some embodiments, n is 1. In other embodiments, n is 2. In still other embodiments, n is 3.

In some embodiments, R$_1$ is —H. In some embodiments, R$_2$ is methyl.

In some embodiments, R$_3$ is N-heteroaryl$_{(C \leq 8)}$, for example, imidazolyl. In some embodiments, R$_3$ is N-heterocycloalkyl$_{(C \leq 8)}$, for example, morpholinyl or pyrrolidinyl. In some embodiments, R$_3$ is alkylamino$_{(C \leq 8)}$, for example, ethylamino.

In some embodiments, the compounds are selected from the groups comprising:

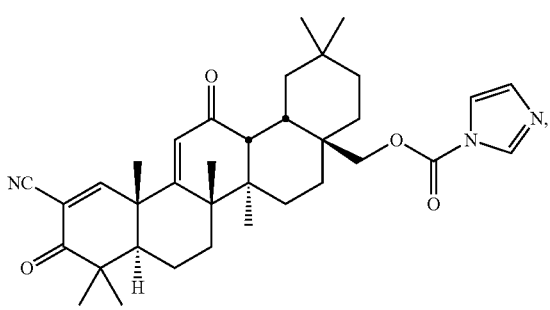

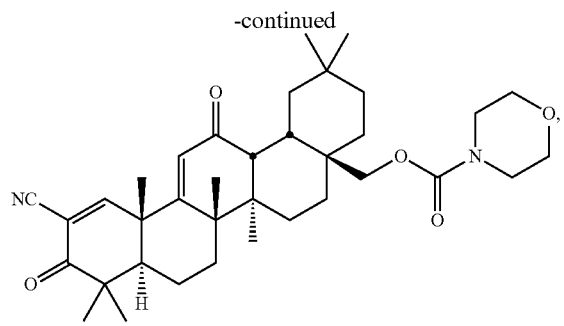

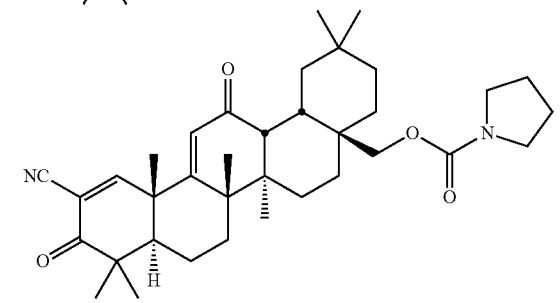

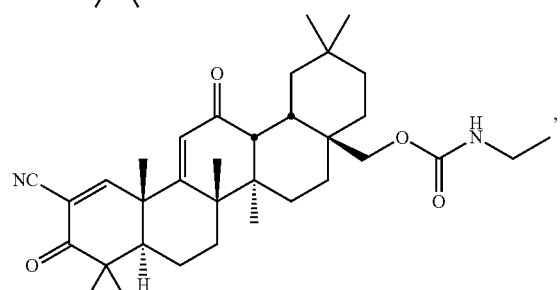

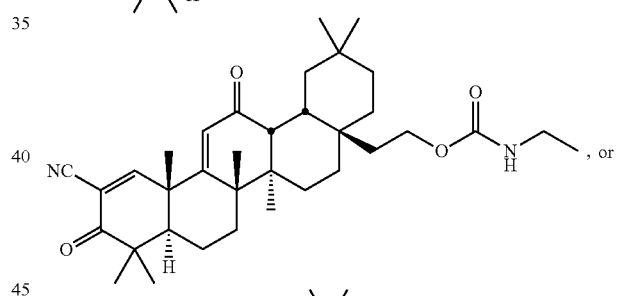

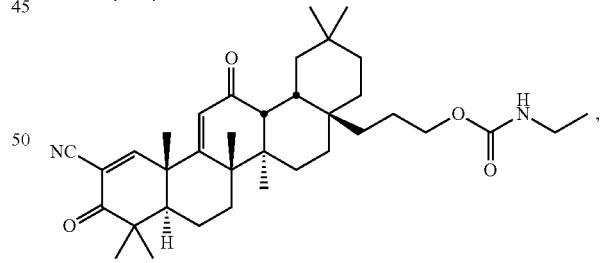

or a pharmaceutically acceptable salt thereof.

In some aspects, there are provided pharmaceutical compositions comprising one or more of the above compounds and an excipient. In other aspects there are provided methods of treating and/or preventing a disease or a disorder in patients in need thereof, comprising administering to such patients one or more of the above compounds in an amount sufficient to treat and/or prevent the disease or disorder.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

DESCRIPTION OF ILLUSTRATIVE EMBODIMENTS

Disclosed herein are new compounds and compositions with antioxidant and/or anti-inflammatory properties, methods for their manufacture, and methods for their use, including for the treatment and/or prevention of disease.

I. DEFINITIONS

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means=S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⚌" represents a single bond or a double bond. Thus, for example, the formula

includes

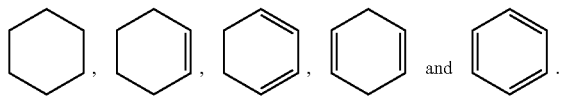

And it is understood that no one such ring atom forms part of more than one double bond. Furthermore, it is noted that the covalent bond symbol "—", when connecting one or two stereogenic atoms, does not indicate any preferred stereochemistry. Instead, it cover all stereoisomers as well as mixtures thereof. The symbol "⌇", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂▬" means a single bond where the group attached to the thick end of the wedge is "out of the page." The symbol "◁▬" means a single bond where the group attached to the thick end of the wedge is "into the page". The symbol "⌇" means a single bond where the geometry around a double bond (e.g., either E or Z) is undefined. Both options, as well as combinations thereof are therefore intended. The bond orders described above are not limiting when one of the atoms connected by the bond is a metal atom (M). In such cases, it is understood that the actual bonding may comprise significant multiple bonding and/or ionic character. Therefore, unless indicated otherwise, the formulas M-C, M=C, M----C, and M⚌C, each refers to a bond of any and type and order between a metal atom and a carbon atom. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

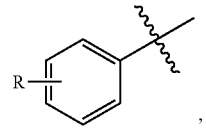

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

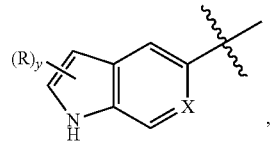

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows:

"(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)₂NH₂. The groups, —CH=CHF, —CH=CHCl and —CH=CHBr, are non-limiting examples of substituted alkenyl groups.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH₃, and —CH₂C≡CCH₃, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

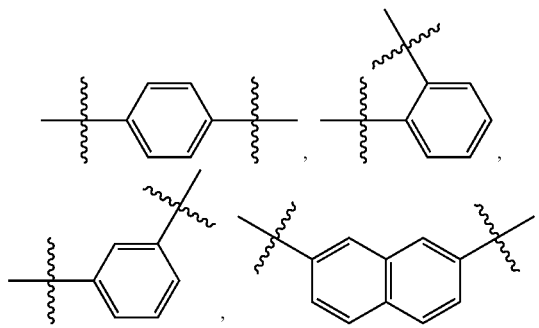

-continued

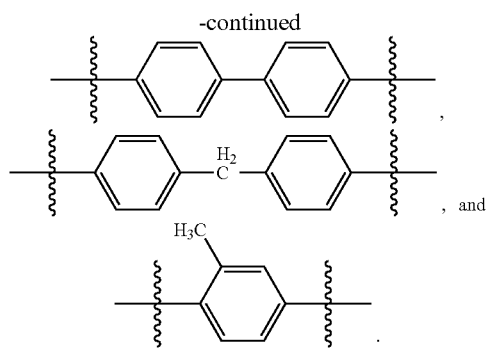

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

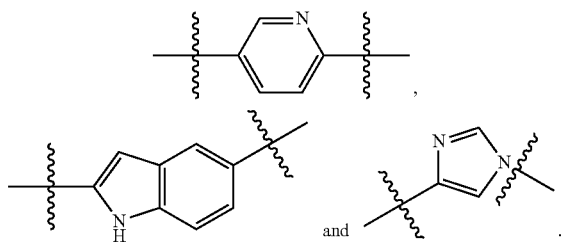

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

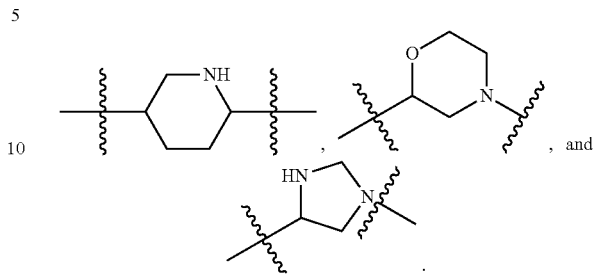

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH (CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is alkenyl, alkynyl, aryl, aralkyl, heteroaryl, heterocycloalkyl, and acyl, respectively. The term "alkoxydiyl" refers to the divalent group —O-alkanediyl-, —O-alkanediyl-, —O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$, The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, alkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$, The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynyl sulfonyl", "aryl sulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

As used herein, a "chiral auxiliary" refers to a removable chiral group that is capable of influencing the stereoselectivity of a reaction. Persons of skill in the art are familiar with such compounds, and many are commercially available.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methane-sulfonates, ethanesulfonates, benzenesulfonates, p-toluenesulfonates, cyclohexyl-sulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Other abbreviations used herein are as follows: DMSO, dimethyl sulfoxide; LiAlH$_4$, lithium aluminum hydride; DMF, dimethylformamide; MeCN, acetonitrile; MeOH, methanol; EtOH, ethanol; EtOAc, ethyl acetate; tBuOH, tert-butanol; $^i$PrOH, isopropanol; $^c$HexOH, cyclohexanol; Pd/C, palladium on carbon; Ac$_2$O, acetic anhydride; AcOOH, peracetic acid; HCO$_2$Et, ethyl formate; MeOTf, methyl trifluoromethansulfonate; EtNCO, ethyl isocyanate; THF, tetrahydrofuran; KO$^t$Bu, potassium tert-butoxide; NaOMe, sodium methoxide; MTBE, methyl tert-butyl ether; DME, dimethoxyethane; NBS, N-bromosuccinimide; DIBAL-H, diisobutylaluminium hydride; CDI, carbonyldiimidazole; DIEA, diisopropylethylamine; HOBt.xH$_2$O, hydroxybenzotriazole hydrate; TEA, triethylamine; DMAP, dimethylaminopyridine; EDCl, 1-ethyl-3-(3-dimethylaminopropyl)carbodiimide; 4 Å MS, 4 angstrom molecular sieves; NMO, N-methylmorpholine N-oxide; TPAP, tetrapropylammonium perruthenate; DBDMH, 1,3-dibromo-5,5-dimethylhydantoin; NO, nitric oxide; iNOS, inducible nitric oxide synthase; COX-2, cyclooxygenase-2; FBS, fetal bovine serum; IFNγ or IFN-γ, interferon-γ; TNFα or TNF-α, tumor necrosis factor-α; IL-1β, interleukin-1β; HO-1, inducible heme oxygenase.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. COMPOUNDS AND SYNTHETIC METHODS

The compounds provided by the present disclosure are shown above in the summary of the invention, in the claims, and in the sections below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Atoms making up the compounds of the present invention are intended to include all isotopic forms of such atoms. Compounds of the present invention include those with one or more atoms that have been isotopically modified or enriched, in particular those with pharmaceutically acceptable isotopes or those useful for pharmaceutically research. Isotopes, as used herein, include those atoms having the same atomic number but different mass numbers. By way of general example and without limitation, isotopes of hydrogen include deuterium and tritium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or en vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It should be further recognized that the compounds of the present invention include those that have been further modified to comprise substituents that are convertible to hydrogen in vivo. This includes those groups that may be convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$, Boc), benzyloxycarbonyl, p-methoxy-benzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$, Boc), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

III. BIOLOGICAL ACTIVITY

Assay results for the suppression of IFNγ-induced NO production are shown for several of the compounds of the present invention in Table 1 below. In the right-hand column of this table under the RAW264.7 heading, the results are compared to those of bardoxolone methyl (RTA 402, CDDO-Me). Details regarding this assay are provided in the Examples section below.

TABLE 1

Suppression of IFNγ-Induced NO Production.

| Compound No. | Molecular Formula | MW | RAW264.7 NO IC$_{50}$ (nM) | Relative NO IC$_{50}$ |
|---|---|---|---|---|
| TX63403 | | 475.71 | 8.6 | 4.3 |
| TX63608 | | 491.70 | 1.1 | 0.5 |
| TX63609 | | 505.73 | 2.9 | 1.2 |

TABLE 1-continued

Suppression of IFNγ-Induced NO Production.

| Compound No. | Molecular Formula | MW | RAW264.7 NO IC$_{50}$ (nM) | Relative NO IC$_{50}$ |
|---|---|---|---|---|
| TX63610 | | 533.74 | 2.2 | 0.9 |
| TX63742 | | 533.74 | 2.0 | 1.0 |
| TX63743 | | 531.73 | 3.2 | 1.6 |
| TX63744 | | 505.73 | 1.1 | 0.6 |
| TX63762 | | 519.71 | 1.2 | 1.0 |

TABLE 1-continued

Suppression of IFNγ-Induced NO Production.

| Compound No. | Molecular Formula | MW | RAW264.7 NO IC$_{50}$ (nM) | Relative NO IC$_{50}$ |
|---|---|---|---|---|
| TX63763 | | 588.82 | 0.4 | 0.3 |
| TX63764 | | 600.75 | 0.7 | 0.6 |
| TX63768 | | 546.78 | 0.3 | 0.2 |
| TX63770 | | 532.76 | 0.2 | 0.2 |

TABLE 1-continued

Suppression of IFNγ-Induced NO Production.

| | | | RAW264.7 | |
| --- | --- | --- | --- | --- |
| Compound No. | Molecular Formula | MW | NO IC$_{50}$ (nM) | Relative NO IC$_{50}$ |
| TX63868 | | 571.77 | 0.7 | 0.4 |
| TX63926 | | 590.79 | 0.7 | 0.5 |
| TX63927 | | 574.79 | 1.3 | 0.9 |
| TX63930 | | 548.76 | 0.9 | 0.6 |

TABLE 1-continued

Suppression of IFNγ-Induced NO Production.

| Compound No. | Molecular Formula | MW | RAW264.7 NO IC$_{50}$ (nM) | Relative NO IC$_{50}$ |
|---|---|---|---|---|
| TX63949 | | 572.82 | 0.6 | 0.5 |
| TX63950 | | 558.79 | 0.4 | 0.3 |
| TX63981 | | 562.78 | 3.0 | 1.2 |
| TX63983 | | 576.81 | 5.4 | 2.1 |

TABLE 1-continued

Suppression of IFNγ-Induced NO Production.

| Compound No. | Molecular Formula | MW | RAW264.7 NO IC$_{50}$ (nM) | Relative NO IC$_{50}$ |
|---|---|---|---|---|
| TX64042 | | 547.77 | 10 | 3.5 |
| TX64043 | | 561.79 | 21 | 7.1 |
| TX64044 | | 574.79 | 1.3 | 0.4 |
| TX64045 | | 575.78 | 5.6 | 1.9 |

TABLE 1-continued

Suppression of IFNγ-Induced NO Production.

| Compound No. | Molecular Formula | MW | RAW264.7 NO IC$_{50}$ (nM) | Relative NO IC$_{50}$ |
|---|---|---|---|---|
| TX64046 | | 595.81 | 8.5 | 2.9 |
| TX64047 | | 588.82 | 3.3 | 1.1 |
| TX64048 | | 602.85 | 1.2 | 0.4 |
| TX64049 | | 608.80 | 2.0 | 0.7 |

TABLE 1-continued

Suppression of IFNγ-Induced NO Production.

| | | | RAW264.7 | |
|---|---|---|---|---|
| Compound No. | Molecular Formula | MW | NO IC$_{50}$ (nM) | Relative NO IC$_{50}$ |
| TX64052 | | 590.79 | 2.0 | 0.7 |
| TX64053 | | 702.96 | 37 | 13 |
| TX64054 | | 576.77 | 97 | 56 |
| TX64055 | | 602.85 | 1.7 | 1.2 |

TABLE 1-continued
Suppression of IFNγ-Induced NO Production.
| Compound No. | Molecular Formula | MW | RAW264.7 NO IC$_{50}$ (nM) | Relative NO IC$_{50}$ |
|---|---|---|---|---|
| TX64056 | 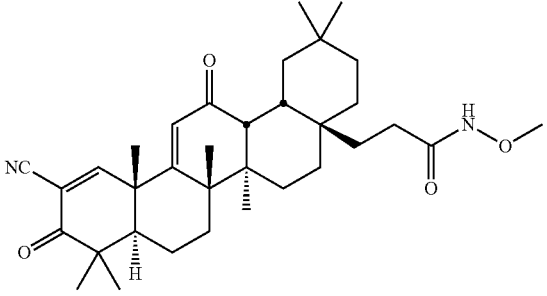 | 548.76 | 0.3 | 0.2 |
| TX64057 | 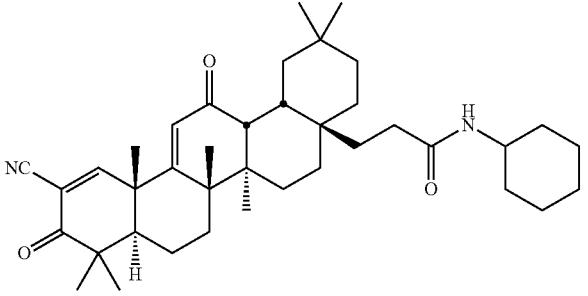 | 600.87 | 0.8 | 0.4 |
| TX64058 | 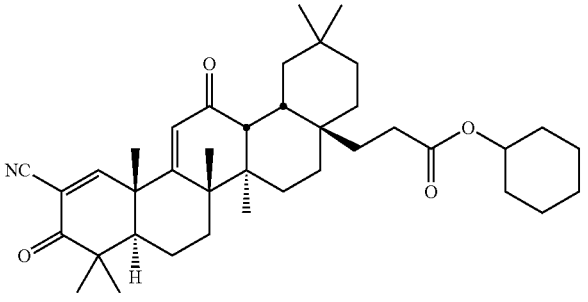 | 601.86 | 29 | 20 |
| TX64059 | 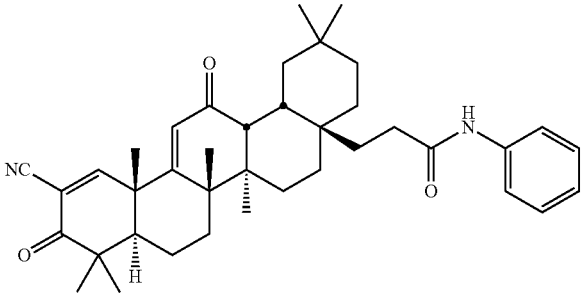 | 594.83 | 1.4 | 0.8 |

TABLE 1-continued

Suppression of IFNγ-Induced NO Production.

| Compound No. | Molecular Formula | MW | RAW264.7 NO IC$_{50}$ (nM) | Relative NO IC$_{50}$ |
|---|---|---|---|---|
| TX64060 | | 546.78 | 0.4 | 0.2 |
| TX64064 | | 560.81 | 0.4 | 0.2 |
| TX64065 | | 574.84 | 0.6 | 0.3 |
| TX64066 | | 609.84 | 20 | 13.8 |

TABLE 1-continued

Suppression of IFNγ-Induced NO Production.

| Compound No. | Molecular Formula | MW | RAW264.7 NO IC$_{50}$ (nM) | Relative NO IC$_{50}$ |
|---|---|---|---|---|
| TX64067 | | 575.82 | 14 | 10 |
| TX64068 | | 595.81 | 1.1 | 0.8 |
| TX64074 | | 518.73 | 0.3 | 0.3 |
| TX64124 | | 687.95 | 3.4 | 2.2 |

TABLE 1-continued

Suppression of IFNγ-Induced NO Production.

| | | | RAW264.7 | |
| Compound No. Molecular Formula | | MW | NO IC$_{50}$ (nM) | Relative NO IC$_{50}$ |
| --- | --- | --- | --- | --- |
| TX64135 | 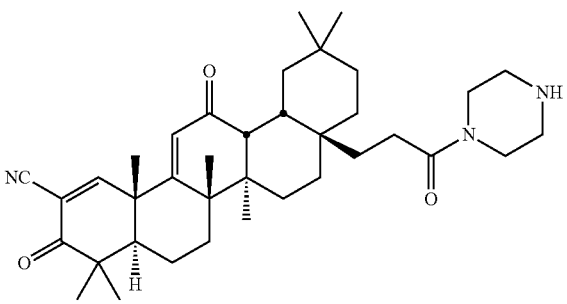 | 587.84 | 1.5 | 1.0 |

IV. DISEASES ASSOCIATED WITH INFLAMMATION AND/OR OXIDATIVE STRESS

Inflammation is a biological process that provides resistance to infectious or parasitic organisms and the repair of damaged tissue. Inflammation is commonly characterized by localized vasodilation, redness, swelling, and pain, the recruitment of leukocytes to the site of infection or injury, production of inflammatory cytokines such as TNF-α and IL-1, and production of reactive oxygen or nitrogen species such as hydrogen peroxide, superoxide and peroxynitrite. In later stages of inflammation, tissue remodeling, angiogenesis, and scar formation (fibrosis) may occur as part of the wound healing process. Under normal circumstances, the inflammatory response is regulated and temporary and is resolved in an orchestrated fashion once the infection or injury has been dealt with adequately. However, acute inflammation can become excessive and life-threatening if regulatory mechanisms fail. Alternatively, inflammation can become chronic and cause cumulative tissue damage or systemic complications. Based at least on the evidence presented above, the compounds of this invention may be used in the treatment or prevention of inflammation or diseases associated with inflammation.

Many serious and intractable human diseases involve dysregulation of inflammatory processes, including diseases such as cancer, atherosclerosis, and diabetes, which were not traditionally viewed as inflammatory conditions. In the case of cancer, the inflammatory processes are associated with tumor formation, progression, metastasis, and resistance to therapy. Atherosclerosis, long viewed as a disorder of lipid metabolism, is now understood to be primarily an inflammatory condition, with activated macrophages playing an important role in the formation and eventual rupture of atherosclerotic plaques. Activation of inflammatory signaling pathways has also been shown to play a role in the development of insulin resistance, as well as in the peripheral tissue damage associated with diabetic hyperglycemia. Excessive production of reactive oxygen species and reactive nitrogen species such as superoxide, hydrogen peroxide, nitric oxide, and peroxynitrite is a hallmark of inflammatory conditions. Evidence of dysregulated peroxynitrite production has been reported in a wide variety of diseases (Szabo et al., 2007; Schulz et al., 2008; Forstermann, 2006; Pall, 2007).

Autoimmune diseases such as rheumatoid arthritis, lupus, psoriasis, and multiple sclerosis involve inappropriate and chronic activation of inflammatory processes in affected tissues, arising from dysfunction of self vs. non-self recognition and response mechanisms in the immune system. In neurodegenerative diseases such as Alzheimer's and Parkinson's diseases, neural damage is correlated with activation of microglia and elevated levels of pro-inflammatory proteins such as inducible nitric oxide synthase (iNOS). Chronic organ failure such as renal failure, heart failure, liver failure, and chronic obstructive pulmonary disease is closely associated with the presence of chronic oxidative stress and inflammation, leading to the development of fibrosis and eventual loss of organ function. Oxidative stress in vascular endothelial cells, which line major and minor blood vessels, can lead to endothelial dysfunction and is believed to be an important contributing factor in the development of systemic cardiovascular disease, complications of diabetes, chronic kidney disease and other forms of organ failure, and a number of other aging-related diseases including degenerative diseases of the central nervous system and the retina.

Many other disorders involve oxidative stress and inflammation in affected tissues, including inflammatory bowel disease; inflammatory skin diseases; mucositis related to radiation therapy and chemotherapy; eye diseases such as uveitis, glaucoma, macular degeneration, and various forms of retinopathy; transplant failure and rejection; ischemia-reperfusion injury; chronic pain; degenerative conditions of the bones and joints including osteoarthritis and osteoporosis; asthma and cystic fibrosis; seizure disorders; and neuropsychiatric conditions including schizophrenia, depression, bipolar disorder, post-traumatic stress disorder, attention deficit disorders, autism-spectrum disorders, and eating disorders such as anorexia nervosa. Dysregulation of inflammatory signaling pathways is believed to be a major factor in the pathology of muscle wasting diseases including muscular dystrophy and various forms of cachexia.

A variety of life-threatening acute disorders also involve dysregulated inflammatory signaling, including acute organ failure involving the pancreas, kidneys, liver, or lungs, myocardial infarction or acute coronary syndrome, stroke, septic shock, trauma, severe burns, and anaphylaxis.

Many complications of infectious diseases also involve dysregulation of inflammatory responses. Although an inflammatory response can kill invading pathogens, an excessive inflammatory response can also be quite destructive and in some cases can be a primary source of damage in infected tissues. Furthermore, an excessive inflammatory response can also lead to systemic complications due to overproduction of inflammatory cytokines such as TNF-α and IL-1. This is believed to be a factor in mortality arising from severe influenza, severe acute respiratory syndrome, and sepsis.

The aberrant or excessive expression of either iNOS or cyclooxygenase-2 (COX-2) has been implicated in the pathogenesis of many disease processes. For example, it is clear that NO is a potent mutagen (Tamir and Tannebaum, 1996), and that nitric oxide can also activate COX-2 (Salvemini et al., 1994). Furthermore, there is a marked increase in iNOS in rat colon tumors induced by the carcinogen, azoxymethane (Takahashi et al., 1997). A series of synthetic triterpenoid analogs of oleanolic acid have been shown to be powerful inhibitors of cellular inflammatory processes, such as the induction by IFN-γ of inducible nitric oxide synthase (iNOS) and of COX-2 in mouse macrophages. See Honda et al. (2000a); Honda et al. (2000b), and Honda et al. (2002), which are all incorporated herein by reference.

In one aspect, compounds disclosed herein are characterized by their ability to inhibit the production of nitric oxide in macrophage-derived RAW 264.7 cells induced by exposure to γ-interferon. They are further characterized by their ability to induce the expression of antioxidant proteins such as NQO1 and reduce the expression of pro-inflammatory proteins such as COX-2 and inducible nitric oxide synthase (iNOS). These properties are relevant to the treatment of a wide array of diseases and disorders involving oxidative stress and dysregulation of inflammatory processes including cancer, complications from localized or total-body exposure to ionizing radiation, mucositis resulting from radiation therapy or chemotherapy, autoimmune diseases, cardiovascular diseases including atherosclerosis, ischemia-reperfusion injury, acute and chronic organ failure including renal failure and heart failure, respiratory diseases, diabetes and complications of diabetes, severe allergies, transplant rejection, graft-versus-host disease, neurodegenerative diseases, diseases of the eye and retina, acute and chronic pain, degenerative bone diseases including osteoarthritis and osteoporosis, inflammatory bowel diseases, dermatitis and other skin diseases, sepsis, burns, seizure disorders, and neuropsychiatric disorders.

Without being bound by theory, the activation of the antioxidant/anti-inflammatory Keap1/Nrf2/ARE pathway is believed to be implicated in both the anti-inflammatory and anti-carcinogenic properties of the compounds disclosed herein.

In another aspect, compounds disclosed herein may be used for treating a subject having a condition caused by elevated levels of oxidative stress in one or more tissues. Oxidative stress results from abnormally high or prolonged levels of reactive oxygen species such as superoxide, hydrogen peroxide, nitric oxide, and peroxynitrite (formed by the reaction of nitric oxide and superoxide). The oxidative stress may be accompanied by either acute or chronic inflammation. The oxidative stress may be caused by mitochondrial dysfunction, by activation of immune cells such as macrophages and neutrophils, by acute exposure to an external agent such as ionizing radiation or a cytotoxic chemotherapy agent (e.g., doxorubicin), by trauma or other acute tissue injury, by ischemia/reperfusion, by poor circulation or anemia, by localized or systemic hypoxia or hyperoxia, by elevated levels of inflammatory cytokines and other inflammation-related proteins, and/or by other abnormal physiological states such as hyperglycemia or hypoglycemia.

In animal models of many such conditions, stimulating expression of inducible heme oxygenase (HO-1), a target gene of the Nrf2 pathway, has been shown to have a significant therapeutic effect including models of myocardial infarction, renal failure, transplant failure and rejection, stroke, cardiovascular disease, and autoimmune disease (e.g., Sacerdoti et al., 2005; Abraham & Kappas, 2005; Bach, 2006; Araujo et al., 2003; Liu et al., 2006; Ishikawa et al., 2001; Kruger et al., 2006; Satoh et al., 2006; Zhou et al., 2005; Morse and Choi, 2005; Morse and Choi, 2002). This enzyme breaks free heme down into iron, carbon monoxide (CO), and biliverdin (which is subsequently converted to the potent antioxidant molecule, bilirubin).

In another aspect, compounds of this invention may be used in preventing or treating tissue damage or organ failure, acute and chronic, resulting from oxidative stress exacerbated by inflammation. Examples of diseases that fall in this category include: heart failure, liver failure, transplant failure and rejection, renal failure, pancreatitis, fibrotic lung diseases (cystic fibrosis, COPD, and idiopathic pulmonary fibrosis, among others), diabetes (including complications), atherosclerosis, ischemia-reperfusion injury, glaucoma, stroke, autoimmune disease, autism, macular degeneration, and muscular dystrophy. For example, in the case of autism, studies suggest that increased oxidative stress in the central nervous system may contribute to the development of the disease (Chauhan and Chauhan, 2006).

Evidence also links oxidative stress and inflammation to the development and pathology of many other disorders of the central nervous system, including psychiatric disorders such as psychosis, major depression, and bipolar disorder; seizure disorders such as epilepsy; pain and sensory syndromes such as migraine, neuropathic pain or tinnitus; and behavioral syndromes such as the attention deficit disorders. See, e.g., Dickerson et al., 2007; Hanson et al., 2005; Kendall-Tackett, 2007; Lencz et al., 2007; Dudhgaonkar et al., 2006; Lee et al., 2007; Morris et al., 2002; Ruster et al., 2005; McIver et al., 2005; Sarchielli et al., 2006; Kawakami et al., 2006; Ross et al., 2003, which are all incorporated by reference herein. For example, elevated levels of inflammatory cytokines, including TNF, interferon-γ, and IL-6, are associated with major mental illness (Dickerson et al., 2007). Microglial activation has also been linked to major mental illness. Therefore, downregulating inflammatory cytokines and inhibiting excessive activation of microglia could be beneficial in patients with schizophrenia, major depression, bipolar disorder, autism-spectrum disorders, and other neuropsychiatric disorders.

Accordingly, in pathologies involving oxidative stress alone or oxidative stress exacerbated by inflammation, treatment may comprise administering to a subject a therapeutically effective amount of a compound of this invention, such as those described above or throughout this specification. Treatment may be administered preventively, in advance of a predictable state of oxidative stress (e.g., organ transplantation or the administration of radiation therapy to a cancer patient), or it may be administered therapeutically in settings involving established oxidative stress and inflammation.

The compounds disclosed herein may be generally applied to the treatment of inflammatory conditions, such as sepsis, dermatitis, autoimmune disease and osteoarthritis. In one aspect, the compounds of this invention may be used to treat inflammatory pain and/or neuropathic pain, for example, by inducing Nrf2 and/or inhibiting NF-κB.

In some embodiments, the compounds disclosed herein may be used in the treatment and prevention of diseases such as cancer, inflammation, Alzheimer's disease, Parkinson's disease, multiple sclerosis, autism, amyotrophic lateral sclerosis, Huntington's disease, autoimmune diseases such as rheumatoid arthritis, lupus, Crohn's disease and psoriasis, inflammatory bowel disease, all other diseases whose pathogenesis is believed to involve excessive production of either nitric oxide or prostaglandins, and pathologies involving oxidative stress alone or oxidative stress exacerbated by inflammation.

Another aspect of inflammation is the production of inflammatory prostaglandins such as prostaglandin E. These molecules promote vasodilation, plasma extravasation, localized pain, elevated temperature, and other symptoms of inflammation. The inducible form of the enzyme COX-2 is associated with their production, and high levels of COX-2 are found in inflamed tissues. Consequently, inhibition of COX-2 may relieve many symptoms of inflammation and a number of important anti-inflammatory drugs (e.g., ibuprofen and celecoxib) act by inhibiting COX-2 activity. Recent research, however, has demonstrated that a class of cyclopentenone prostaglandins (cyPGs) (e.g., 15-deoxy prostaglandin J2, a.k.a. PGJ2) plays a role in stimulating the orchestrated resolution of inflammation (e.g., Rajakariar et al., 2007). COX-2 is also associated with the production of cyclopentenone prostaglandins. Consequently, inhibition of COX-2 may interfere with the full resolution of inflammation, potentially promoting the persistence of activated immune cells in tissues and leading to chronic, "smoldering" inflammation. This effect may be responsible for the increased incidence of cardiovascular disease in patients using selective COX-2 inhibitors for long periods of time.

In one aspect, the compounds disclosed herein may be used to control the production of pro-inflammatory cytokines within the cell by selectively activating regulatory cysteine residues (RCRs) on proteins that regulate the activity of redox-sensitive transcription factors. Activation of RCRs by cyPGs has been shown to initiate a pro-resolution program in which the activity of the antioxidant and cytoprotective transcription factor Nrf2 is potently induced and the activities of the pro-oxidant and pro-inflammatory transcription factors NF-κB and the STATs are suppressed. In some embodiments, this increases the production of antioxidant and reductive molecules (NQO1, HO-1, SOD1, γ-GCS) and decreases oxidative stress and the production of pro-oxidant and pro-inflammatory molecules (iNOS, COX-2, TNF-α). In some embodiments, the compounds of this invention may cause the cells that host the inflammatory event to revert to a non-inflammatory state by promoting the resolution of inflammation and limiting excessive tissue damage to the host.

V. PHARMACEUTICAL FORMULATIONS AND ROUTES OF ADMINISTRATION

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include: sterile aqueous solutions (where water soluble), dispersions, and sterile powders for the extemporaneous preparation of sterile injectable solutions or dispersion. See for example U.S. Patent Application by J. Zhang, entitled "Amorphous Solid Dispersions of CDDO-Me for Delayed Release Oral Dosage Compositions," filed Feb. 13, 2009, which is incorporated herein by reference. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like.

The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milli-gram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the subject has eaten or will eat.

VI. COMBINATION THERAPY

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the invention may be combined with agents designed to improve a patient's immune response to cancer, including (but not limited to) cancer vaccines. See Lu et al. (2011), which is incorporated herein by reference.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Methods and Materials

Nitric Oxide Production and Cell Viability Assay.

RAW264.7 mouse macrophages were plated in 96-well plates at 30,000 cells/well in triplicate in RPMI1640+0.5% FBS and incubated at 37° C. with 5% $CO_2$. On the next day, cells were pre-treated with DMSO or drug (0-200 nM dose range) for 2 hours, and then treated with recombinant mouse IFNγ (R&D Systems) for 24 hours. Nitric Oxide concentration in media was determined using the Griess reagent system (Promega). Cell viability was determined using WST-1 reagent (Roche). $IC_{50}$ values were determined based on the suppression of IFNγ induced Nitric Oxide production normalized to cell viability.

NQO1-ARE Luciferase Reporter Assay.

This assay allows for quantitative assessment of the endogenous activity of the Nrf2 transcription factor in cultured mammalian cells. Expression of Firefly luciferase from NQO1-ARE luciferase reporter plasmid is controlled by binding of Nrf2 to a specific enhancer sequence corresponding to the antioxidant response element (ARE) that was identified in the promoter region of the human NADPH:quinone oxidoreductase 1 (NQO1) gene (Xie et al., 1995). The plasmid was constructed by inserting a sequence:

(SEQ ID NO: 1)
5'- CAGTCACAGTGACTCAGCAGAATCTG-3' encompassing the human NQO1-ARE into the pLuc-MCS vector using HindIII/XhoI cloning sites (GenScript Corp., Piscataway, N.J.). The assay is performed in HuH7 cells maintained in DMEM (Invitrogen) supplemented with 10% FBS and 100 U/ml (each) of penicillin and streptomycin. For the assay, cells are plated in 96-well plates at 17,000 cells per well. Twenty four hours later, the cells are co-transfected with 50 ng each of NQO1-ARE reporter plasmid and pRL-TK plasmid using Lipofectamine 2000 transfection reagent (Invitrogen). pRL-TK plasmid constitutively expresses Renilla luciferase and is used as an internal control for normalization of transfection levels. Thirty hours after transfection, the cells are treated with compounds (at concentrations ranging from 0 to 1 μM) for eighteen hours. Firefly and Renilla luciferase activity is assayed by Dual-Glo Luciferase Assay (Promega Corp., Madison, Wis.), the luminescence signal is measured on an L-Max II luminometer (Molecular Devices). Firefly luciferase activity is normalized to the Renilla activity, and fold induction over a vehicle control (DMSO) of normalized Firefly activity is calculated. The fold induction at 62.5 nM concentration is used for comparing relative potencies of compounds to induce Nrf2 transcriptional activity. See Xie et al., 1995, which is incorporated herein by reference.

Synthetic Schemes, Reagents and Yields

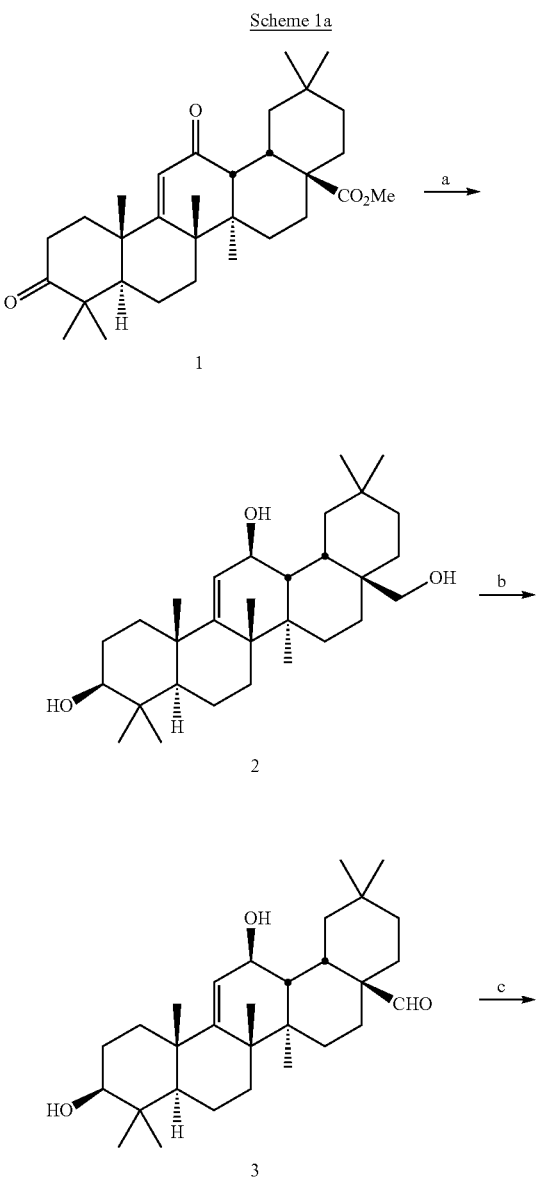

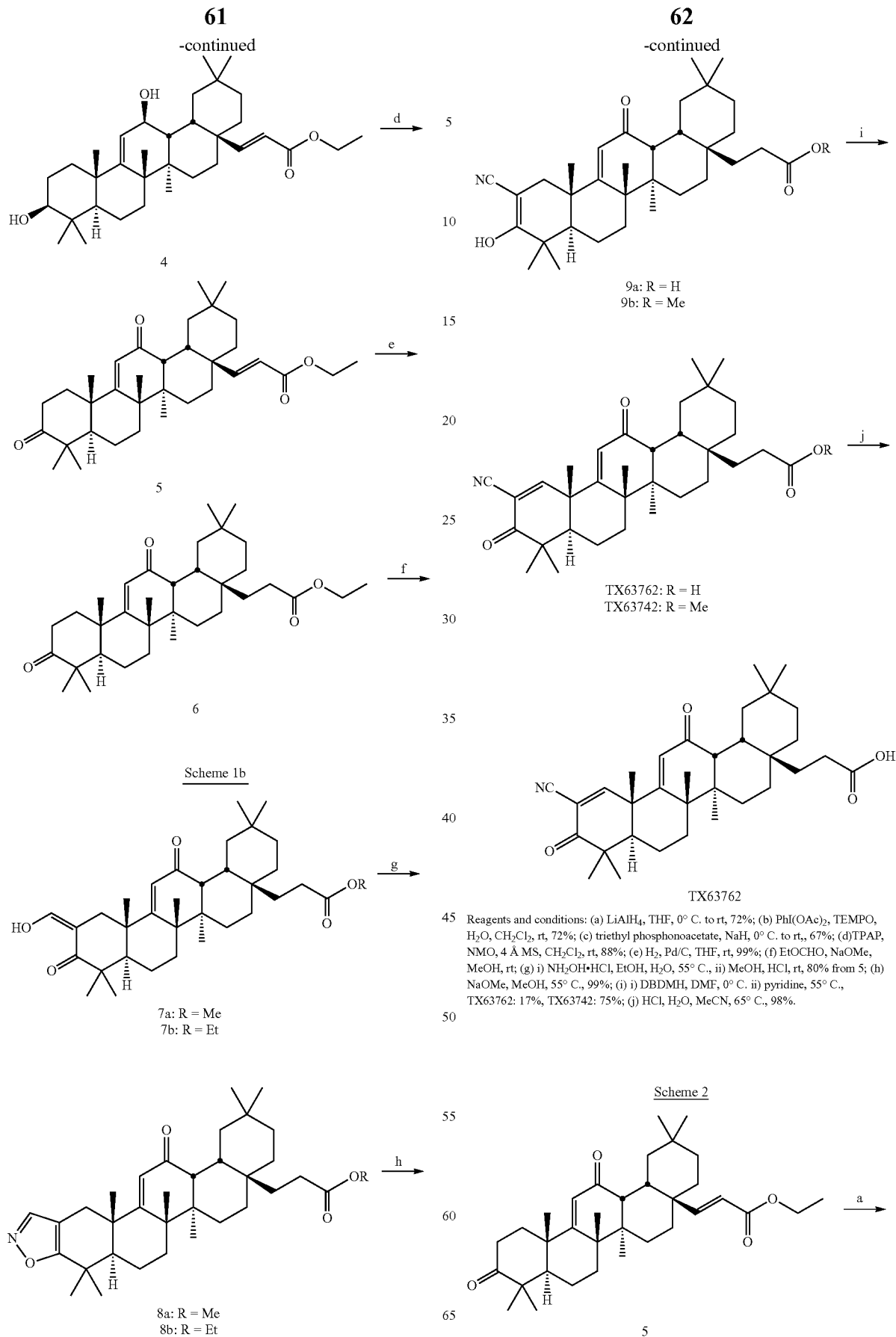

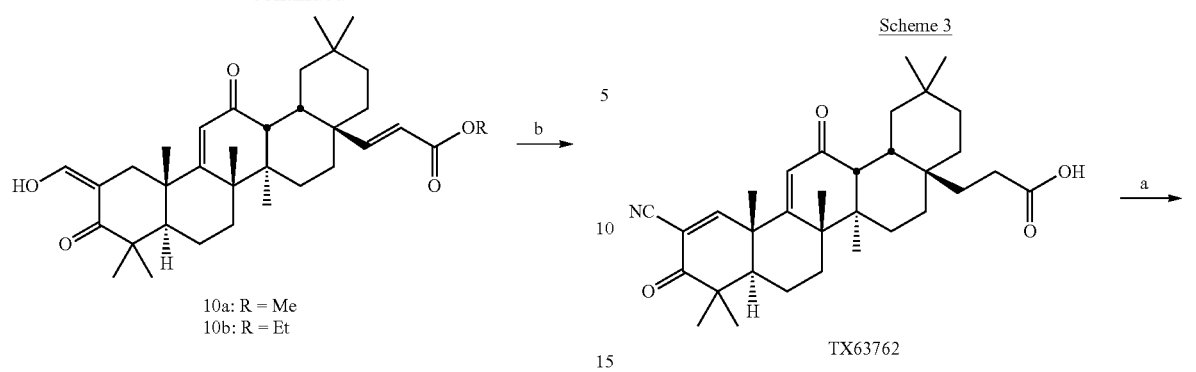
10a: R = Me
10b: R = Et
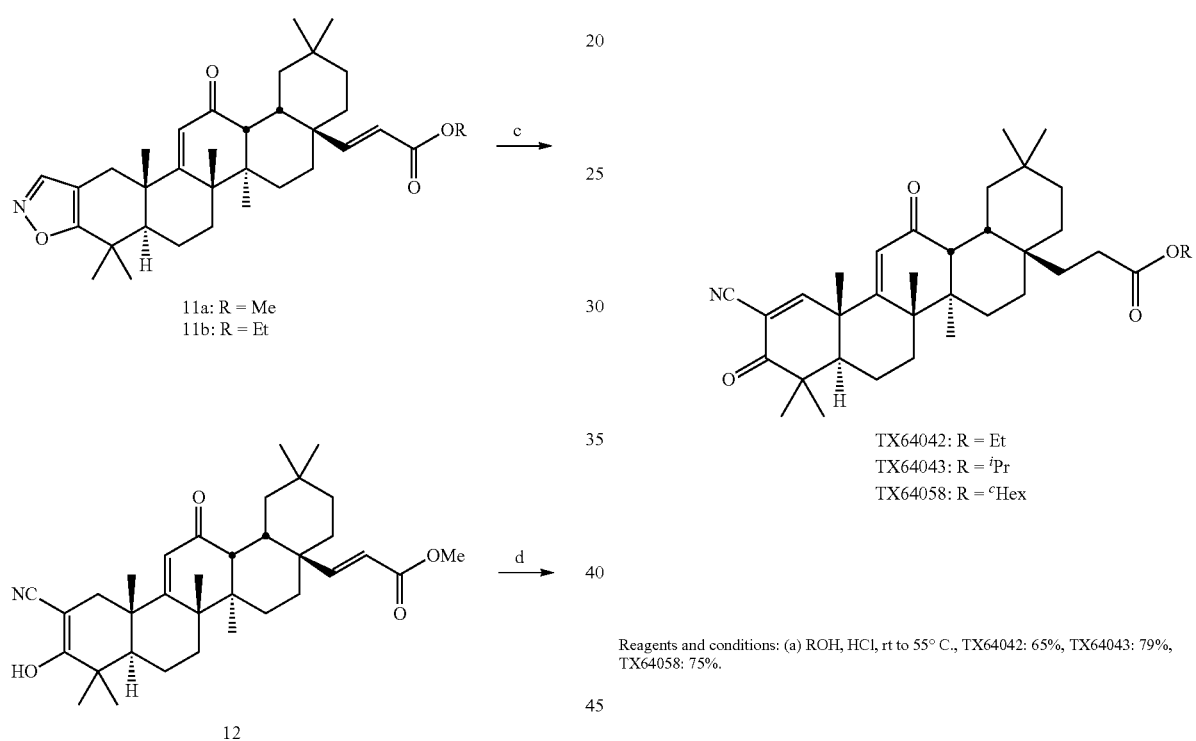
11a: R = Me
11b: R = Et
12
TX63743
Reagents and conditions: (a) HCO₂Et, NaOMe, MeOH, rt; (b) NH₂OH·HCl, EtOH, H₂O, 55° C., 81% from 5; (c) NaOMe, MeOH, 55° C., quantitative; (d) i) DBDMH, DMF, 0° C., ii) pyridine, 55° C., 63% from 11a, 11b.
Scheme 3
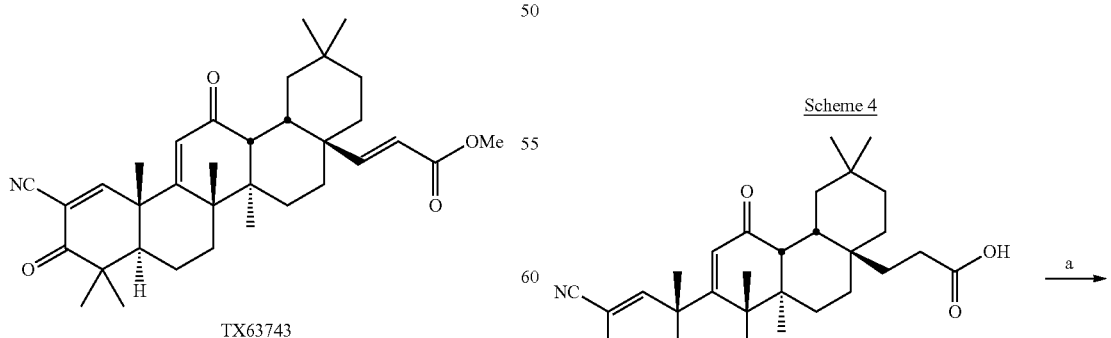
TX63762
TX64042: R = Et
TX64043: R = $^i$Pr
TX64058: R = $^c$Hex
Reagents and conditions: (a) ROH, HCl, rt to 55° C., TX64042: 65%, TX64043: 79%, TX64058: 75%.
Scheme 4
TX63762

-continued

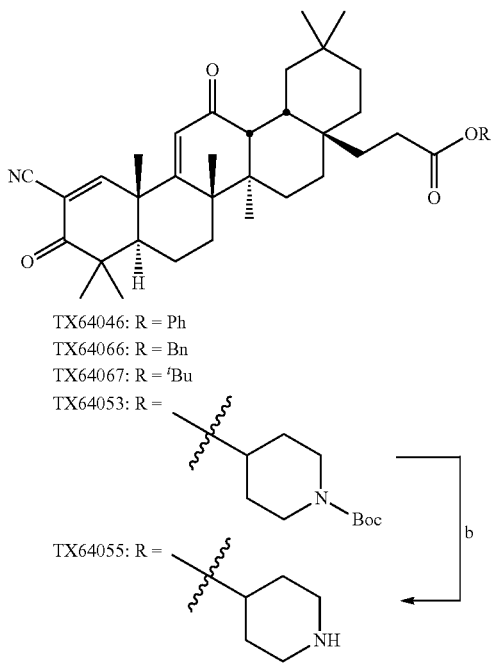

TX64046: R = Ph
TX64066: R = Bn
TX64067: R = $^t$Bu
TX64053: R =

[piperidine-N-Boc]

TX64055: R = [piperidine-NH]

-continued

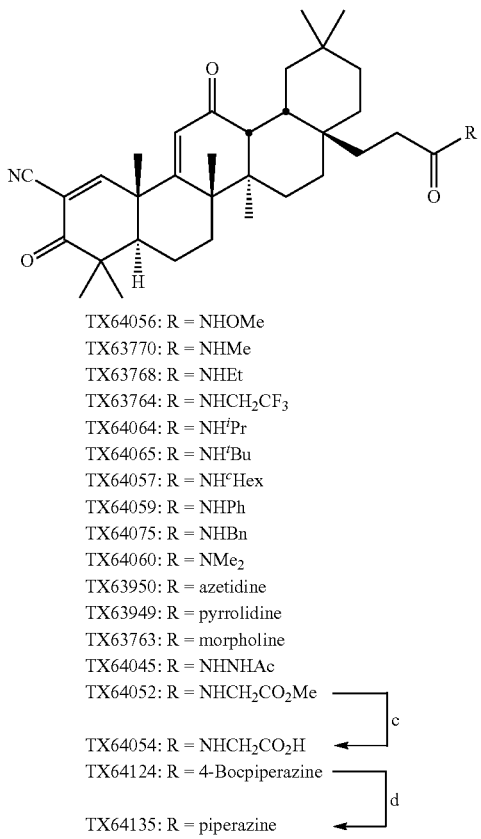

TX64056: R = NHOMe
TX63770: R = NHMe
TX63768: R = NHEt
TX63764: R = NHCH$_2$CF$_3$
TX64064: R = NH$^i$Pr
TX64065: R = NH$^t$Bu
TX64057: R = NH$^c$Hex
TX64059: R = NHPh
TX64075: R = NHBn
TX64060: R = NMe$_2$
TX63950: R = azetidine
TX63949: R = pyrrolidine
TX63763: R = morpholine
TX64045: R = NHNHAc
TX64052: R = NHCH$_2$CO$_2$Me ⟶ c
TX64054: R = NHCH$_2$CO$_2$H ⟵
TX64124: R = 4-Bocpiperazine ⟶ d
TX64135: R = piperazine ⟵

TX64049: [3,3-difluoropyrrolidine]

TX64047: [(3S)-3-hydroxypyrrolidine]

TX64048: [4-hydroxypiperidine]

TX64068: [2-aminopyridine]

TX64044: [3-aminooxetane]

Reagents and conditions: (a) ROH, TEA, DMAP, EDCI, CH$_2$Cl$_2$, rt, TX64046: 64%, TX64066: 64%, TX64067: 15%, TX64053: 70%; (b) HCl, CH$_2$Cl$_2$, 1,4-dioxane, rt, 83%.

Scheme 5

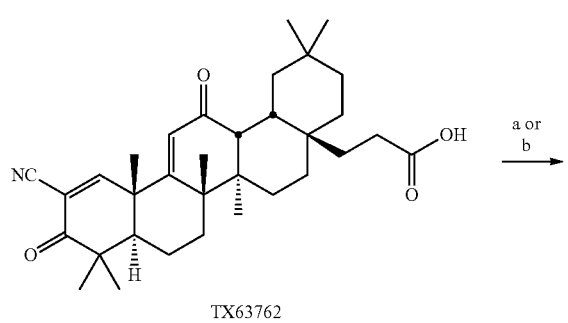

TX63762 a or b

Reagents and conditions: (a) amine, TEA, DMAP, EDCI, CH$_2$Cl$_2$, rt, TX64064: 22%, TX64065: 29%, TX64057: 32%, TX64059: 71%, TX64075: 25%, TX63949: 47%, TX63763: 82%, TX64045: 45%, TX64048: 51%, TX64068: 12%, TX64044: 65%; (b) amine·HCl, TEA, DMAP, EDCI, CH$_2$Cl$_2$, rt, TX64056: 57%, TX63770: 81%, TX63768: 70%, TX63764: 76%, TX64060: 77%, TX63950: 71%, TX64049: 59%, TX64047: 46%, TX64044: 65%, TX64052: 64%; (c) HCl, H$_2$O, MeCN, 55° C., 71%; (d) HCl, 1,4-dioxane, CH$_2$Cl$_2$, rt, 35%.

Scheme 6
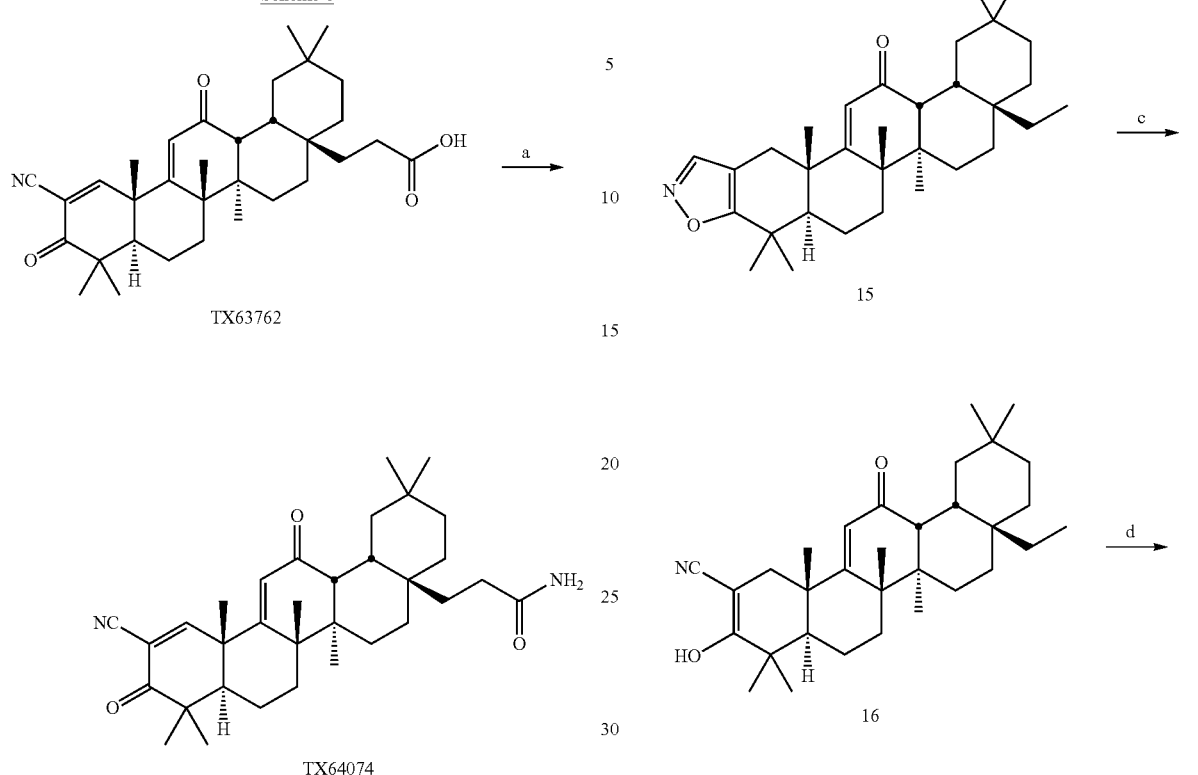
Reagents and conditions: (a) NH₄Cl, EDCI, HOBt•xH₂O, DIEA, DMF, rt, 49%.
Scheme 7
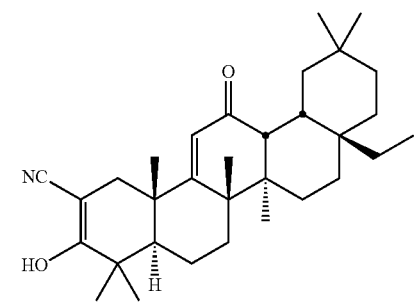
Reagents and conditions: (a) H₂, Pd/C, EtOAc, CH₂Cl₂, rt; (b) HBr, Br₂, MeCN, 35° C., (c) NaOMe, MeOH, 50° C.; (d) i) DBDMH, DMF, 0° C., ii) pyridine, 55° C., 65% from 13.
Scheme 8
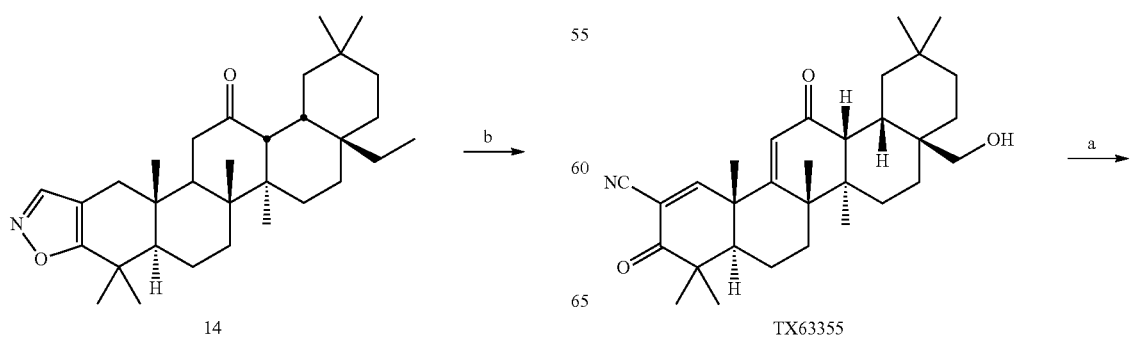

69

-continued

TX63868

Reagents and conditions: (a) CDI, MeCN, reflux, 5 h, 75%.

70

-continued

TX63927

Reagents and conditions: (a) 1-pyrrolidinecarbonyl chloride, DMAP, pyridine, rt to 90° C., 18 h, 35%.

Scheme 9

TX63355

↓ a

TX63926

Reagents and conditions: (a) 4-morpholinecarbonyl chloride, DMAP, pyridine, rt to 90° C., 18 h, 49%.

Scheme 11

TX63355

↓ a

TX63930

Reagents and conditions: (a) ethyl isocyanate, toluene, rt to 90° C., 16 h, 85%.

Scheme 10

TX63355

Scheme 12a oleanolic acid

→ a

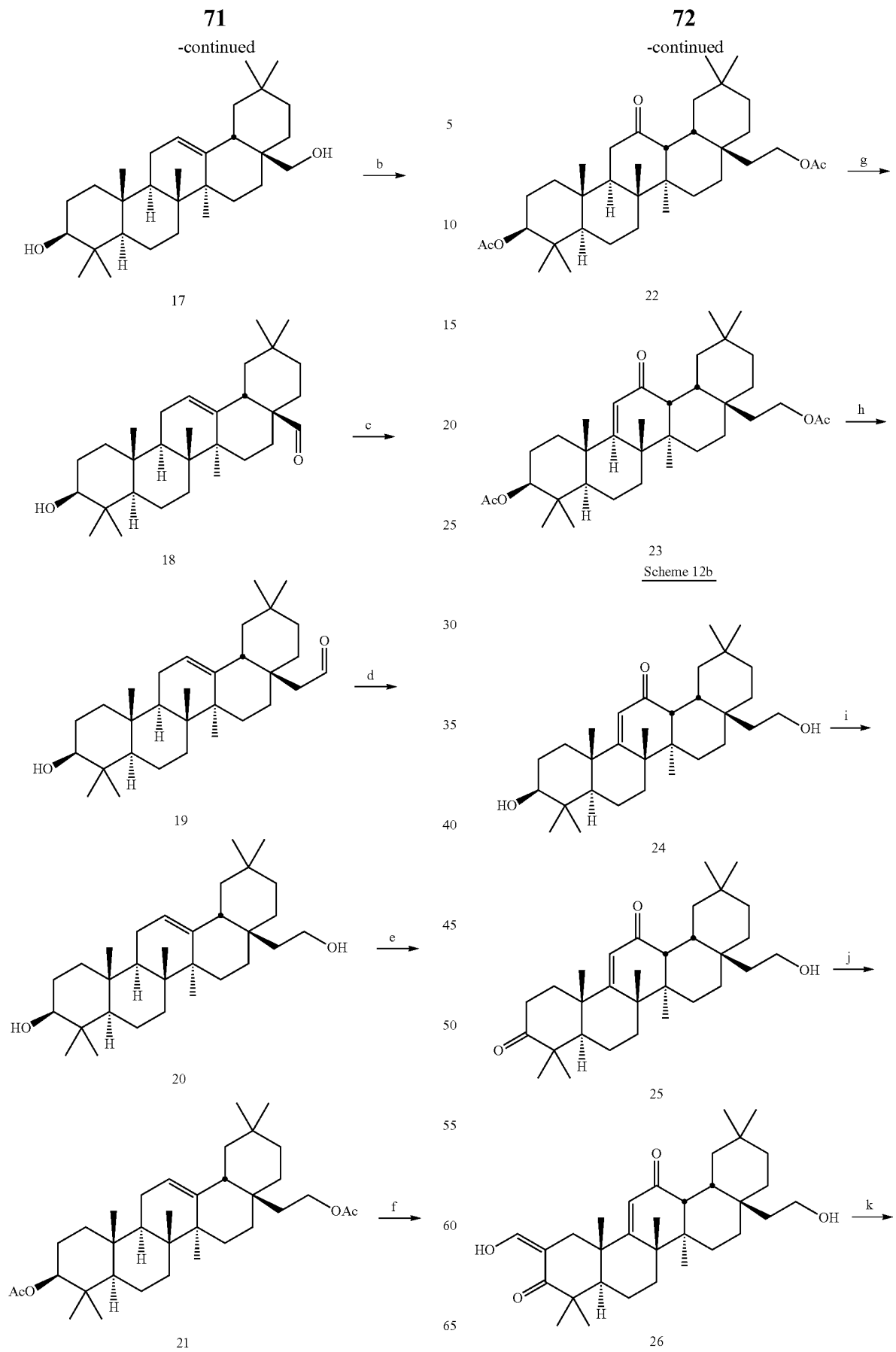

-continued

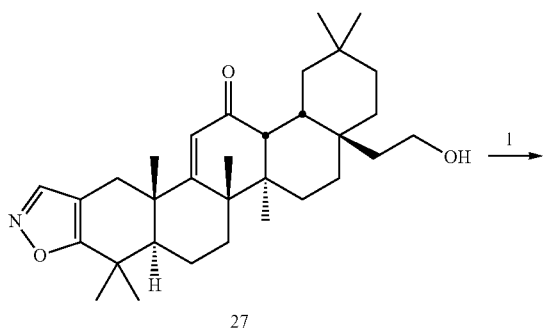
27

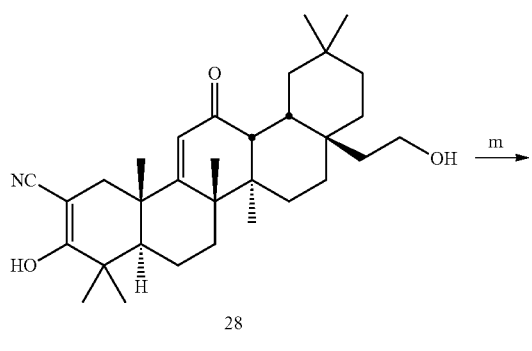
28

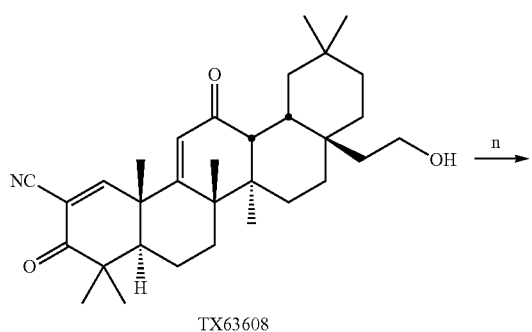
TX63608

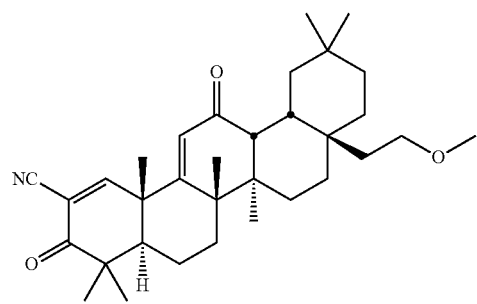
TX63609

-continued

Reagents and conditions:
(a) LiAlH₄, THF, 0° C. to reflux;
(b) NaOCl, NaHCO₃, NaBr, TEMPO, H₂O, CH₂Cl₂, 0° C. to rt, 79% from oleanolic acid;
(c) i) KOtBu, (methoxymethyl)triphenylphosphonium chloride, THF, rt,
   ii) H₂SO₄, rt, 96%;
(d) NaBH₄, MeOH, THF, rt, quantitative;
(e) Ac₂O, pyridine, DMAP, CH₂Cl₂, rt, 75% from 19;
(f) AcOOH, Na₂CO₃, AcOH, 50° C., 96%;
(g) Br₂, HCl, 1,4-dioxane, MeCN, 35° C.;
(h) H₂SO₄, MeOH, THF, 35° C. to reflux, 74% from 22;
(i) NaOCl, AcOH, H₂O, rt, 80%;
(j) NaOMe, MeOH, EtOCHO, 0° C. to rt;
(k) NH₂OH·HCl, EtOH, H₂O, 55° C.;
(l) i) NaOMe, MeOH, 55° C.,
   ii) HCl, 1,4-dioxane, 55° C., 71% from 25;
(m) i) DBDMH, DMF, 0° C.,
   ii) pyridine, 55° C., 80%;
(n) MeOTf, 2,6-di-tert-butyl-4-methylpyridine, CH₂Cl₂, rt, 76%.

Scheme 13

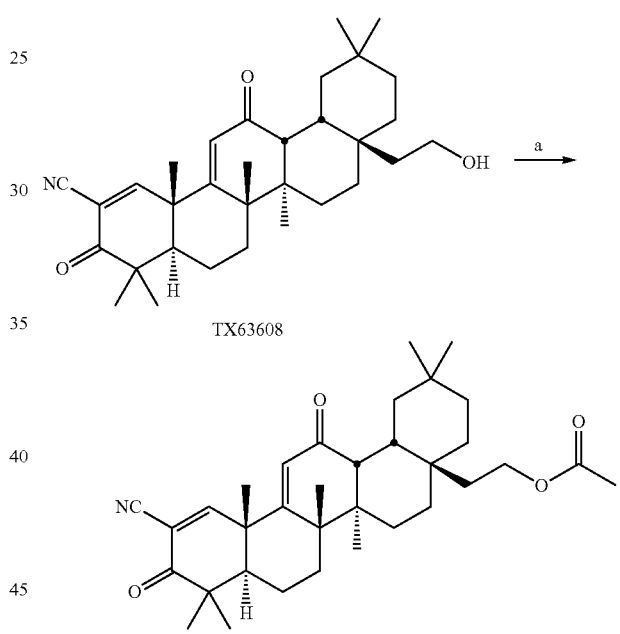
TX63608

TX63610

Reagents and conditions: (a) Ac₂O, pyridine, DMAP, CH₂Cl₂, rt, 76%.

Scheme 14

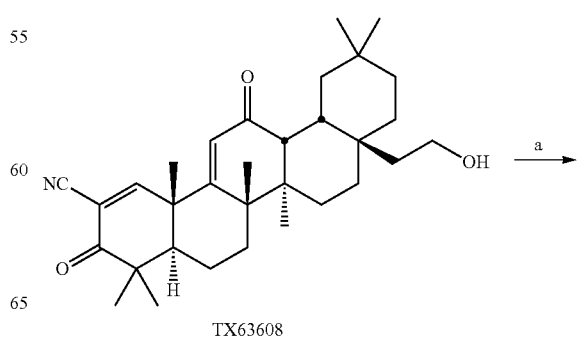
TX63608

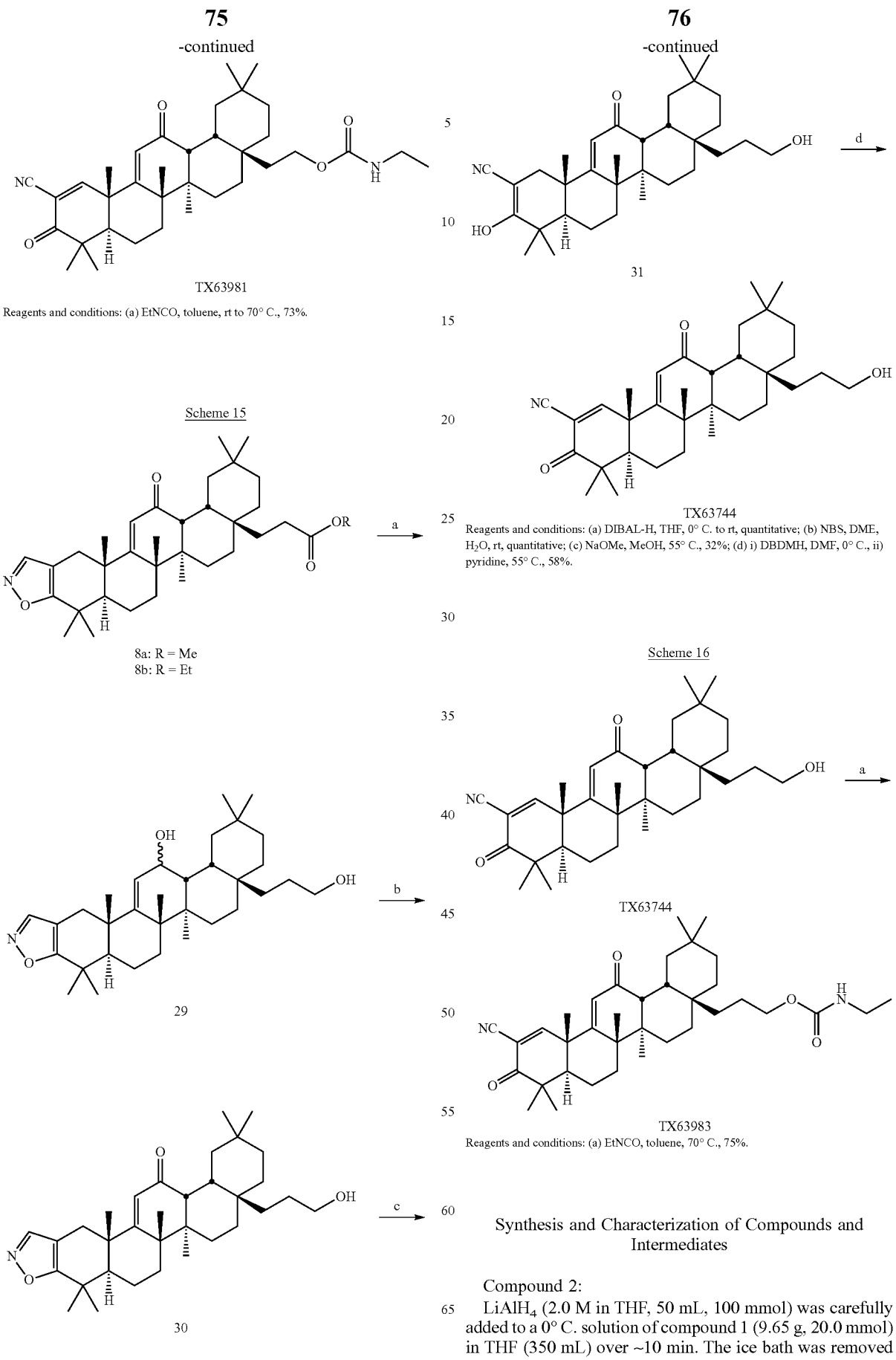
Synthesis and Characterization of Compounds and Intermediates
Compound 2:
LiAlH$_4$ (2.0 M in THF, 50 mL, 100 mmol) was carefully added to a 0° C. solution of compound 1 (9.65 g, 20.0 mmol) in THF (350 mL) over ~10 min. The ice bath was removed after 30 min and the reaction stirred an additional 2.5 h. The solution was diluted with MTBE (200 mL); cooled to 0° C.; and quenched by sequential addition of 5.3 mL each water, 4 M NaOH, and water. The mixture was stirred at room temperature for 30 min, filtered through a plug of celite, eluted with MTBE, and concentrated to give a white solid. The resultant solid was suspended in $CH_2Cl_2$, stirred at room temperature for 2 h, and the solid isolated by filtration [washed with $CH_2Cl_2$, then dried] to give compound 2 (6.56 g, 72%) which was used without further purification: m/z 441.3 (M-$H_2O$+1).

Compound 3:

PhI(OAc)$_2$ (10.40 g, 32.3 mmol), TEMPO (2.27 g, 14.5 mmol), and water (15 mL) were added to a room temperature suspension of compound 2 (6.56 g, 14.3 mmol) in $CH_2Cl_2$ (1.5 L) and stirred vigorously for 18 h. The resultant biphasic, homogeneous solution was treated with anhydrous $Na_2SO_4$, stirred an additional 15 min, filtered and concentrated to a viscous oil. The residue was purified by flash chromatography (silica gel, 0% to 100% EtOAc in hexanes) to give compound 3 (4.72 g, 72%) as an off-white solid: m/z 439.3 (M-$H_2O$+1).

Compound 4:

Triethyl phosphonoacetate (18.8 mL, 94.8 mmol) was added to a 0° C. suspension of NaH (3.81 g, 60%, 95.3 mmol) in THF (285 mL), and the resultant mixture stirred at 0° C. for 15 min, then warmed to room temperature over 30 min. The mixture was cooled to 0° C., a solution of compound 3 (8.67 g, 19.0 mmol) in THF (75 mL) was added, and the transfer completed with THF (20 mL) wash. The reaction was maintained at 0° C. for approximately 4 h and then warmed to room temperature overnight. The reaction was again cooled to 0° C. and quenched by the careful addition of 1 N HCl, stirred vigorously at room temperature for 15 min, and extracted with MTBE. The combined organic fractions were washed with brine, then dried over $Na_2SO_4$, and concentrated. The residue was purified by flash chromatography (silica gel, 0% to 100% EtOAc in hexanes) to give compound 4 (6.68 g, 67%) as a white solid: m/z 509.3 (M–$H_2O$+1).

Compound 5:

A mixture of compound 4 (6.68 g, 12.7 mmol), 4 Å MS (12.7 g), NMO (4.47 g, 38.2 mmol), and $CH_2Cl_2$ (250 mL) was stirred at room temperature for 15 min. TPAP (458 mg, 1.30 mmol) was then added, and the reaction was stirred for 1 h. The reaction was concentrated to ~10 mL and purified by flash chromatography (silica gel, 0% to 100% EtOAc in hexanes) to give compound 5 (5.89 g, 88%) as a white foam solid: m/z 523.3 (M+1).

Compound 6:

A flask containing a suspension of compound 5 (5.89 g, 11.3 mmol), Pd/C (10%, 1.45 g), and THF (250 mL) was purged with $N_2$ and then $H_2$, and the reaction was vigorously stirred under $H_2$ (balloon pressure) for 5 h. The resultant suspension was sparged with $N_2$ for 30 min, filtered through a short plug of celite, eluted with $CH_2Cl_2$, and concentrated to give compound 6 (5.84 g, 99%) as a white solid: m/z 525.4 (M+1).

Compounds 7a,7b:

A solution of compound 6 (5.84 g, 11.1 mmol), NaOMe (25% in MeOH, 35 mL) and $HCO_2Et$ (70 mL) was stirred at room temperature for 3 h, diluted with 1 N HCl, and extracted with EtOAc. The combined organic fractions were washed with brine, dried with $Na_2SO_4$, and concentrated to give compounds 7a,b (Me-ester:Et-ester=9:91) as an off-white foam solid that was used without further purification: 7a m/z 539.3 (M+1), 7b m/z 553.4 (M+1).

Compound 8a, 8b:

A mixture of compounds 7a, 7b (all above obtained, ~11.3 mmol), $NH_2OH \cdot HCl$ (1.06 g, 15.3 mmol), EtOH (100 mL) and water (17 mL) was heated to 55° C. for 16 h. The resultant solution was cooled to room temperature, diluted with 1 N HCl and extracted with EtOAc. The combined organic fractions were washed with 1 N HCl and brine, dried with $Na_2SO_4$, and concentrated. The residue was dissolved in MeOH (700 mL), treated with 12 N HCl (1.0 mL), and stirred at room temperature for 5 h. The mixture was concentrated to ~30 mL, diluted with $CH_2Cl_2$, washed with brine, dried with $Na_2SO_4$ and concentrated. The residue was purified by flash chromatography (silica gel, 0% to 60% EtOAc in hexanes) to give compounds 8a, 8b (4.84 g, Me-ester:Et-ester=25:75, 80% from 6) as a white solid: 8a m/z 536.4 (M+1), 8b m/z 550.3 (M+1).

Compounds 9a, 9b:

A solution of 8a, 8b (4.84 g, 8.84 mmol), NaOMe (25% in MeOH, 5.3 mL), and MeOH (110 mL) was heated to 55° C. for 5 h. The resultant mixture was diluted with 1 N HCl and extracted with $CH_2Cl_2$. The combined organic fractions were washed with brine, dried with $Na_2SO_4$, and concentrated to give compounds 9a, 9b (4.69 g, carboxylic acid:Me-ester=17:83, 99%) as a yellow solid that was used without further purification: 9a m/z 522.3 (M+1), 9b m/z 536.3 (M+1).

Compounds TX63762 and TX63742:

1,3-dibromo-5,5-dimethylhydantoin (1.25 g, 4.37 mmol) was added to a 0° C. solution of 9a, 9b (4.69 g, 8.79 mmol) in DMF (106 mL). The mixture was stirred at 0° C. for 4 h. Pyridine (2.83 mL, 35.0 mmol) was then added, and the reaction was heated to 55° C. The reaction was cooled to room temperature after 4 h and was stirred an additional 3 d. The resultant solution was diluted with 1 N HCl and extracted with EtOAc. The combined organic fractions were washed with water and brine, dried with $Na_2SO_4$, and concentrated. The residue was purified by flash chromatography (silica gel, 0% to 100% EtOAc in hexanes) to give compound TX63762 (780 mg, 17%) as a white solid and compound TX63742 (3.53 g, 75%) as an off-white solid: TX63762 $^1$H NMR (400 MHz, CDCl$_3$) δ 8.04 (s, 1H), 5.98 (s, 1H), 3.06 (d, 1H, J=4.7 Hz), 2.34 (m, 2H), 2.24 (td, 1H, J=4.3, 13.4 Hz), 1.69 (m, 11H), 1.50 (s, 3H), 1.49 (s, 3H), 1.26 (s, 3H), 1.26 (m, 4H), 1.18 (s, 3H), 1.04 (m, 2H), 1.02 (s, 3H), 0.93 (s, 3H), 0.88 (s, 3H); m/z 520.3 (M+1); TX63742 $^1$H NMR (400 MHz, CDCl$_3$) δ 8.04 (s, 1H), 5.97 (s, 1H), 3.67 (s, 3H), 3.06 (d, 1H, J=4.7 Hz), 2.30 (m, 2H), 2.21 (td, 1H, J=4.6, 13.0 Hz), 1.74 (m, 9H), 1.50 (s, 6H), 1.46 (m, 2H), 1.26 (s, 3H), 1.25 (m, 4H), 1.18 (s, 3H), 1.02 (m, 2H), 1.01 (s, 3H), 0.92 (s, 3H), 0.87 (s, 3H); m/z 534.3 (M+1).

Compound TX63762:

A suspension of TX63742 (3.53 g, 6.61 mmol) in MeCN (200 mL) and 1 N HCl (66 mL) was heated to 65° C. for 17 h. The resultant solution was cooled to room temperature and extracted with EtOAc. The combined organic fractions were washed with brine, dried with $Na_2SO_4$, and concentrated to give compound TX63762 (3.354 g, 98%) as a pale yellow solid.

Compounds 10a, 10b:

A solution of compound 5 (250 mg, 0.478 mmol), NaOMe (25% in MeOH, 1.25 mL) and $HCO_2Et$ (3.75 mL) was stirred at room temperature for 3 h, diluted with EtOAc, washed with 1 N HCl and brine, dried with $Na_2SO_4$, and concentrated to give compounds 10a, 10b (Me-ester:Et-ester=23:77) as an off-white foam solid that were used without further purification: 10a m/z 537.3 (M+1), 10b m/z 551.4 (M+1).

Compounds 11a, 11b:

A mixture of compounds 10a, 10b (all above obtained, 0.48 mmol), NH$_2$OH.HCl (45.1 g, 0.649 mmol), EtOH (4.25 mL) and water (0.75 mL) was heated to 55° C. for 20 h. The resultant solution was cooled to room temperature, diluted with EtOAc, washed with 1 N HCl and brine, dried with Na$_2$SO$_4$, and concentrated. The crude residue was purified by flash chromatography (silica gel, 0% to 60% EtOAc in hexanes) to give compounds 11a, 11b (210 mg, Me-ester: Et-ester=21:79, 81% from 5) as a white solid: 11a m/z 534.3 (M+1), 11b m/z 548.3 (M+1).

Compound 12:

A mixture of compounds 11a, 11b (210 mg, 0.385 mmol), NaOMe (25% in MeOH, 0.2 mL) and MeOH (4.8 mL) was heated to 55° C. for 3.5 h. The resultant mixture was diluted with 1 N HCl and extracted with EtOAc. The combined organic fractions were dried with Na$_2$SO$_4$ and concentrated to give compound 12 (206 mg, quantitative) as a glassy, white solid that was used without further purification: m/z 534.3 (M+1).

Compounds TX63743:

1,3-dibromo-5,5-dimethylhydantoin (57.6 mg, 0.201 mmol) was added to a 0° C. solution of compound 12 (206 mg, 0.385 mmol) in DMF (3.9 mL). The mixture was stirred at 0° C. for 2 h, pyridine (0.13 mL, 1.6 mmol) was added, and the reaction heated to 55° C. The reaction was cooled to room temperature after 4 h and stirred overnight. The resultant solution was diluted with EtOAc, washed with 1 N HCl, 10% Na$_2$SO$_3$, and brine, then dried with Na$_2$SO$_4$ and concentrated. The crude residue was purified by flash chromatography (silica gel, 0% to 45% EtOAc in hexanes) to give compound TX63743 (129 mg, 63% from 11a, 11b) as a white solid: $^1$H NMR (400 MHz, CDCl$_3$) δ 8.02 (s, 1H), 6.95 (d, 1H, J=16.3 Hz), 5.97 (s, 1H), 5.87 (d, 1H, J=16.4 Hz), 3.74 (s, 3H), 2.85 (d, 1H, J=4.6 Hz), 2.57 (td, 1H, J=4.1, 13.2 Hz), 2.06 (dt, 1H, J=4.0, 13.8 Hz), 1.65 (m, 8H), 1.47 (s, 3H), 1.32 (s, 3H), 1.25 (s, 3H), 1.20 (m, 6H), 1.17 (s, 3H), 1.01 (s, 3H), 0.98 (s, 3H), 0.91 (s, 3H); m/z 532.3 (M+1).

Compound TX64042:

A mixture of TX63762 (53.0 mg, 0.102 mmol), EtOH (2 mL) and 12 N HCl (2 drops) was stirred at room temperature for 21 h, then at 50° C. for 5 h. The resultant suspension was diluted with EtOAc to give a homogeneous solution that was washed with brine, dried with Na$_2$SO$_4$, and concentrated. The residue was purified by flash chromatography (silica gel, 0% to 100% EtOAc in hexanes) to give compound TX64042 (36.5 mg, 65%) as a white solid: $^1$H NMR (400 MHz, CDCl$_3$) δ 8.04 (s, 1H), 5.97 (s, 1H), 4.14 (d, 1H, J=7.1 Hz), 4.10 (d, 1H, J=7.1 Hz), 3.07 (d, 1H, J=4.7 Hz), 2.27 (m, 3H), 1.68 (m, 11H), 1.50 (s, 6H), 1.26 (s, 3H), 1.26 (t, 3H, J=7.1 Hz), 1.24 (m, 4H), 1.18 (s, 3H), 1.01 (m, 2H), 1.01 (s, 3H), 0.93 (s, 3H), 0.88 (s, 3H); m/z 548.3 (M+1).

Compound TX64043:

A mixture of TX63762 (52.4 mg, 0.101 mmol), i-PrOH (2 mL) and 12 N HCl (2 drops) was stirred at room temperature for 21 h, then at 50° C. overnight. The resultant suspension was diluted with EtOAc to give a homogeneous solution that was washed with 1 N HCl and brine, dried with Na$_2$SO$_4$, and concentrated. The residue was purified by flash chromatography (silica gel, 0% to 100% EtOAc in hexanes) to give compound TX64043 (44.8 mg, 79%) as a white solid: $^1$H NMR (400 MHz, CDCl$_3$) δ 8.04 (s, 1H), 5.97 (s, 1H), 4.99 (sept, 1H, J=6.3 Hz), 3.08 (d, 1H, J=4.7 Hz), 2.24 (m, 3H), 1.73 (m, 10H), 1.50 (s, 6H), 1.43 (m, 1H), 1.26 (m, 3H), 1.22 (m, 10H), 1.18 (s, 3H), 1.03 (m, 2H), 1.01 (s, 3H), 0.93 (s, 3H), 0.88 (s, 3H); m/z 562.3 (M+1).

Compound TX64058:

A mixture of TX63762 (40.0 mg, 0.0770 mmol), c-HexOH (2 mL) and 37% HCl (2 drops) was stirred at 55° C. for 21 h. The resultant suspension was diluted with EtOAc to give a homogeneous solution that was washed with water and brine, dried with Na$_2$SO$_4$, and concentrated. The residue was purified by flash chromatography (silica gel, 0% to 100% EtOAc in hexanes) to give compound TX64058 (34.8 mg, 75%) as a white solid: $^1$H NMR (400 MHz, CDCl$_3$) δ 8.04 (s, 1H), 5.97 (s, 1H), 4.73 (m, 1H), 3.08 (d, 1H, J=4.7 Hz), 2.26 (m, 3H), 1.77 (m, 12H), 1.55 (s, 3H), 1.50 (s, 3H), 1.32 (m, 13H), 1.26 (s, 3H), 1.18 (s, 3H), 1.03 (m, 2H), 1.01 (s, 3H), 0.93 (s, 3H), 0.88 (s, 3H); m/z 602.4 (M+1).

Compound TX64046:

A mixture of compound TX63762 (39.0 mg, 0.0750 mmol), TEA (0.03 mL, 0.2 mmol), DMAP (18.1 mg, 0.148 mmol), phenol (22.5 mg, 0.239 mmol) and CH$_2$Cl$_2$ (2 mL) was stirred at room temperature for 30 min. EDCI (31.6 mg, 0.165 mmol) was added, and the reaction was stirred at room temperature for 18 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give compound TX64046 (28.5 mg, 64%) as a white solid: $^1$H NMR (400 MHz, CDCl$_3$) δ 8.04 (s, 1H), 7.38 (t, 2H, J=7.8 Hz), 7.23 (t, 1H, J=7.4 Hz), 7.07 (m, 2H), 5.98 (s, 1H), 3.11 (d, 1H, J=4.7 Hz), 2.56 (m, 2H), 2.29 (td, 1H, J=4.7, 13.0 Hz), 1.77 (m, 11H), 1.49 (s, 6H), 1.28 (m, 4H), 1.26 (s, 3H), 1.17 (s, 3H), 1.08 (m, 2H), 1.03 (s, 3H), 0.96 (s, 3H), 0.90 (s, 3H); m/z 596.3 (M+1).

Compound TX64066:

A mixture of TX63762 (53.8 mg, 0.104 mmol), TEA (0.05 mL, 0.4 mmol), DMAP (37.2 mg, 0.304 mmol), benzyl alcohol (0.06 mL, 0.7 mmol) and CH$_2$Cl$_2$ (2 mL) was stirred at room temperature for 15 min. EDCI (59.8 mg, 0.312 mmol) was added, and the reaction was stirred at room temperature for 17 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give compound TX64066 (40.5 mg, 64%) as a white solid: $^1$H NMR (400 MHz, CDCl$_3$) δ 8.03 (s, 1H), 7.35 (m, 5H), 5.97 (s, 1H), 5.12 (d, 1H, J=12.3 Hz), 5.09 (d, 1H, J=12.3 Hz), 3.05 (d, 1H, J=4.7 Hz), 2.35 (m, 2H), 2.23 (td, 1H, J=4.7, 13.1 Hz), 1.80 (m, 7H), 1.50 (m, 4H), 1.49 (s, 3H), 1.44 (s, 3H), 1.26 (s, 3H), 1.21 (m, 4H), 1.18 (s, 3H), 1.01 (m, 2H), 1.00 (s, 3H), 0.91 (s, 3H), 0.87 (s, 3H); m/z 610.3 (M+1).

Compound TX64067:

A mixture of TX63762 (51.6 mg, 0.0993 mmol), TEA (0.05 mL, 0.4 mmol), DMAP (38.8 mg, 0.318 mmol), t-BuOH (0.10 mL, 1.0 mmol) and CH$_2$Cl$_2$ (2 mL) was stirred at room temperature for 15 min. EDCI (60.7 mg, 0.317 mmol) was added, and the reaction was stirred at room temperature for 17 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes), then purified by additional flash chromatography (C$_{18}$ silica gel, 0% to 100% MeCN in water) to give compound TX64067 (8.3 mg, 15%) as a white solid: $^1$H NMR (400 MHz, CDCl$_3$) δ 8.04 (s, 1H), 5.97 (s, 1H), 3.07 (d, 1H, J=4.7 Hz), 2.18 (m, 3H), 1.79 (m, 6H), 1.51 (s, 3H), 1.51 (m, 6H), 1.50 (s, 3H), 1.44 (s, 9H), 1.26 (s, 3H), 1.24 (m, 3H), 1.18 (s, 3H), 1.02 (m, 2H), 1.01 (s, 3H), 0.93 (s, 3H), 0.87 (s, 3H); m/z 520.3 (M-t-Bu+H+1).

Compound TX64053:

A mixture of compound TX63762 (70 mg, 0.14 mmol), TEA (0.06 mL, 0.4 mmol), DMAP (52.9 mg, 0.433 mmol), 1-Boc-4-hydroxypiperidine (53.8 mg, 0.267 mmol) and $CH_2Cl_2$ (3 mL) was stirred at room temperature for 15 min. EDCI (78.1 mg, 0.407 mmol) was added, and the reaction was stirred at room temperature for 17 h. The resultant mixture was diluted with EtOAc, washed with 1 N HCl and brine, dried with $Na_2SO_4$, and concentrated. The residue was purified by flash chromatography (silica gel, 0% to 100% EtOAc in hexanes) to give compound TX64053 (68.7 mg, 70%) as a white solid: $^1$H NMR (400 MHz, $CDCl_3$) δ 8.04 (s, 1H), 5.98 (s, 1H), 4.90 (m, 1H), 3.72 (m, 2H), 3.21 (m, 2H), 3.06 (d, 1H, J=4.6 Hz), 2.27 (m, 3H), 1.68 (m, 15H), 1.50 (s, 6H), 1.46 (s, 9H), 1.26 (s, 3H), 1.25 (m, 4H), 1.18 (s, 3H), 1.04 (m, 2H), 1.01 (s, 3H), 0.93 (s, 3H), 0.88 (s, 3H); m/z 603.4 (M-Boc+H+1).

Compound TX64055:

A mixture of TX64053 (21.5 mg, 0.0306 mmol), 4 N HCl in 1,4-dioxane (0.1 ml, 0.4 mmol) and $CH_2Cl_2$ (0.9 mL) was stirred at room temperature for 5 h and cooled to −20° C. overnight. The resultant mixture was diluted with EtOAc, washed with brine, dried with $Na_2SO_4$, and concentrated to give compound TX64055 (15.4 mg, 83%) as a white solid: $^1$H NMR (400 MHz, $CDCl_3$) δ 8.04 (s, 1H), 5.98 (s, 1H), 4.83 (tt, 1H, J=4.2, 9.0 Hz), 3.07 (d, 1H, J=4.9 Hz), 3.05 (m, 1H), 2.71 (m, 2H), 2.27 (m, 3H), 1.69 (m, 17H), 1.50 (s, 6H), 1.26 (s, 3H), 1.25 (m, 4H), 1.18 (s, 3H), 1.03 (m, 2H), 1.01 (s, 3H), 0.93 (s, 3H), 0.88 (s, 3H); m/z 603.4 (M+1).

Compound TX64056:

A mixture of compound TX63762 (40.3 mg, 0.0775 mmol), TEA (0.04 mL, 0.3 mmol), DMAP (18.4 mg, 0.151 mmol), methoxyamine hydrochloride (26.6 mg, 0.318 mmol) and $CH_2Cl_2$ (2 mL) was stirred at room temperature for 15 min. EDCI (30.8 mg, 0.161 mmol) was added, and the reaction was stirred at room temperature for 20 h. The resultant mixture was diluted with EtOAc, washed with 1 N HCl and brine, dried with $Na_2SO_4$, and concentrated. The residue was purified by flash chromatography (silica gel, 0% to 100% EtOAc in hexanes) to give compound TX64056 (24.1 mg, 57%) as a white solid: $^1$H NMR (400 MHz, $CDCl_3$) δ 8.04 (s, 1H), 5.97 (s, 1H), 3.76 (s, 3H), 3.09 (d, 1H, J=4.5 Hz), 2.23 (m, 2H), 2.04 (m, 2H), 1.67 (m, 10H), 1.52 (s, 3H), 1.50 (s, 3H), 1.26 (s, 3H), 1.24 (m, 4H), 1.18 (s, 3H), 1.03 (m, 2H), 1.00 (s, 3H), 0.92 (s, 3H), 0.88 (s, 3H); m/z 549.3 (M+1).

Compound TX63770:

A mixture of compound TX63762 (108.4 mg, 0.209 mmol), TEA (0.06 mL, 0.4 mmol), DMAP (49.8 mg, 0.408 mmol), methylamine hydrochloride (29.3 mg, 0.434 mmol) and $CH_2Cl_2$ (3 mL) was stirred at room temperature. EDCI (78.4 mg, 0.409 mmol) was added, and the reaction was stirred at room temperature for 19 h. The resultant mixture was diluted with EtOAc, washed with 1 N HCl and brine, dried with $Na_2SO_4$, and concentrated. The residue was purified by flash chromatography (silica gel, 0% to 100% EtOAc in hexanes) to give compound TX63770 (90.1 mg, 81%) as a white solid: $^1$H NMR (400 MHz, $CDCl_3$) δ 8.04 (s, 1H), 5.96 (s, 1H), 5.44 (s, 1H), 3.09 (d, 1H, J=4.7 Hz), 2.80 (d, 3H, J=4.8 Hz), 2.22 (td, 1H, J=4.3, 13.5 Hz), 2.13 (t, 2H, J=8.2 Hz), 1.67 (m, 11H), 1.53 (s, 3H), 1.50 (s, 3H), 1.26 (s, 3H), 1.24 (m, 4H), 1.18 (s, 3H), 1.02 (m, 2H), 1.00 (s, 3H), 0.92 (s, 3H), 0.87 (s, 3H); m/z 533.3 (M+1).

Compound TX63768:

A mixture of compound TX63762 (77.5 mg, 0.149 mmol), TEA (0.04 mL, 0.3 mmol), DMAP (35.5 mg, 0.291 mmol), ethylamine hydrochloride (25 mg, 0.31 mmol) and $CH_2Cl_2$ (2 mL) was stirred at room temperature for 30 min. EDCI (55.5 mg, 0.290 mmol) was added, and the reaction was stirred at room temperature for 17 h. The resultant mixture was diluted with $CH_2Cl_2$, washed with 1 N HCl and brine, dried with $Na_2SO_4$, and concentrated. The residue was purified by flash chromatography (silica gel, 0% to 100% EtOAc in hexanes) to give compound TX63768 (56.6 mg, 70%) as a white solid: $^1$H NMR (400 MHz, $CDCl_3$) δ 8.02 (s, 1H), 5.96 (s, 1H), 5.34 (s, 1H), 3.27 (dq, 2H, J=5.1, 7.1 Hz), 3.10 (d, 1H, J=4.6 Hz), 2.24 (td, 1H, J=4.0, 13.1 Hz), 2.12 (t, 2H, J=8.1 Hz), 1.68 (m, 11H), 1.50 (s, 3H), 1.48 (s, 3H), 1.26 (s, 3H), 1.24 (m, 4H), 1.18 (s, 3H), 1.14 (t, 3H, J=7.3 Hz), 1.03 (m, 2H), 1.02 (s, 3H), 0.94 (s, 3H), 0.89 (s, 3H); m/z 547.4 (M+1).

Compound TX63764:

A mixture of compound TX63762 (75.9 mg, 0.147 mmol), TEA (0.04 mL, 0.3 mmol), DMAP (35.9 mg, 0.294 mmol), 2,2,2-trifluoroethylamine hydrochloride (39.1 mg, 0.289 mmol) and $CH_2Cl_2$ (2 mL) was stirred at room temperature for 10 min. EDCI (56.8 mg, 0.296 mmol) was added, and the reaction was stirred at room temperature for 17 h. The resultant mixture was diluted with $CH_2Cl_2$, washed with 1 N HCl and brine, dried with $Na_2SO_4$, and concentrated. The residue was purified by flash chromatography (silica gel, 0% to 100% EtOAc in hexanes) to give compound TX63764 (66.4 mg, 76%) as a white solid: $^1$H NMR (400 MHz, $CDCl_3$) δ 8.03 (s, 1H), 5.98 (s, 1H), 5.65 (s, 1H), 3.91 (m, 2H), 3.07 (d, 1H, J=4.7 Hz), 2.25 (m, 1H), 2.23 (t, 2H, J=8.1 Hz), 1.71 (m, 11H), 1.52 (s, 3H), 1.51 (s, 3H), 1.26 (s, 3H), 1.26 (m, 4H), 1.19 (s, 3H), 1.04 (m, 2H), 1.03 (s, 3H), 0.94 (s, 3H), 0.89 (s, 3H); m/z 601.3 (M+1).

Compound TX64064:

A mixture of compound TX63762 (42.1 mg, 0.0810 mmol), TEA (0.04 mL, 0.3 mmol), DMAP (21.2 mg, 0.165 mmol), isopropylamine (0.02 mL, 0.2 mmol) and $CH_2Cl_2$ (2 mL) was stirred at room temperature for 20 min. EDCI (30.1 mg, 0.157 mmol) was added, and the reaction was stirred at room temperature for 16 h. Additional isopropylamine (0.05 mL, 0.6 mmol) and EDCI (50 mg, 0.26 mmol) were added, and the reaction stirred overnight at room temperature. The resultant mixture was diluted with EtOAc, washed with 1 N HCl and brine, dried with $Na_2SO_4$, and concentrated. The residue was purified by flash chromatography (silica gel, 0% to 100% EtOAc in hexanes) and was then purified by additional flash chromatography (silica gel, 0% to 100% EtOAc in hexanes, each containing 0.5% TEA) to give compound TX64064 (10.2 mg, 22%) as a white solid: $^1$H NMR (400 MHz, $CDCl_3$) δ 8.04 (s, 1H), 5.96 (s, 1H), 5.23 (d, 1H, J=8.0 Hz), 4.06 (m, 1H), 3.10 (d, 1H, J=4.6 Hz), 2.22 (td, 1H, J=4.5, 13.1 Hz), 2.09 (t, 2H, J=8.1 Hz), 1.68 (m, 11H), 1.53 (s, 3H), 1.50 (s, 3H), 1.26 (s, 3H), 1.24 (m, 4H), 1.18 (s, 3H), 1.14 (m, 6H), 1.02 (m, 2H), 1.00 (s, 3H), 0.92 (s, 3H), 0.88 (s, 3H); m/z 561.3 (M+1).

Compound TX64065:

A mixture of compound TX63762 (50.8 mg, 0.0977 mmol), TEA (0.05 mL, 0.4 mmol), DMAP (36.7 mg, 0.300 mmol), tert-butylamine (0.06 mL, 0.6 mmol) and $CH_2Cl_2$ (2 mL) was stirred at room temperature for 15 min. EDCI (59.2 mg, 0.309 mmol) was added, and the reaction was stirred at room temperature for 17 h. The resultant mixture was diluted with EtOAc, washed with 1 N HCl and brine, dried with $Na_2SO_4$, and concentrated. The residue was purified by flash chromatography (silica gel, 0% to 100% EtOAc in hexanes) to give compound TX64065 (16.1 mg, 29%) as a white solid: $^1$H NMR (400 MHz, CDCl$_3$) δ 8.04 (s, 1H), 5.96 (s, 1H), 5.24 (s, 1H), 3.08 (d, 1H, J=4.6 Hz), 2.22 (td, 1H, J=4.6, 13.2 Hz), 2.05 (t, 2H, J=8.1 Hz), 1.67 (m, 11H), 1.53 (s, 3H), 1.50 (s, 3H), 1.34 (s, 9H), 1.26 (s, 3H), 1.24 (m, 4H), 1.18 (s, 3H), 1.01 (m, 2H), 1.00 (s, 3H), 0.92 (s, 3H), 0.87 (s, 3H); m/z 575.4 (M+1).

Compound TX64057:

A mixture of compound TX63762 (40.4 mg, 0.0777 mmol), TEA (0.04 mL, 0.3 mmol), DMAP (19.3 mg, 0.158 mmol), cyclohexylamine (0.04 mL, 0.4 mmol) and CH$_2$Cl$_2$ (2 mL) was stirred at room temperature for 15 min. EDCI (29.8 mg, 0.155 mmol) was added, and the reaction was stirred at room temperature for 21 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give compound TX64057 (14.7 mg, 32%) as a white solid: $^1$H NMR (400 MHz, CDCl$_3$) δ 8.04 (s, 1H), 5.96 (s, 1H), 5.27 (d, 1H, J=8.2 Hz), 3.74 (m, 1H), 3.10 (d, 1H, J=4.6 Hz), 2.22 (td, 1H, J=4.5, 13.1 Hz), 2.10 (t, 2H, J=8.1 Hz), 1.45 (m, 27H), 1.52 (s, 3H), 1.50 (s, 3H), 1.26 (s, 3H), 1.18 (s, 3H), 1.00 (s, 3H), 0.92 (s, 3H), 0.88 (s, 3H); m/z 601.4 (M+1).

Compound TX64059:

A mixture of compound TX63762 (40.3 mg, 0.0775 mmol), TEA (0.04 mL, 0.3 mmol), DMAP (19.3 mg, 0.158 mmol), aniline (0.02 mL, 0.2 mmol) and CH$_2$Cl$_2$ (2 mL) was stirred at room temperature for 20 min. EDCI (30.5 mg, 0.159 mmol) was added, and the reaction was stirred at room temperature for 16 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give compound TX64059 (32.6 mg, 71%) as a white solid: $^1$H NMR (400 MHz, CDCl$_3$) δ 8.05 (s, 1H), 7.49 (d, 2H, J=8.0 Hz), 7.32 (t, 2H, J=7.8 Hz), 7.16 (s, 1H), 7.11 (t, 1H, J=7.4 Hz), 5.98 (s, 1H), 3.09 (d, 1H, J=4.6 Hz), 2.34 (t, 2H, J=8.2 Hz), 2.28 (td, 1H, J=4.6, 13.1 Hz), 1.73 (m, 11H), 1.52 (s, 3H), 1.49 s, 3H), 1.27 (m, 4H), 1.26 (s, 3H), 1.18 (s, 3H), 1.06 (m, 2H), 1.02 (s, 3H), 0.94 (s, 3H), 0.89 (s, 3H); m/z 595.4 (M+1).

Compound TX64075:

A mixture of compound TX63762 (49.2 mg, 0.0947 mmol), TEA (0.04 mL, 0.3 mmol), DMAP (23.5 mg, 0.192 mmol), benzylamine (0.02 mL, 0.2 mmol) and CH$_2$Cl$_2$ (2 mL) was stirred at room temperature for 15 min. EDCI (37.2 mg, 0.194 mmol) was added, and the reaction was stirred overnight at room temperature. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give compound TX64075 (14.4 mg, 25%) as a white solid: $^1$H NMR (400 MHz, CDCl$_3$) δ 8.04 (s, 1H), 7.31 (m, 5H), 5.97 (s, 1H), 5.69 (s, 1H), 4.43 (m, 2H), 3.10 (d, 1H, J=4.6 Hz), 2.24 (td, 1H, J=4.1, 13.4 Hz), 2.18 (t, 2H, J=8.2 Hz), 1.69 (m, 11H), 1.52 (s, 3H), 1.50 (s, 3H), 1.26 (s, 3H), 1.25 (m, 4H), 1.18 (s, 3H), 1.02 (m, 2H), 1.01 (s, 3H), 0.91 (s, 3H), 0.87 (s, 3H); m/z 609.4 (M+1).

Compound TX64060:

A mixture of compound TX63762 (43.9 mg, 0.0845 mmol), TEA (0.04 mL, 0.3 mmol), DMAP (18.8 mg, 0.154 mmol), dimethylamine hydrochloride (13.4 mg, 0.164 mmol) and CH$_2$Cl$_2$ (2 mL) was stirred at room temperature for 20 min. EDCI (30.9 mg, 0.161 mmol) was added, and the reaction was stirred at room temperature for 16 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give compound TX64060 (35.6 mg, 77%) as a white solid: $^1$H NMR (400 MHz, CDCl$_3$) δ 8.04 (s, 1H), 5.96 (s, 1H), 3.10 (d, 1H, J=4.6 Hz), 3.03 (s, 3H), 2.94 (s, 3H), 2.34 (ddd, 1H, J=5.4, 11.3, 15.7 Hz), 2.22 (m, 2H), 1.67 (m, 11H), 1.51 (s, 3H), 1.49 (s, 3H), 1.26 (s, 3H), 1.26 (m, 4H), 1.18 (s, 3H), 1.02 (m, 2H), 1.01 (s, 3H), 0.93 (s, 3H), 0.88 (s, 3H); m/z 547.3 (M+1).

Compound TX63950:

A mixture of compound TX63762 (521 mg, 1.00 mmol), TEA (0.42 mL, 3.0 mmol), DMAP (250 mg, 2.05 mmol), azetidine hydrochloride (188 mg, 2.01 mmol) and CH$_2$Cl$_2$ (20 mL) was stirred at room temperature for 15 min. EDCI (391 mg, 2.04 mmol) was added, and the reaction was stirred at room temperature for 25 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give compound TX63950 (394.6 mg, 71%) as an off-white solid: $^1$H NMR (400 MHz, CDCl$_3$) δ 8.03 (s, 1H), 5.96 (s, 1H), 4.15 (m, 2H), 3.99 (t, 2H, J=7.7 Hz), 3.10 (d, 1H, J=4.6 Hz), 2.26 (m, 3H), 1.77 (m, 13H), 1.53 (s, 3H), 1.49 (s, 3H), 1.26 (s, 3H), 1.24 (m, 4H), 1.17 (s, 3H), 1.01 (m, 2H), 1.00 (s, 3H), 0.93 (s, 3H), 0.88 (s, 3H); m/z 559.3 (M+1).

Compound TX63949:

A mixture of compound TX63762 (520 mg, 1.00 mmol), TEA (0.42 mL, 3.0 mmol), DMAP (241 mg, 1.97 mmol), pyrrolidine (0.17 mL, 2.06 mmol) and CH$_2$Cl$_2$ (20 mL) was stirred at room temperature for 15 min. EDCI (381 mg, 1.99 mmol) was added, and the reaction was stirred at room temperature for 25 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give TX63949 (266.9 mg, 47%) as an off-white solid: $^1$H NMR (400 MHz, CDCl$_3$) δ 8.04 (s, 1H), 5.96 (s, 1H), 3.44 (t, 4H, J=6.9 Hz), 3.12 (d, 1H, J=4.7 Hz), 2.22 (m, 3H), 1.71 (m, 15H), 1.53 (s, 3H), 1.49 (s, 3H), 1.26 (s, 3H), 1.26 (m, 4H), 1.18 (s, 3H), 1.03 (m, 2H), 1.01 (s, 3H), 0.96 (s, 3H), 0.88 (s, 3H); m/z 573.4 (M+1).

Compound TX63763:

A mixture of compound TX63762 (77.2 mg, 0.149 mmol), TEA (0.04 mL, 0.3 mmol), DMAP (35.6 mg, 0.291 mmol), morpholine (25 μL, 0.29 mmol) and CH$_2$Cl$_2$ (2 mL) was stirred at room temperature for 10 min. EDCI (57.8 mg, 0.301 mmol) was added, and the reaction was stirred at room temperature for 16 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give compound TX63763 (66.1 mg, 82%) as a white solid: $^1$H NMR (400 MHz, CDCl$_3$) δ 8.04 (s, 1H), 5.97 (s, 1H), 3.68 (m, 4H), 3.60 (m, 2H), 3.48 (m, 2H), 3.08 (d, 1H, J=4.6 Hz), 2.33 (ddd, 1H, J=5.4, 11.3, 16.4 Hz), 2.21 (m, 2H), 1.69 (m, 11H), 1.50 (s, 3H), 1.49 (s, 3H), 1.26 (s, 3H), 1.26 (m, 4H), 1.18 (s, 3H), 1.04 (m, 2H), 1.01 (s, 3H), 0.93 (s, 3H), 0.88 (s, 3H); m/z 589.4 (M+1).

Compound TX64045:

A mixture of compound TX63762 (39.2 mg, 0.0754 mmol), TEA (0.03 mL, 0.2 mmol), DMAP (19.5 mg, 0.160 mmol), acetic hydrazide (14.5 mg, 0.196 mmol) and CH$_2$Cl$_2$ (2 mL) was stirred at room temperature for 30 min. EDCI (31.8 mg, 0.166 mmol) was added, and the reaction was stirred at room temperature for 18 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give compound TX64045 (19.7 mg, 45%) as a white solid: $^1$H NMR (400 MHz, CDCl$_3$) δ 8.04 (s, 1H), 8.00 (s, 1H), 7.96 (s, 1H), 5.98 (s, 1H), 3.07 (d, 1H, J=4.6 Hz), 2.24 (m, 3H), 2.06 (s, 3H), 1.68 (s, 11H), 1.51 (s, 3H), 1.50 (s, 3H), 1.25 (m, 4H), 1.26 (s, 3H), 1.18 (s, 3H), 1.03 (m, 2H), 1.01 (s, 3H), 0.92 (s, 3H), 0.88 (s, 3H); m/z 576.3 (M+1).

Compound TX64049:

A mixture of compound TX63762 (40.3 mg, 0.0775 mmol), TEA (0.03 mL, 0.2 mmol), DMAP (17.9 mg, 0.147 mmol), 3,3-difluoropyrrolidine hydrochloride (23.2 mg, 0.162 mmol) and CH$_2$Cl$_2$ (2 mL) was stirred at room temperature for 15 min. EDCI (29.3 mg, 0.153 mmol) was added, and the reaction was stirred at room temperature for 18 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give compound TX64049 (27.9 mg, 59%) as a white solid: $^1$H NMR (400 MHz, CDCl$_3$) δ 8.04 (s, 1H), 5.97 (s, 1H), 3.75 (m, 4H), 3.09 (t, 1H, J=4.4 Hz), 2.32 (m, 5H), 1.70 (m, 11H), 1.52 (s, 3H), 1.50 (s, 3H), 1.26 (s, 3H), 1.26 (m, 4H), 1.18 (s, 3H), 1.03 (m, 2H), 1.01 (s, 3H), 0.93 (s, 3H), 0.88 (s, 3H); m/z 609.3 (M+1).

Compound TX64047:

A mixture of compound TX63762 (40.2 mg, 0.0774 mmol), TEA (0.03 mL, 0.2 mmol), DMAP (17.9 mg, 0.147 mmol), (S)-3-hydroxypyrrolidine hydrochloride (34.1 mg, 0.276 mmol) and CH$_2$Cl$_2$ (2 mL) was stirred at room temperature for 15 min. EDCI (28.5 mg, 0.149 mmol) was added, and the reaction was stirred at room temperature for 18 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give compound TX64047 (20.8 mg, 46%) as a white solid: $^1$H NMR (400 MHz, CDCl$_3$) δ [8.04 (s), 8.03 (s) (1:1, 1H)], [5.97 (s), 5.96 (s) (1:1, 1H)], 4.52 (s, 1H), 3.58 (m, 4H), [3.12 (d, J=4.5 Hz), 3.09 (d, J=4.5 Hz) (1:1, 1H)], 1.87 (m, 17H), [1.53 (s), 1.52 (s) (1:1, 3H)], [1.49 (s), 1.50 (s) (1:1, 3H)], 1.26 (s, 3H), 1.18 (s, 3H), 1.07 (m, 6H), 1.00 (s, 3H), [0.95 (s), 0.93 (s) (1:1, 3H)], 0.88 (s, 3H); m/z 589.3 (M+1).

Compound TX64048:

A mixture of TX63762 (40.1 mg, 0.0772 mmol), TEA (0.03 mL, 0.2 mmol), DMAP (19.2 mg, 0.157 mmol), 4-hydroxypiperidine (16.5 mg, 0.163 mmol) and CH$_2$Cl$_2$ (2 mL) was stirred at room temperature for 15 min. EDCI (28.4 mg, 0.148 mmol) was added, and the reaction was stirred at room temperature for 18 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give compound TX64048 (23.9 mg, 51%) as a white solid: $^1$H NMR (400 MHz, CDCl$_3$) δ 8.04 (s, 1H), 5.97 (s, 1H), 4.10 (m, 1H), 3.95 (m, 1H), 3.72 (m, 2H), 3.22 (m, 2H), 3.09 (s, 1H), 2.29 (m, 5H), 1.69 (m, 13H), 1.51 (s, 3H), 1.50 (s, 3H), 1.26 (m, 4H), 1.26 (s, 3H), 1.18 (s, 3H), 1.03 (m, 2H), 1.01 (s, 3H), 0.93 (s, 3H), 0.88 (s, 3H); m/z 603.4 (M+1).

Compound TX64068:

A mixture of compound TX63762 (51.3 mg, 0.0987 mmol), TEA (0.05 mL, 0.4 mmol), DMAP (37.2 mg, 0.304 mmol), 2-aminopyridine (52.5 mg, 0.558 mmol) and CH$_2$Cl$_2$ (2 mL) was stirred at room temperature for 15 min. EDCI (59.2 mg, 0.309 mmol) was added, and the reaction was stirred at room temperature for 17 h. The resultant mixture was directly purified by flash chromatography (silica gel, 0% to 100% EtOAc in hexanes, each containing 0.5% TEA), then was purified by additional flash chromatography (C$_{18}$ silica gel, 0% to 100% MeCN in water) to give compound TX64068 (7.0 mg, 12%) as a white solid: $^1$H NMR (400 MHz, CDCl$_3$) δ 8.26 (d, 1H, J=4.8 Hz), 8.16 (d, 1H, J=8.5 Hz), 8.04 (s, 1H), 7.83 (s, 1H), 7.69 (m, 1H), 7.04 (dd, 1H, J=4.8, 7.3 Hz), 5.98 (s, 1H), 3.10 (d, 1H, J=4.7 Hz), 2.36 (m, 2H), 2.26 (td, 1H, J=4.7, 13.4 Hz), 1.75 (m, 11H), 1.52 (s, 3H), 1.50 (s, 3H), 1.26 (m, 4H), 1.26 (s, 3H), 1.18 (s, 3H), 1.05 (m, 2H), 1.02 (s, 3H), 0.94 (s, 3H), 0.89 (s, 3H); m/z 596.4 (M+1).

Compound TX64044:

A mixture of compound TX63762 (39.7 mg, 0.0764 mmol), TEA (0.03 mL, 0.2 mmol), DMAP (20.3 mg, 0.166 mmol), 3-oxetanamine hydrochloride (17.0 mg, 0.155 mmol) and CH$_2$Cl$_2$ (2 mL) was stirred at room temperature for 30 min. EDCI (30.6 mg, 0.160 mmol) was added, and the reaction was stirred at room temperature for 18 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give compound TX64044 (28.5 mg, 65%) as a white solid: $^1$H NMR (400 MHz, CDCl$_3$) δ 8.04 (s, 1H), 5.97 (s, 1H), 5.94 (s, 1H), 6.74 (m, 1H), 4.92 (dt, 2H, J=2.3, 7.1 Hz), 4.48 (dt, 2H, J=2.9, 6.4 Hz), 3.06 (d, 1H, J=4.6 Hz), 2.20 (m, 3H), 1.69 (m, 11H), 1.51 (s, 3H), 1.50 (s, 3H), 1.26 (s, 3H), 1.25 (m, 4H), 1.18 (s, 3H), 1.02 (m, 2H), 1.00 (s, 3H), 0.93 (s, 3H), 0.88 (s, 3H); m/z 575.3 (M+1).

Compound TX64052:

A mixture of compound TX63762 (71 mg, 0.137 mmol), TEA (0.06 mL, 0.4 mmol), DMAP (46.2 mg, 0.378 mmol), glycine methyl ester hydrochloride (33.9 mg, 0.270 mmol) and CH$_2$Cl$_2$ (3 mL) was stirred at room temperature for 15 min. EDCI (78.1 mg, 0.407 mmol) was added, and the reaction was stirred at room temperature for 16 h. The resultant mixture was diluted with EtOAc, washed with 1 N HCl and brine, dried with Na$_2$SO$_4$, and concentrated. The residue was purified by flash chromatography (silica gel, 0% to 100% EtOAc in hexanes) to give compound TX64052 (52.0 mg, 64%) as a white solid: $^1$H NMR (400 MHz, CDCl$_3$) δ 8.04 (s, 1H), 5.97 (s, 1H), 5.95 (s, 1H), 4.04 (dd, 2H, J=5.1, 9.2 Hz), 3.77 (s, 3H), 3.08 (d, 1H, J=4.7 Hz), 2.22 (m, 3H), 1.67 (m, 11H), 1.52 (s, 3H), 1.50 (s, 3H), 1.26 (s, 3H), 1.25 (m, 4H), 1.18 (s, 3H), 1.03 (m, 2H), 1.00 (s, 3H), 0.93 (s, 3H), 0.88 (s, 3H); m/z 591.3 (M+1).

Compound TX64054:

A mixture of compound TX64052 (20.9 mg, 0.0354 mmol), 1 N HCl (0.6 mL), and MeCN (1.2 mL) was heated to 55° C. for 22 h. The resultant mixture was diluted with EtOAc, washed with brine, dried with Na$_2$SO$_4$, and concentrated. The residue was purified by flash chromatography (silica gel, 0% to 100% EtOAc in hexanes, each with 0.5% HOAc) to give compound TX64054 (14.6 mg, 71%) as a white solid: $^1$H NMR (400 MHz, CDCl$_3$) δ 8.04 (s, 1H), 6.17 (s, 1H), 5.99 (s, 1H), 4.09 (dd, 2H, J=5.0, 9.7 Hz), 3.07 (d, 1H, J=4.6 Hz), 2.24 (m, 3H), 1.68 (m, 11H), 1.51 (s, 3H), 1.50 (s, 3H), 1.26 (s, 3H), 1.23 (m, 4H), 1.18 (s, 3H), 1.03 (m, 2H), 1.01 (s, 3H), 0.91 (s, 3H), 0.88 (s, 3H); m/z 577.3 (M+1).

Compound TX64124:

A mixture of compound TX63762 (47.8 mg, 0.0920 mmol), TEA (0.04 mL, 0.29 mmol), DMAP (23.5 mg, 0.192 mmol), 4-Boc-piperazine (36.3 mg, 0.195 mmol) and CH$_2$Cl$_2$ (2 mL) was stirred at room temperature for 15 min. EDCI (36.8 mg, 0.192 mmol) was added, and the reaction was stirred at room temperature for 16 h. The resultant mixture was diluted with EtOAc, washed with 1 N HCl and brine, dried with $Na_2SO_4$, and concentrated. The residue was purified by flash chromatography (silica gel, 0% to 100% EtOAc in hexanes) to give compound TX64124 (55.9 mg, 88%) as a white solid: $^1$H NMR (400 MHz, $CDCl_3$) δ 8.04 (s, 1H), 5.97 (s, 1H), 3.57 (m, 2H), 3.42 (m, 6H), 3.08 (d, 1H, J=4.6 Hz), 2.35 (m, 1H), 2.23 (m, 2H), 1.68 (m, 11H), 1.50 (s, 3H), 1.49 (s, 3H), 1.47 (s, 9H), 1.27 (m, 4H), 1.26 (s, 3H), 1.18 (s, 3H), 1.01 (s, 3H), 1.00 (m, 2H), 0.93 (s, 3H), 0.88 (s, 3H); m/z 588.4 (M-Boc+H+1).

Compound TX64135:

HCl (4.0 M in 1,4-dioxane, 0.2 mL) was added to a room temperature solution of compound TX64124 (49 mg, 0.071 mmol) in $CH_2Cl_2$ (5 mL), and the mixture was stirred at room temperature. Additional HCl solution (4.0 M in 1,4-dioxane) was added after 17 h (0.5 mL), 20 h (0.5 mL) and 2 d (2.0 mL). The resultant mixture was diluted with EtOAc, washed with 1 N NaOH and brine, dried with $Na_2SO_4$, and concentrated to give compound TX64135 (14.4 mg, 35%) as an off-white solid: $^1$H NMR (400 MHz, $CDCl_3$) δ 8.04 (s, 1H), 5.97 (s, 1H), 3.62 (m, 5H), 3.09 (d, 1H, J=4.7 Hz), 2.86 (app. td, 4H, J=5.1, 17.7 Hz), 2.34 (m, 1H), 2.22 (m, 2H), 1.68 (m, 11H), 1.51 (s, 3H), 1.49 (s, 3H), 1.26 (s, 3H), 1.24 (m, 4H), 1.18 (s, 3H), 1.03 (m, 2H), 1.01 (s, 3H), 0.93 (s, 3H), 0.88 (s, 3H); m/z 588.4 (M+1).

Compound TX64074:

A mixture of compound TX63762 (51.9 mg, 0.0999 mmol), $NH_4Cl$ (18.0 mg, 0.337 mmol), EDCI (28.7 mmol, 0.150 mmol), $HOBt.xH_2O$ (23 mg, 0.17 mmol), DIEA (0.03 mL, 0.2 mmol) and DMF (1 mL) was stirred at room temperature for 17 h. The resultant mixture was diluted with EtOAc, washed with 1 N HCl and brine, dried with $Na_2SO_4$, and concentrated. The residue was purified by flash chromatography (silica gel, 0% to 100% EtOAc in hexanes, each containing 0.5% TEA) to give compound TX64074 (25.3 mg, 49%) as a white solid: $^1$H NMR (400 MHz, $CDCl_3$) δ 8.04 (s, 1H), 5.97 (s, 1H), 5.39 (s, 1H), 5.24 (s, 1H), 3.08 (d, 1H, J=4.7 Hz), 2.21 (m, 3H), 1.70 (m, 11H), 1.51 (s, 3H), 1.50 (s, 3H), 1.26 (s, 3H), 1.24 (m, 4H), 1.18 (s, 3H), 1.03 (m, 2H), 1.01 (s, 3H), 0.93 (s, 3H), 0.88 (s, 3H); m/z 519.3 (M+1).

Compound 13:

Compound 13 was synthesized as reported in U.S. Pat. No. 7,943,778, which issued on May 17, 2011, the entirety of which is incorporated herein by reference.

Compound 14:

The flask containing a suspension of compound 13 (4.81 g, 10.1 mmol), Pd/C (10% w/w, 642 mg), EtOAc (100 mL), and $CH_2Cl_2$ (100 mL) was thoroughly purged with $N_2$, followed by $H_2$. The resultant mixture was stirred vigorously for 2 h, sparged with $N_2$ for ~2 h, stirred overnight at room temperature, filtered through a plug of celite (3 cm) eluting with $CH_2Cl_2$ (200 mL), and concentrated to give compound 14 (5.0 g) as a pale yellow foam that was used without further purification: m/z 480.3 (M+1).

Compound 15:

A suspension of compound 14 (all above obtained, ≤10.1 mmol), HBr (48% w/w aq., 0.49 mL, 4.4 mmol), and MeCN was heated to 35° C. for 30 min. $Br_2$ (0.62 mmol, 12.1 mmol) was added, and the resultant mixture was heated to 35° C. for an additional 17 h. The solution was cooled to room temperature, 10% $Na_2SO_3$ (50 mL) added, and the biphasic mixture was stirred for 15 min at room temperature. The mixture was diluted with EtOAc. The organic fraction was separated, washed with a 1:1 mixture of 10% $Na_2SO_3$ and sat. $NaHCO_3$ and brine, dried with $Na_2SO_4$, and concentrated to give compound 15 (5.1 g) as a yellow foam that was used without further purification: m/z 478.3 (M+1).

Compound 16:

NaOMe (25% w/w in MeOH, 3.00 mL, 13.1 mmol) was added to a suspension of compound 15 (all above obtained, ≤10.1 mmol) in MeOH (100 mL), and the resultant mixture heated to 50° C. for 2 h. The yellow solution was cooled to room temperature, diluted with MTBE, washed with 1 M HCl and brine, dried with $Na_2SO_4$, and concentrated to give compound 16 (5.15 g) as a yellow foam that was used without further purification: m/z 478.3 (M+1).

Compound TX63403:

A solution of 1,3-dibromo-5,5-dimethylhydantoin (1.445 g, 5.05 mmol) in DMF (12 mL) was added over 5 min to a 0° C. solution of 30 (all above obtained, ≤10.1 mmol) in DMF (40 mL). The vial containing the DBDMH solution was washed with an addition 8 mL of DMF, and that solution was added to the reaction. After 1 h at 0° C., pyridine (2.45 mL, 30.3 mmol) was added, and the reaction was heated to 55° C. for 4 h. The resultant solution was cooled to room temperature, diluted with EtOAc, washed with 10% $Na_2SO_3$, water, 1 N HCl, and brine, dried with $Na_2SO_4$, and concentrated. The residue was purified by flash chromatography (silica gel, 0% to 42% EtOAc in hexanes), and the resultant product was triturated with EtOH (50 mL) at 50° C. for 30 min to give compound TX63403 (3.01 g, 63% from 13) as a white solid: $^1$H NMR (500 MHz, $CDCl_3$) δ 8.05 (s, 1H), 5.97 (s, 1H), 3.02 (d, 1H, J=4.7 Hz), 2.23 (td, 1H, J=4.3, 13.5 Hz), 1.78 (m, 6H), 1.54 (m, 3H), 1.50 (s, 3H), 1.46 (s, 3H), 1.40 (m, 1H), 1.26 (s, 3H), 1.22 (m, 5H), 1.18 (s, 3H), 1.03 (m, 2H), 1.00 (s, 3H), 0.92 (s, 3H), 0.87 (s, 3H), 0.83 (t, 3H, J=7.4 Hz); m/z 476.3 (M+1).

Compound TX63868:

Compound TX63355 (500 mg, 1.05 mmol) and 1,1'-carbonyldiimidazole (221 mg, 1.36 mmol) were dissolved in MeCN (10 mL). The reaction was heated at reflux for 5 h and was then cooled to room temperature. The precipitate was collected by filtration and was then washed with MeCN and dried under vacuum to give compound TX63868 (446 mg, 75%) as a white solid: $^1$H NMR (400 mHz, $CDCl_3$) δ 8.15 (s, 1H), 8.03 (s, 1H), 7.42 (s, 1H), 7.10 (s, 1H), 6.00 (s, 1H), 4.43 (d, 1H, J=10.8 Hz), 4.36 (d, 1H, J=10.8 Hz), 3.00 (d, 1H, J=4.7 Hz), 2.44 (m, 1H), 2.00 (ddd, 1H, J=4.3, 13.9, 13.9 Hz), 1.72-1.90 (m, 7H), 1.58 (m, 1H), 1.52 (s, 3H), 1.51 (s, 3H), 1.26 (s, 3H), 1.18 (s, 3H), 1.15-1.44 (m, 6H), 1.05 (s, 3H), 0.97 (s, 3H), 0.91 (s, 3H); m/z 572.3 (M+1).

Compound TX63926:

A mixture of compound TX63355 (200 mg, 0.42 mmol), 4-morpholinecarbonyl chloride (0.15 mL, 1.28 mmol), DMAP (5 mg, 0.041 mmol), and pyridine (1 mL) was stirred at rt for 30 min, then at 90° C. for 18 h. The reaction was cooled to rt, and $Ac_2O$ (0.2 mL) was added. After the reaction was stirred for 30 min, aq. $NaHCO_3$ solution was added. The reaction was stirred for another 30 min and was then extracted with EtOAc. The combined organic extracts were washed with 1 N HCl and then NaHCO solution, dried with $Na_2SO_4$, and concentrated. The residue was purified by column chromatography (silica gel, 0% to 45% EtOAc in hexanes) to give compound TX63926 (122 mg, 49%) as a white foam: $^1$H NMR δ 8.06 (s, 1H), 6.00 (s, 1H), 4.20 (d, 1H, J=11.0 Hz), 4.04 (d, 1H, J=11.0 Hz), 3.69 (bs, 4H), 3.51 (bs, 4H), 3.07 (d, 1H, J=4.6 Hz), 2.42 (m, 1H), 1.72-1.98 (m, 7H), 1.61 (m, 1H), 1.53 (s, 3H), 1.52 (s, 3H), 1.49 (m, 1H), 1.28 (s, 3H), 1.20 (s, 3H), 1.08-1.36 (m, 6H), 1.04 (s, 3H), 0.96 (s, 3H), 0.91 (s, 3H); m/z 591.4 (M+1).

Compound TX63927:

A mixture of compound TX63355 (200 mg, 0.42 mmol), 1-pyrrolidinecarbonyl chloride (0.14 mL, 1.27 mmol), DMAP (5 mg, 0.041 mmol) and pyridine (1 mL) was stirred at rt for 30 min, and then at 90° C. for 18 h. The reaction was cooled to rt, and Ac$_2$O (0.2 mL) was added. After the reaction was stirred for 30 min, aq. NaHCO$_3$ solution was added. The reaction was stirred for another 30 min and was then extracted with EtOAc. The combined organic extracts were washed with 1 N HCl and NaHCO$_3$ solution, dried with Na$_2$SO$_4$, and concentrated. The residue was purified by column chromatography (silica gel, 0% to 40% EtOAc in hexanes) to give compound TX63927 (85 mg, 35%) as a white foam: $^1$H NMR δ 8.07 (s, 1H), 5.99 (s, 1H), 4.20 (d, 1H, J=10.9 Hz), 3.94 (d, 1H, J=10.9 Hz), 3.40 (m, 4H), 3.09 (d, 1H, J=4.6 Hz), 2.48 (m, 1H), 1.72-2.00 (m, 11H), 1.60 (m, 1H), 1.53 (s, 3H), 1.52 (s, 3H), 1.49 (m, 1H), 1.28 (s, 3H), 1.20 (s, 3H), 1.08-1.36 (m, 6H), 1.04 (s, 3H), 0.97 (s, 3H), 0.91 (s, 3H); m/z 575.4 (M+1).

Compound TX63930:

A mixture of compound TX63355 (200 mg, 0.42 mmol), ethyl isocyanate (0.33 mL, 4.17 mmol), and toluene (1 mL) was stirred at rt for 30 min, and then at 90° C. for 16 h. The reaction was cooled to rt. and was purified directly by column chromatography (silica gel, 0% to 50% EtOAc ire hexanes) to give compound TX63930 (196 rng, 85% yield) as a white foam: $^1$H NMR δ 8.07 (s, 1H), 6.00 (s, 1H), 4.70 (m, 1H), 4.12 (d, 1H, J=11.0 Hz), 4.00 (d, 1H, J=11.0 Hz), 3.24 (m, 2H), 3.08 (d, 1H, J=4.4 Hz), 2.42 (m, 1H), 1.53 (s, 3H), 1.52 (s, 3H), 1.28 (s, 3H), 1.20 (s, 3H), 1.17 (t, 3H, J=7.3 Hz), 1.08-1.97 (m, 15H), 1.04 (s, 3H), 0.97 (s, 3H), 0.90 (s, 3H); m/z 549.3 (M+1), Compound 17:

LiAlH$_4$ (2.0 M in THF, 100 mL, 200 mmol) was added to a 0° C. solution of oleanolic acid (25.1 g, 55.0 mmol) in THF (1.25 L). The mixture was heated to reflux for 3 h, cooled to room temperature overnight, cooled to 0° C., quenched by the successive addition of water (10.6 mL), 4 M NaOH (10.6 mL) and water (10.6 mL), warmed to room temperature over 15 min, filtered through celite, eluted with MTBE, and concentrated to give compound 17 as a white solid that was used without further purification: m/z 443.4 (M+1).

Compound 18:

A solution of NaOCl (6.0%, 80 mL, 65 mmol) and water (180 mL) was added to a 0° C. biphasic solution of compound 17 (all above obtained, ≤55.0 mmol), NaHCO$_3$ (4.65 g, 55.4 mmol), NaBr (5.68 g, 55.2 mmol), TEMPO (4.30 g, 27.5 mmol), water (360 mL) and CH$_2$Cl$_2$ (1 L) over 1 h. The mixture was warmed to room temperature over 16 h, quenched by the addition of 10% Na$_2$SO$_3$ and stirred for 15 min. The organic fraction was separated, and the aqueous fraction was extracted with CH$_2$Cl$_2$. The combined organic fraction was washed with brine, dried with Na$_2$SO$_4$, and concentrated. The residue was purified by flash chromatography (silica gel, 0% to 15% EtOAc in hexanes, then 10% EtOAc in CH$_2$Cl$_2$) to give compound 18 (19.22 g, 79% from oleanolic acid) as an off-white solid: m/z 441.4 (M+1).

Compound 19:

KOtBu (6.36 g, 56.8 mmol) was added to a room temperature suspension of (methoxymethyl)triphenylphosphonium chloride (23.36 g, 68.14 mmol) in THF (115 mL) and stirred at room temperature for 45 min. A solution of 18 (5.00 g, 11.4 mmol) in THF (85 mL) was added over 10 min to the reaction mixture, and the transfer was completed with THF (30 mL). The reaction was stirred at room temperature for 21 h, then quenched by the addition of H$_2$SO$_4$ (30%, 23 mL), stirred 2 h, diluted with EtOAc and water, and made basic with 4 N NaOH. The organic fraction was separated, washed with brine, dried with Na$_2$SO$_4$, and concentrated. The residue was purified by flash chromatography (silica gel, 0% to 30% EtOAc in hexanes) to give compound 19 (4.93 g, 96%) as a pale yellow solid: m/z 455.4 (M+1).

Compound 20:

NaBH$_4$ (856 mmol, 22.6 mmol) was added to a 0° C. solution of compound 19 (4.93 g, 10.8 mmol) in MeOH/THF (2:1 mixture, 300 mL), and the reaction was allowed to warm to room temperature. After 2 h at room temperature, the mixture was concentrated to reduced volume, diluted with EtOAc, washed with 1 N HCl and brine, dried with Na$_2$SO$_4$, and concentrated to give compound 20 (6 g, quantitative) as a white solid: m/z 457.4 (M+1).

Compound 21:

A solution of 20 (all above obtained, ≤10.8 mmol), Ac$_2$O (8.2 mL, 87 mmol), pyridine (10.5 mL, 130 mmol), and DMAP (133 mg, 1.09 mmol) in CH$_2$Cl$_2$ (225 mL) was stirred at room temperature. Additional Ac$_2$O (4.1 mL, 43 mmol), pyridine (5.25 mL, 64.9 mmol), and DMAP (133 mg, 1.09 mmol) were added after 7 h and again after an additional 16 h. The reaction was stirred an additional 3 d, then diluted with CH$_2$Cl$_2$, washed with 1 N HCl, saturated NaHCO$_3$ and brine, dried with Na$_2$SO$_4$, and concentrated. The residue was purified by flash chromatography (silica gel, 0% to 30% EtOAc in hexanes) to give compound 21 (4.40 g, 75% from 19) as a white foam solid.

Compound 22:

AcOOH (39% in AcOH, 2.1 mL, 12.4 mmol) was added to a 50° C. suspension of 21 (4.40 g, 8.14 mmol) and Na$_2$CO$_3$ (1.13 g, 10.7 mmol) in AcOH (81 mL). Additional AcOOH (0.84 mL, 5.0 mmol) was added after 17 h and again (0.21 mL, 1.2 mmol) after an additional 8 h. The reaction was stirred at 50° C. for an additional 18 h, quenched by the addition of excess Na$_2$SO$_3$, stirred 15 min, diluted with toluene, and concentrated to dryness. The residue was dissolved in CH$_2$Cl$_2$, washed with water, saturated NaHCO$_3$ and brine, dried with Na$_2$SO$_4$, and concentrated to give compound 22 (4.36 g, 96%) as a white solid: m/z 557.4 (M+1).

Compound 23:

Br$_2$ (0.60 mL, 12 mmol) was added to a 35° C. suspension of compound 22 (5.41 g, 9.72 mmol) and HCl (4.0 M in 1,4-dioxane, 0.97 mL, 3.9 mmol) in MeCN (96 mL). The mixture was stirred overnight between room temperature and 35° C. The mixture was heated to 35° C., and additional Bra (0.15 mL, 2.9 mmol) was added and again added (0.30 mL, 5.8 mmol) after an additional 1 h. The reaction was stirred at 35° C. for an additional 1 h, then quenched by the addition of 4% Na$_2$SO$_3$ (100 mL) and stirred at room temperature for 30 min. The organic fraction was washed with saturated NaHCO$_3$ and brine, dried with Na$_2$SO$_4$, and concentrated to give compound 23 as a yellow solid: m/z 555.4 (M+1).

Compound 24:

A solution of compound 23 (all above obtained, ≤9.72 mmol) and concentrated H$_2$SO$_4$ (0.1 mL) in MeOH/THF (1:1 mixture, 200 mL) was heated to 35° C. for 1 h. Additional H$_2$SO$_4$ (0.9 ml) was added, and the reaction was then brought to reflux for 19 h. The mixture was concentrated to reduced volume, then diluted with EtOAc, washed with 1 N NaOH and brine, dried with Na$_2$SO$_4$, and concentrated. The residue was purified by flash chromatography (silica gel, 0% to 65% EtOAc in CH$_2$Cl$_2$) to give compound 24 (3.41 g, 74% from 22) as a pale-yellow solid: m/z 471.4 (M+1).

Compound 25:

A solution of NaOCl (6%, 6.5 mL, 5.2 mmol) was added to a room temperature solution of compound 24 (1.70 g, 3.61 mmol) in AcOH (27.5 mL), and the reaction mixture was stirred at room temperature for 1.5 h. The reaction was diluted with EtOAc, washed with 10% $Na_2SO_3$ and brine, dried with $Na_2SO_4$, and concentrated. The residue was purified by flash chromatography (silica gel, 0% to 55% EtOAc in $CH_2Cl_2$) to give compound 25 (1.36 g, 80%) as a white solid: m/z 469.3 (M+1).

Compound 26:

NaOMe (25% in MeOH, 6.5 mL) was added to a 0° C. solution of compound 25 (1.36 g, 2.90 mmol) in ethyl formate (16.5 mL). The mixture was stirred at 0° C. for 15 min, then warmed to room temperature. After 7 h the mixture was diluted with EtOAc, washed with 1 N HCl and brine, dried with $Na_2SO_4$, and concentrated to a give compound 26 (plus mixture of formate esters) as a yellow foam: m/z 497.3 (M+1).

Compound 27:

A mixture of compound 26 (all above obtained, ≤2.90 mmol) and $NH_2OH·HCl$ in EtOH/water was heated to 55° C. for 17 h. The resultant mixture was diluted with EtOAc, washed with 1 N HCl and brine, dried with $Na_2SO_4$, and concentrated to give compound 27 as a yellow foam: m/z 494.4 (M+1).

Compound 28:

A solution of 27 (all above obtained, ≤2.90 mmol) and NaOMe (25% in MeOH, 1.7 mL) in MeOH (39 mL) was heated to 55° C. for 6 h. The mixture was cooled to room temperature overnight, acidified with HCl (4 M in 1,4-dioxane, 10 mL), and heated to 55° C. for 7 h. The resultant mixture was diluted with EtOAc, washed with 1 N HCl and brine, dried with $Na_2SO_4$, and concentrated. The residue was purified by flash chromatography (silica gel, 0% to 100% EtOAc in hexanes) to give compound 28 (1.01 g, 71% from 25) as a pale-yellow foam solid: m/z 494.3 (M+1).

Compound TX63608:

A solution of 1,3-dibromo-5,5-dimethylhydantoin (309 mg, 1.08 mmol) in DMF (3 mL) was added to a 0° C. solution of compound 28 (1.01 g, 2.05 mmol) in DMF (15 mL), with additional DMF (2 mL) used to complete the transfer. The mixture was stirred at 0° C. for 3.5 h, then pyridine (0.66 mL, 8.2 mmol) was added, and the reaction was heated to 55° C. for 18 h. The resultant solution was diluted with EtOAc, washed with 1 N HCl, 5% $Na_2SO_3$, and brine, dried with $Na_2SO_4$, and concentrated. The residue was purified by column chromatography (silica gel, 0% to 100% EtOAc in hexanes) to give compound TX63608 (805 mg, 80%) as an off-white solid: $^1$H NMR (400 MHz, $CDCl_3$) δ 8.04 (s, 1H), 5.98 (s, 1H), 3.78 (m, 2H), 3.11 (d, 1H, J=4.7 Hz), 2.25 (td, 1H, J=4.0, 13.6 Hz), 1.65 (m, 12H), 1.50 (s, 3H), 1.50 (s, 3H), 1.26 (s, 3H), 1.25 (m, 4H), 1.18 (s, 3H), 1.06 (m, 2H), 1.01 (s, 3H), 0.93 (s, 3H), 0.87 (s, 3H); m/z 492.3 (M+1).

Compound TX63609:

A solution of compound TX63608 (50.5 mg, 0.103 mmol), MeOTf (57 µL, 0.50 mmol) and 2,6-di-tert-butyl-4-methylpyridine (128 mg, 0.623 mmol) in $CH_2Cl_2$ (2 mL) was stirred at room temperature for 19 h. The resultant mixture was diluted with EtOAc, washed with 1 N HCl and brine, dried with $Na_2SO_4$, and concentrated. The residue was purified by column chromatography (silica gel, 0% to 100% EtOAc in hexanes) to give compound TX63609 (39.5 mg, 76%) as a white solid: $^1$H NMR (400 MHz, $CDCl_3$) δ 8.04 (s, 1H), 5.97 (s, 1H), 3.45 (m, 2H), 3.32 (s, 3H), 3.09 (d, 1H, J=4.7 Hz), 2.25 (td, 1H, J=4.1, 13.4 Hz), 1.66 (m, 11H), 1.50 (s, 3H), 1.48 (s, 3H), 1.26 (s, 3H), 1.25 (m, 4H), 1.18 (s, 3H), 1.05 (m, 2H), 1.01 (s, 3H), 0.94 (s, 3H), 0.87 (s, 3H); m/z 506.3 (M+1).

Compound TX63610:

A solution of compound TX63608 (49.6 mg, 0.101 mmol), $Ac_2O$ (48 µL, 0.51 mmol), pyridine (81 µL, 1.0 mmol) and DMAP (3.4 mg, 0.028 mmol) in $CH_2Cl_2$ (2 mL) was stirred at room temperature for 20 h. The resultant mixture was diluted with EtOAc, washed with 1 N HCl, saturated $NaHCO_3$, and brine, dried with $Na_2SO_4$, and concentrated. The residue was purified by column chromatography (silica gel, 0% to 100% EtOAc in hexanes) to give compound TX63610 (41.1 mg, 76%) as a white solid: $^1$H NMR (400 MHz, $CDCl_3$) δ 8.04 (s, 1H), 5.98 (s, 1H), 4.16 (m, 2H), 3.08 (d, 1H, J=4.7 Hz), 2.25 (td, 1H, J=4.0, 13.5 Hz), 2.03 (s, 3H), 1.66 (m, 11H), 1.50 (s, 3H), 1.49 (s, 3H), 1.26 (s, 3H), 1.25 (m, 4H), 1.18 (s, 3H), 1.07 (m, 2H), 1.01 (s, 3H), 0.93 (s, 3H), 0.87 (s, 3H); m/z 534.3 (M+1).

Compound TX63981:

A solution of compound TX63608 (41.4 mg, 0.0842 mmol) and EtNCO (64 µL, 0.81 mmol) in toluene (0.5 mL) was stirred at room temperature for 1 h, then heated to 70° C. for >4 h. The reaction mixture was cooled to room temperature and was purified directly by column chromatography (silica gel, 0% to 100% EtOAc in hexanes) to give compound TX63981 (34.5 mg, 73%) as a white solid: $^1$H NMR (400 MHz, $CDCl_3$) δ 8.04 (s, 1H), 5.97 (s, 1H), 4.58 (s, 1H), 4.23 (m, 1H), 4.12 (m, 1H), 3.19 (m, 2H), 3.09 (d, 1H, J=4.6 Hz), 2.30 (td, 1H, J=4.1, 13.2 Hz), 1.67 (m, 11H), 1.50 (s, 3H), 1.49 (s, 3H), 1.26 (s, 3H), 1.19 (m, 6H), 1.18 (s, 3H), 1.12 (t, 3H, J=7.2 Hz), 1.01 (s, 3H), 0.94 (s, 3H), 0.88 (s, 3H); m/z 563.4 (M+1).

Compound 29:

DIBAL-H (1.0 M in THF, 5 mL, 5.0 mmol) was added to a 0° C. solution of 8a, 8b (8a:8b=2:3, 0.50 g, 0.92 mmol) in THF (10 mL). The reaction mixture was stirred at 0° C. for 30 min, then warmed to room temperature for 2.5 h. The mixture was cooled to 0° C., quenched with saturated NaK tartrate (10 mL), diluted with MTBE (25 mL), warmed to room temperature over 1 h, diluted with additional saturated NaK tartrate (40 mL), then and extracted with MTBE. The combined organic fractions were washed with brine, dried with $Na_2SO_4$, filtered through a short plug of celite, eluted with MTBE, and concentrated to give compound 29 (491 mg, mixture of $Cl_2$-epimers, quantitative) as a white solid: m/z 492.3 (M+1).

Compound 30:

NBS (244 mg, 1.37 mmol) was added to a room temperature solution of compound 29 (all above obtained, ≤0.92 mmol) in DME/water (9:1 mixture, 10 mL). The reaction was stirred at room temperature for 2 h, quenched by the addition of 5% $Na_2SO_3$, stirred 15 min at room temperature, and then extracted with EtOAc. The organic fraction was washed with brine, dried with $Na_2SO_4$, and concentrated. The residue was purified by flash chromatography (silica gel, 0% to 100% EtOAc in hexanes) to give compound 30 (491 mg, quantitative) as a white solid: m/z 508.3 (M+1).

Compound 31:

A solution of compound 30 (all above obtained, ≤0.92 mmol) and NaOMe (25% in MeOH, 1.3 mL) in MeOH was stirred at 55° C. for 16 h. The resultant mixture was diluted with 1 N HCl and extracted with EtOAc. The combined organic fractions were washed with brine, dried with $Na_2SO_4$, and concentrated. The residue was purified by flash chromatography (silica gel, 0% to 80% EtOAc in hexanes) to give compound 31 (151 mg, 32%) as a white solid: m/z 508.3 (M+1).

Compound TX63744:

1,3-dibromo-5,5-dimethylhydantoin (45 mg, 0.16 mmol) was added to a 0° C. solution of compound 31 (151 mg, 0.278 mmol) in DMF (10 mL). The mixture was stirred at 0° C. for 2.5 h. Pyridine (0.10 mL, 1.2 mmol) was then added, and the reaction heated to 55° C. overnight. The resultant solution was diluted with EtOAc, washed with 1 N HCl, 10% $Na_2SO_3$, and brine, dried with $Na_2SO_4$, and concentrated. The residue was purified by column chromatography (silica gel, 0% to 80% EtOAc in hexanes) to give compound TX63744 (82 mg, 58%) as a white solid: $^1$H NMR (400 MHz, $CDCl_3$) δ 8.04 (s, 1H), 5.97 (s, 1H), 3.66 (m, 2H), 3.05 (d, 1H, J=4.7 Hz), 2.25 (td, 1H, J=4.1, 13.6 Hz), 1.66 (m, 14H), 1.49 (s, 3H), 1.47 (s, 3H), 1.26 (s, 3H), 1.23 (m, 4H), 1.18 (s, 3H), 1.04 (m, 2H), 1.01 (s, 3H), 0.93 (s, 3H), 0.87 (s, 3H); m/z 506.3 (M+1).

Compound TX63983:

A solution of compound TX63744 (24.1 mg, 0.0477 mmol) and EtNCO (39 μL, 0.49 mmol) in toluene (0.5 mL) was heated to 70° C. for 20 h, then purified directly by column chromatography (silica gel, 0% to 100% EtOAc in hexanes) to give compound TX63983 (20.7 mg, 75%) as a white solid: $^1$H NMR (400 MHz, $CDCl_3$) δ 8.04 (s, 1H), 5.98 (s, 1H), 4.55 (s, 1H), 4.04 (m, 2H), 3.21 (m, 2H), 3.02 (d, 1H, J=4.6 Hz), 2.24 (td, 1H, J=4.0, 12.8 Hz), 1.66 (m, 13H), 1.50 (s, 3H), 1.46 (s, 3H), 1.26 (s, 3H), 1.25 (m, 4H), 1.18 (s, 3H), 1.14 (t, 3H, J=7.2 Hz), 1.04 (m, 2H), 1.01 (s, 3H), 0.93 (s, 3H), 0.88 (s, 3H); m/z 577.4 (M+1).

All of the compounds, compositions and methods disclosed and claimed herein can be made and executed without undue experimentation in light of the present disclosure. While the disclosure may have only been described in terms of certain embodiments, it will be apparent to those of skill in the art that variations may be applied to the compounds, compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

U.S. Pat. No. 7,915,402
U.S. Pat. No. 7,943,778
U.S. Pat. No. 8,071,632
U.S. Pat. No. 8,124,799
U.S. Pat. No. 8,129,429
U.S. Pat. No. 8,338,618
Abraham and Kappas, *Free Radical Biol. Med.*, 39:1-25, 2005.
Ahmad et al., *Cancer Res.*, 68:2920-2926, 2008.
Ahmad et al., *J. Biol. Chem.*, 281:35764-9, 2006.
Araujo et al., *J. Immunol.*, 171(3):1572-1580, 2003.
Bach, *Hum. Immunol.*, 67(6):430-432, 2006.
Chauhan and Chauhan, *Pathophysiology*, 13(3):171-181 2006.
Dickerson et al., *Prog Neuropsychopharmacol Biol. Psychiatry*, Mar. 6, 2007.
Dinkova-Kostova et al., *Proc. Natl. Acad. Sci. USA*, 102 (12):4584-4589, 2005.
Dudhgaonkar et al., *Eur. J. Pain*, 10(7):573-9, 2006.
Forstermann, *Biol. Chem.*, 387:1521, 2006.
*Handbook of Pharmaceutical Salts: Properties, and Use*, Stahl and Wermuth Eds.), Verlag Helvetica Chimica Acta, 2002.
Hanson et al., *BMC Medical Genetics*, 6(7), 2005.
Honda et al. *Bioorg. Med. Chem. Lett.*, 12:1027-1030, 2002.
Honda et al., *J. Med. Chem.*, 43:4233-4246, 2000a.
Honda, et al., *J. Med. Chem.*, 43:1866-1877, 2000b.
Honda et al., *Bioorg. Med. Chem. Lett.*, 7:1623-1628, 1997.
Honda et al., *Bioorg. Med. Chem. Lett.*, 9(24):3429-3434, 1999.
Honda et al., *Bioorg. Med. Chem. Lett.*, 8(19):2711-2714, 1998.
Honda et al., *Bioorg. Med. Chem. Lett.*, 16(24):6306-6309, 2006.
Hong et al., *Clin Cancer Res*, 18(12):3396-406, 2012.
Ishikawa et al., *Circulation*, 104(15):1831-1836, 2001.
Kawakami et al., *Brain Dev* 28(4):243-246, 2006.
Kendall-Tackett, *Trauma Violence Abuse*, 8(2):117-126, 2007.
Kruger et al., *J. Pharmacol. Exp. Ther.*, 319(3):1144-1152, 2006.
Lee et al., *Glia.*, 55(7):712-22, 2007.
Lencz et al., *Mol. Psychiatry*, 12(6):572-80, 2007.
Liby et al., *Cancer Res.*, 65(11):4789-4798, 2005.
Liby et al., *Nat. Rev. Cancer*, 7(5):357-356, 2007a.
Liby et al., *Mol. Cancer Ther* 6(7):2113-9, 2007b.
Liby et al., 2007b
Liu et al., *FASEB J.*, 20(2):207-216, 2006.
Lu et al., *J. Clin. Invest.*, 121(10):4015-29, 2011.
*March's Advanced Organic Chemistry: Reactions*, Mechanisms, and Structure, 2007.
McIver et al., *Pain*, 120(1-2):161-9, 2005.
Morris et al., *J. Mol. Med.*, 80(2):96-104, 2002.
Morse and Choi, *Am. J. Respir. Crit. Care Med.*, 172(6): 660-670, 2005.
Morse and Choi, *Am. J. Respir. Crit. Care Med.*, 27(1):8-16, 2002.
Pall, *Med. Hypoth.*, 69:821-825, 2007.
Pergola et. al., *N Engl J Med*, 365:327-336, 2011.
Place et al., *Clin. Cancer Res.*, 9(7):2798-806, 2003.
Rajakariar et al., *Proc. Natl. Acad. Sci. USA*, 104(52):20979-84, 2007.
Ross et al., *Am. J. Clin. Pathol.*, 120(Suppl):553-71, 2003.
Ross et al., *Expert Rev. Mol. Diagn.*, 3(5):573-585, 2003.
Ruster et al., *Scand. J. Rheumatol.*, 34(6):460-3, 2005.
Sacerdoti et al., *Curr Neurovasc Res.* 2(2):103-111, 2005.
Salvemini et al., *J. Clin. Invest.*, 93(5):1940-1947, 1994.
Sarchielli et al., *Cephalalgia*, 26(9):1071-1079, 2006.
Satoh et al., *Proc. Natl. Acad. Sci. USA*, 103(3):768-773, 2006.
Schulz et al., *Antioxid. Redox. Sig.*, 10:115, 2008.
Strejan et al., *J. Neuroimmunol.*, 7:27, 1984.
Suh et al., *Cancer Res.*, 58:717-723, 1998.
Suh et al., *Cancer Res.*, 59(2):336-341, 1999.
Szabo et al., *Nature Rev. Drug Disc.*, 6:662-680, 2007.
Takahashi et al., *Cancer Res.*, 57:1233-1237, 1997.
Tamir and Tannebaum, *Biochim. Biophys. Acta*, 1288:F31-F36, 1996.
Xie et al., *J. Biol. Chem.*, 270(12):6894-6900, 1995.
Zhou et al., *Am. J. Pathol.*, 166(1):27-37, 2005.

What is claimed is:

1. A compound of the formula:

(III)

wherein:

n is 1 to 6;

$R_1$ and $R_2$ are each independently —H, —OH, methyl, or as defined below; and $R_3$ is:

amino or —NHOH; or

N-heteroaryl$_{(C\leq 8)}$, N-heterocycloalkyl$_{(C\leq 8)}$, alkylamino$_{(C\leq 8)}$, dialkylamino$_{(C\leq 8)}$, alkenylamino$_{(C\leq 8)}$, alkoxyamino$_{(C\leq 8)}$, arylamino$_{(C\leq 8)}$, aralkylamino$_{(C\leq 8)}$, heteroarylamino$_{(C\leq 8)}$, heterocycloalkylamino$_{(C\leq 8)}$, alkylsulfonylamino$_{(C\leq 8)}$, amido$_{(C\leq 8)}$, —NH-amido$_{(C\leq 8)}$, or a substituted version of any of these groups;

$R_3$ and $R_1$, taken together, are —NR$_a$—, wherein $R_a$ is hydrogen or alkyl$_{(C\leq 4)}$; or $R_3$ and $R_2$, taken together, are wherein —NR$_a$— is hydrogen or alkyl$_{(C\leq 4)}$; or or a pharmaceutically acceptable salt thereof.

2. The compound of claim 1, further defined as:

(IV)

wherein:

n is 1 to 6; and $R_3$ is:

amino or —NHOH; or

N-heteroaryl$_{(C\leq 8)}$, N-heterocycloalkyl$_{(C\leq 8)}$, alkylamino$_{(C\leq 8)}$, dialkylamino$_{(C\leq 8)}$, alkenylamino$_{(C\leq 8)}$, alkoxyamino$_{(C\leq 8)}$, arylamino$_{(C\leq 8)}$, aralkylamino$_{(C\leq 8)}$, heteroarylamino$_{(C\leq 8)}$, heterocycloalkylamino$_{(C\leq 8)}$, alkyl sulfonylamino$_{(C\leq 8)}$, amido$_{(C\leq 8)}$, —NH-amido$_{(C\leq 8)}$, or a substituted version of any of these groups;

or a pharmaceutically acceptable salt thereof.

3. The compound of claim 1, wherein n is 1.

4. The compound of claim 1, wherein n is 2.

5. The compound of claim 1, wherein n is 3.

6. The compound of claim 1, wherein $R_1$ is —H.

7. The compound of claim 1, wherein $R_2$ is methyl.

8. The compound of claim 1, wherein $R_3$ is N-heteroaryl$_{(C\leq 8)}$.

9. The compound of claim 8, wherein $R_3$ is imidazolyl.

10. The compound of claim 1, wherein $R_3$ is N-heterocycloalkyl$_{(C\leq 8)}$.

11. The compound of claim 10, wherein $R_3$ is morpholinyl or pyrrolidinyl.

12. The compound of claim 1, wherein $R_3$ is alkylamino$_{(C\leq 8)}$.

13. The compound of claim 12, wherein $R_3$ is ethylamino.

14. The compound of claim 1, further defined as:
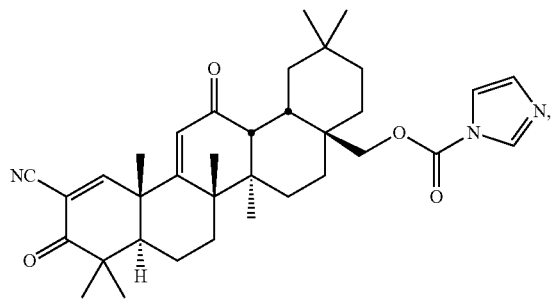
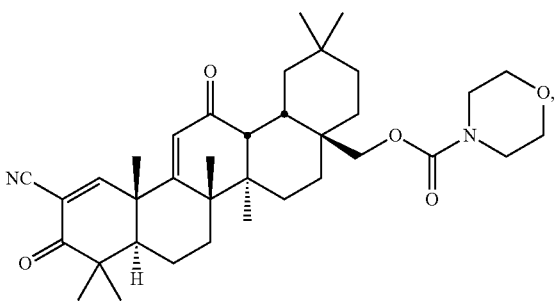
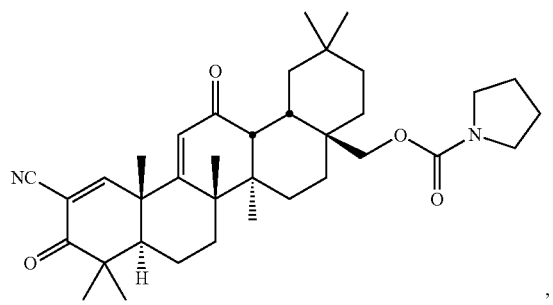
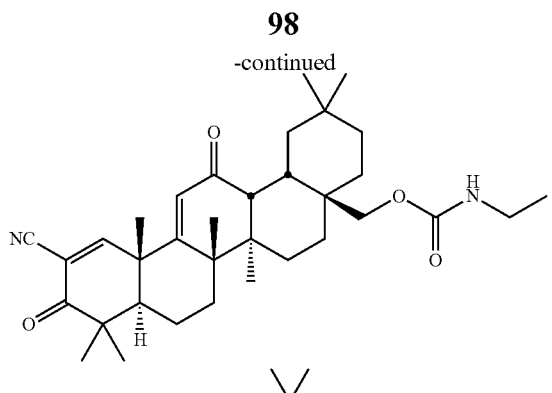
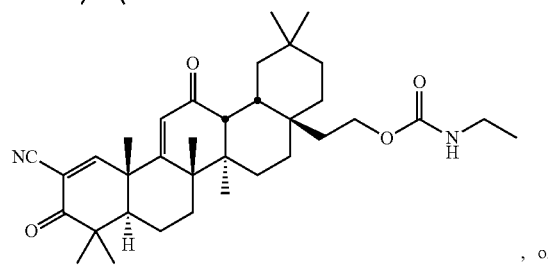
, or
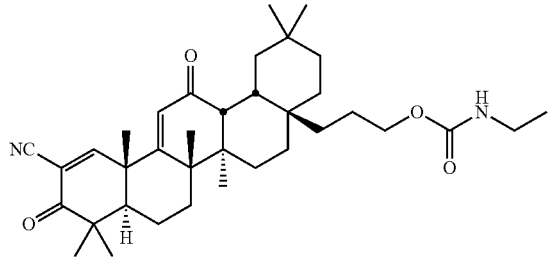
,
or a pharmaceutically acceptable salt thereof.
15. A pharmaceutical composition comprising:
 a) the compound of claim 1; and
 b) an excipient.
* * * * *

UNITED STATES PATENT AND TRADEMARK OFFICE
CERTIFICATE OF CORRECTION

PATENT NO. : 10,501,489 B2
APPLICATION NO. : 15/433100
DATED : December 10, 2019
INVENTOR(S) : Christopher F. Bender et al.

Page 1 of 1

It is certified that error appears in the above-identified patent and that said Letters Patent is hereby corrected as shown below:

In the Claims

In Claim 1, Column 95, Line 65, delete "are wherein $-NR_a-$" and insert --are $-NR_a-$, wherein $R_a$-- therefor.

In Claim 1, Column 95, Line 67, delete "or".

In Claim 2, Column 96, Line 45, delete "alkyl sulfonylamino$_{(c\leq8)}$," and insert --alkylsulfonylamino$_{(c\leq8)}$,-- therefor.

Signed and Sealed this
Twenty-fifth Day of February, 2020

Andrei Iancu
*Director of the United States Patent and Trademark Office*